United States Patent [19]
Hamann et al.

[11] Patent Number: 5,767,285
[45] Date of Patent: Jun. 16, 1998

[54] LINKERS USEFUL FOR THE SYNTHESIS OF CONJUGATES OF METHYLTRITHIO ANTITUMOR AGENTS

[75] Inventors: Philip Ross Hamann, Garnerville; Lois Hinman, N. Tarrytown; Irwin Hollander, Monsey, all of N.Y.; Ryan Holcomb, Glen Rock, N.J.; William Hallett; Hwei-Ru Tsou, both of New City, N.Y.; Martin J. Weiss, Ft. Lee, N.J.

[73] Assignee: American Cyanamid Company, Madison, N.J.

[21] Appl. No.: 462,939

[22] Filed: Jun. 5, 1995

Related U.S. Application Data

[62] Division of Ser. No. 253,877, Jun. 3, 1994.
[51] Int. Cl.$^6$ .................. C07D 207/46; C07D 207/48; C07D 295/22
[52] U.S. Cl. ................. 548/542; 544/38; 560/19; 564/152; 564/163; 530/391.9; 530/402
[58] Field of Search ................. 530/391.9, 399, 530/402; 514/12, 25, 26, 54, 61, 53, 169; 544/38; 548/542; 560/19; 564/152, 163

[56] References Cited

U.S. PATENT DOCUMENTS 5,053,394  10/1991  Ellestad et al. .................. 514/25

*Primary Examiner*—Ponnathapura Achutamurthy
*Attorney, Agent, or Firm*—Elizabeth M. Barnhard; H. G. Jackson

[57] ABSTRACT

This invention describes carrier-drug conjugates prepared from disulfide analogs of the calicheamicin family of potent antitumor antibiotics and their derivatives, as well as similar analogs from related antitumor antibiotics such as the esperamicins. The carrier can be an antibody, growth factor, or steroid which targets an undesired population of cells, such as those of a tumor. Whole protein carriers as well as their antigen-recognizing fragments and their chemically or genetically manipulated counterparts are useful for the targeting portion of the conjugates. This invention includes compounds required for the synthesis of these conjugates, appropriate pharmaceutical compositions of the carrier-drug conjugates, and their method of use.

26 Claims, 12 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 426 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 22..420

( x i ) SEQUENCE DESCRIPTION: SEQ ID NO:1:

```
GGACTGTTCG AAGCCGCCAC C ATG TCT GTC CCC ACC CAA GTC CTC GGA CTC          51
                         Met Ser Val Pro Thr Gln Val Leu Gly Leu
                          1               5                  10

CTG CTG CTG TGG CTT ACA GAT GCC AGA TGC GAT ATC CAG CTC ACT CAG          99
Leu Leu Leu Trp Leu Thr Asp Ala Arg Cys Asp Ile Gln Leu Thr Gln
             15                  20                  25

AGT CCA AGT ACT CTC AGT GCC AGT GTA GGT GAT AGG GTC ACC ATC ACT         147
Ser Pro Ser Thr Leu Ser Ala Ser Val Gly Asp Arg Val Thr Ile Thr
             30                  35                  40

TGT AGG GCC TCT GAA TCT CTC GAT AAC TAT GGT ATC AGG TTC CTC ACT         195
Cys Arg Ala Ser Glu Ser Leu Asp Asn Tyr Gly Ile Arg Phe Leu Thr
         45                  50                  55

TGG TTC CAG CAG AAA CCA GGT AAA GCC CCA AAG CTC CTC ATG TAT GCC         243
Trp Phe Gln Gln Lys Pro Gly Lys Ala Pro Lys Leu Leu Met Tyr Ala
         60                  65                  70

GCC TCT AAC CAG GGT TCT GGT GTA CCA TCT AGA TTC AGT GGT AGT GGT         291
Ala Ser Asn Gln Gly Ser Gly Val Pro Ser Arg Phe Ser Gly Ser Gly
 75                  80                  85                  90

AGT GGT ACT GAG TTC ACT CTC ACT ATC AGT AGT CTC CAG CCA GAT GAT         339
Ser Gly Thr Glu Phe Thr Leu Thr Ile Ser Ser Leu Gln Pro Asp Asp
                 95                 100                 105

TTC GCC ACT TAT TAT TGT CAG CAG ACT AAA GAA GTA CCA TGG TCT TTC         387
Phe Ala Thr Tyr Tyr Cys Gln Gln Thr Lys Glu Val Pro Trp Ser Phe
            110                 115                 120

GGT CAG GGT ACT AAA GTA GAA GTA AAA CGT ACG GGCCGG                      426
Gly Gln Gly Thr Lys Val Glu Val Lys Arg Thr
            125                 130
```

( 2 ) INFORMATION FOR SEQ ID NO:2:

( i ) SEQUENCE CHARACTERISTICS:
        ( A ) LENGTH: 133 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ser Val Pro Thr Gln Val Leu Gly Leu Leu Leu Leu Trp Leu Thr
 1               5                  10                  15

Asp Ala Arg Cys Asp Ile Gln Leu Thr Gln Ser Pro Ser Thr Leu Ser
```

|  |  | 20 |  |  |  | 25 |  |  |  | 30 |  |  |
|---|---|---|---|---|---|---|---|---|---|---|---|---|

Ala Ser Val Gly Asp Arg Val Thr Ile Thr Cys Arg Ala Ser Glu Ser
        35                    40                    45

Leu Asp Asn Tyr Gly Ile Arg Phe Leu Thr Trp Phe Gln Gln Lys Pro
    50                    55                    60

Gly Lys Ala Pro Lys Leu Leu Met Tyr Ala Ala Ser Asn Gln Gly Ser
65                    70                    75                    80

Gly Val Pro Ser Arg Phe Ser Gly Ser Gly Ser Gly Thr Glu Phe Thr
                85                    90                    95

Leu Thr Ile Ser Ser Leu Gln Pro Asp Asp Phe Ala Thr Tyr Tyr Cys
            100                    105                    110

Gln Gln Thr Lys Glu Val Pro Trp Ser Phe Gly Gln Gly Thr Lys Val
        115                    120                    125

Glu Val Lys Arg Thr
        130

( 2 ) INFORMATION FOR SEQ ID NO:3:

( i ) SEQUENCE CHARACTERISTICS:
        ( A ) LENGTH: 449 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 22..444

( x i ) SEQUENCE DESCRIPTION: SEQ ID NO:3:

```
GCGCGCAAGC TTGCCGCCAC C ATG GAA TGG AGC TGG GTC TTT CTC TTC TTC      51
                       Met Glu Trp Ser Trp Val Phe Leu Phe Phe
                       1               5                   10

CTG TCA GTA ACT ACA GGA GTC CAT TCT GAG GTG CAG CTG GTG CAG TCT       99
Leu Ser Val Thr Thr Gly Val His Ser Glu Val Gln Leu Val Gln Ser
                15                  20                  25

GGA GCA GAG GTG AAG AAG CCT GGA TCT TCT GTG AAG GTG TCT TGT AAG      147
Gly Ala Glu Val Lys Lys Pro Gly Ser Ser Val Lys Val Ser Cys Lys
                30                  35                  40

GCA TCT GGA TAC ACA ATT ACA GAC TCC AAT ATT CAC TGG GTG AGA CAG      195
Ala Ser Gly Tyr Thr Ile Thr Asp Ser Asn Ile His Trp Val Arg Gln
                45                  50                  55

GCA CCT GGA CAG TCC CTC GAG TGG ATT GGA TAC ATT TAC CCT TAC AAT      243
Ala Pro Gly Gln Ser Leu Glu Trp Ile Gly Tyr Ile Tyr Pro Tyr Asn
        60                  65                  70

GGA GGA ACA GAC TAC AAT CAG AAG TTC AAG AAT AGA GCA ACA CTG ACA      291
Gly Gly Thr Asp Tyr Asn Gln Lys Phe Lys Asn Arg Ala Thr Leu Thr
75                  80                  85                  90

GTG GAC AAT CCT ACG AAT ACC GCC TAC ATG GAG CTG TCT TCT CTG AGA      339
Val Asp Asn Pro Thr Asn Thr Ala Tyr Met Glu Leu Ser Ser Leu Arg
                95                  100                 105

TCT GAG GAC ACA GAC TTC TAC TAC TGT GTG AAT GGA AAT CCT TGG CTG      387
Ser Glu Asp Thr Asp Phe Tyr Tyr Cys Val Asn Gly Asn Pro Trp Leu
            110                 115                 120

GCT TAC TGG GGA CAG GGA ACT CTG GTG ACA GTG TCT TCT GCC TCA ACG      435
Ala Tyr Trp Gly Gln Gly Thr Leu Val Thr Val Ser Ser Ala Ser Thr
        125                 130                 135
```

```
AAG  GGC  CCG  CGCGC                                                                    449
Lys  Gly  Pro
      140
```

( 2 ) INFORMATION FOR SEQ ID NO:4:

( i ) SEQUENCE CHARACTERISTICS:
    ( A ) LENGTH: 141 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

| Met | Glu | Trp | Ser | Trp | Val | Phe | Leu | Phe | Phe | Leu | Ser | Val | Thr | Thr | Gly |
|---|---|---|---|---|---|---|---|---|---|---|---|---|---|---|---|
| 1 | | | | 5 | | | | | 10 | | | | | 15 | |
| Val | His | Ser | Glu | Val | Gln | Leu | Val | Gln | Ser | Gly | Ala | Glu | Val | Lys | Lys |
| | | | 20 | | | | | 25 | | | | | 30 | | |
| Pro | Gly | Ser | Ser | Val | Lys | Val | Ser | Cys | Lys | Ala | Ser | Gly | Tyr | Thr | Ile |
| | | 35 | | | | | 40 | | | | | 45 | | | |
| Thr | Asp | Ser | Asn | Ile | His | Trp | Val | Arg | Gln | Ala | Pro | Gly | Gln | Ser | Leu |
| | 50 | | | | | 55 | | | | | 60 | | | | |
| Glu | Trp | Ile | Gly | Tyr | Ile | Tyr | Pro | Tyr | Asn | Gly | Gly | Thr | Asp | Tyr | Asn |
| 65 | | | | | 70 | | | | | 75 | | | | | 80 |
| Gln | Lys | Phe | Lys | Asn | Arg | Ala | Thr | Leu | Thr | Val | Asp | Asn | Pro | Thr | Asn |
| | | | | 85 | | | | | 90 | | | | | 95 | |
| Thr | Ala | Tyr | Met | Glu | Leu | Ser | Ser | Leu | Arg | Ser | Glu | Asp | Thr | Asp | Phe |
| | | | 100 | | | | | 105 | | | | | 110 | | |
| Tyr | Tyr | Cys | Val | Asn | Gly | Asn | Pro | Trp | Leu | Ala | Tyr | Trp | Gly | Gln | Gly |
| | | 115 | | | | | 120 | | | | | 125 | | | |
| Thr | Leu | Val | Thr | Val | Ser | Ser | Ala | Ser | Thr | Lys | Gly | Pro | | | |
| | 130 | | | | | 135 | | | | | 140 | | | | |

LINKERS USEFUL FOR THE SYNTHESIS OF CONJUGATES OF METHYLTRITHIO ANTITUMOR AGENTS

This is a divisional of copending application Ser. No. 08/253,877 filed on Jun. 3, 1994.

SUMMARY OF THE INVENTION

This invention describes carrier-drug conjugates prepared from disulfide analogs of the calicheamicin family of potent antitumor antibiotics and their derivatives, as well as similar analogs from related antitumor antibiotics such as the esperamicins. The carrier can be an antibody, growth factor, or steroid which targets an undesired population of cells, such as those of a tumor. Whole protein carriers as well as their antigen-recognizing fragments and their chemically or genetically manipulated counterparts are useful for the targeting portion of the conjugates. This invention includes compounds required for the synthesis of these conjugates, appropriate pharmaceutical compositions of the carrier-drug conjugates, and their method of use.

More specifically, one aspect of the invention includes a cytotoxic drug conjugate of the formula:

$$Z^3[CO\text{-}Alk^1\text{-}Sp^1\text{-}Ar\text{-}Sp^2\text{-}Alk^2\text{-}C(Z^1)=Z^2]_m$$

wherein $Z^3$ is a protein selected from mono- and polyclonal antibodies, their antigen-recognizing fragments, and their chemically or genetically manipulated counterparts and growth factors and their chemically or genetically manipulated counterparts, wherein a covalent bond to the protein is an amide formed from reaction with lysine side chains, or a steroid, wherein the covalent bond to the steroid is an amide or an ester;

m is from about 0.1 to 15;

$Alk^1$ and $Alk^2$ are independently a bond or branched or unbranched ($C_1$–$C_{10}$) alkylene chain;

$Sp^1$ is a bond, —S—, —O—, —CONH—, —NHCO—, —NR'—, —N(CH$_2$CH$_2$)$_2$N—, or —X—Ar'—Y—(CH$_2$)$_n$—Z wherein X, Y, and Z are independently a bond, —NR'—, —S—, or —O—, with the proviso that when n=0, then at least one of Y and Z must be a bond and Ar' is 1,2-, 1,3-, or 1,4-phenylene optionally substituted with one, two, or three groups of ($C_1$–$C_5$) alkyl, ($C_1$–$C_4$) alkoxy, ($C_1$–$C_4$) thioalkoxy, halogen, nitro, COOR', CONHR', O(CH$_2$)$_n$COOR', S(CH$_2$)$_n$COOR', O(CH$_2$)$_n$CONHR', or S(CH$_2$)$_n$CONHR', with the proviso that when $Alk^1$ is a bond, $Sp^1$ is also a bond;

n is an integer from 0 to 5;

R' is a branched or unbranched ($C_1$–$C_5$) chain optionally substituted by one or two groups of —OH, ($C_1$–$C_4$) alkoxy, ($C_1$–$C_4$) thioalkoxy, halogen, nitro, ($C_1$–$C_3$) dialkylamino, or ($C_1$–$C_3$) trialkylammonium-A$^-$ where A$^-$ is a pharmaceutically acceptable anion completing a salt;

$Sp^2$ is a bond, —S—, or —O—, with the proviso that when $Alk^2$ is a bond, $Sp^2$ is also a bond;

$Z^1$ is H, ($C_1$–$C_5$) alkyl, or phenyl optionally substituted with one, two, or three groups of ($C_1$–$C_5$) alkyl, ($C_1$–$C_4$) alkoxy, ($C_1$–$C_4$) thioalkoxy, halogen, nitro, COOR', CONHR', O(CH$_2$)$_n$COOR', S(CH$_2$)$_n$COOR', O(CH$_2$)$_n$CONHR', or S(CH$_2$)$_n$CONHR, wherein n and R' are as hereinbefore defined;

Ar is 1,2-, 1,3-, or 1,4-phenylene optionally substituted with one, two, or three groups of ($C_1$–$C_6$) alkyl, ($C_1$–$C_5$) alkoxy, ($C_1$–$C_4$) thioalkoxy, halogen, nitro, COOR', CONHR', O(CH$_2$)$_n$COOR', S(CH$_2$)$_n$COOR', O(CH$_2$)$_n$CONHR', or S(CH$_2$)$_n$CONHR' wherein n and R' are as hereinbefore defined or a 1,2-, 1,3-, 1,4-, 1,5-, 1,6-, 1,7-, 1,8-, 2,3-, 2,6-, or 2,7-naphthylidene or

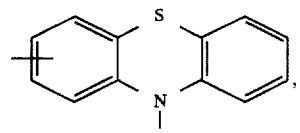

each naphthylidene or phenothiazine optionally substituted with one, two, three, or four groups of ($C_1$–$C_6$) alkyl, ($C_1$–$C_5$) alkoxy, ($C_1$–$C_4$) thioalkoxy, halogen, nitro, or COOR', CONHR', O(CH$_2$)$_n$COOR', S(CH$_2$)$_n$COOR', O(CH$_2$)$_n$CONHR', or S(CH$_2$)$_n$CONHR' wherein n and R' are as hereinbefore defined, with the proviso that when Ar is naphthylidene, $Z^1$ is not hydrogen and with the proviso that when Ar is phenothiazine, $Sp^1$ is a bond only connected to nitrogen;

$Z^2$ is Q-Sp-S-S-W, wherein W is

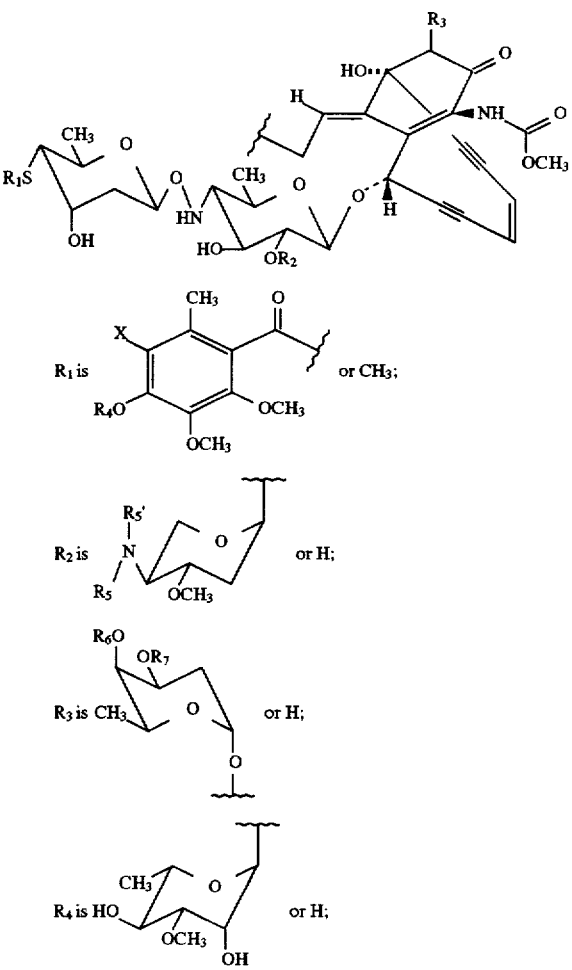

R₆ or R₇ is H or 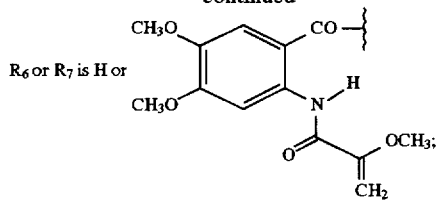

R₅ is —CH₃, —C₂H₅, or —CH(CH₃)₂; X is an iodine or bromine atom; R₅' is a hydrogen or the group RCO, wherein R is hydrogen, branched or unbranched (C₁–C₁₀) alkyl or (C₁–C₁₀) alkylene group, a (C₆–C₁₁) aryl group, a (C₆–C₁₁) aryl-alkyl (C₁–C₅) group, or a heteroaryl or heteroaryl-alkyl (C₁–C₅) group wherein heteroaryl is defined as 2- or 3-furyl, 2- or 3-thienyl, 2- or 3-(N-methylpyrrolyl), 2-, 3-, or 4-4-pyridyl, 2-, 4-, or 5-(N-methylimidazolyl), 2-, 4-, or 5-oxazolyl, 2-, 3-, 5-, or 6-pyrimidinyl, 2-, 3-, 4-, 5-, 6-, 7-, or 8-quinolyl, or 1-, 3-, 4-, 5-, 6-, 7-, or 8-isoquinolyl, all aryl and heteroaryl groups optionally substituted by one or more hydroxy, amino, carboxy, halo, nitro, lower (C₁–C₃) alkoxy, or lower (C₁–C₅) thioalkoxy groups;

Sp is a straight or branched-chain divalent or trivalent (C₁–C₁₈) radical, divalent or trivalent aryl or heteroaryl radical, divalent or trivalent (C₃–C₁₈) cycloalkyl or heterocycloalkyl radical, divalent or trivalent aryl- or heteroaryl-alkyl (C₁–C₁₈) radical, divalent or trivalent cycloalkyl- or heterocycloalkyl-alkyl (C₁–C₁₈) radical or divalent or trivalent (C₂–C₁₈) unsaturated alkyl radical, wherein heteroaryl is furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein if Sp is a trivalent radical, it can be additionally substituted by lower (C₁–C₅) dialkylamino, lower (C₁–C₅) alkoxy, hydroxy, or lower (C₁–C₅) alkylthio groups; and Q is =NHNCO—, =NHNCS—, =NHNCONH—, =NHNCSNH—, or =NO— and includes the conjugates use as antitumor agents.

A second aspect of this invention involves modified drugs, useful as intermediates for constructing conjugates, of the formula:

wherein Z¹, Z², Alk¹, Sp¹, Ar, Sp², and Alk² are as hereinbefore defined;

Z³ is halogen, hydroxy, OM wherein M is a metal completing a salt, —N₃,

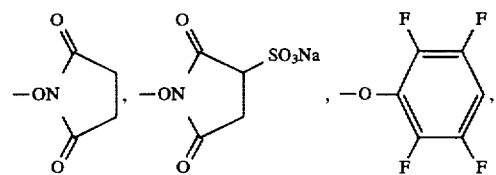

and m is 1.

A third aspect of this invention involves linkers, useful for constructing drug conjugates, of the formula:

wherein Z³ is halogen, hydroxy, OM wherein M is a metal completing a salt, —N₃,

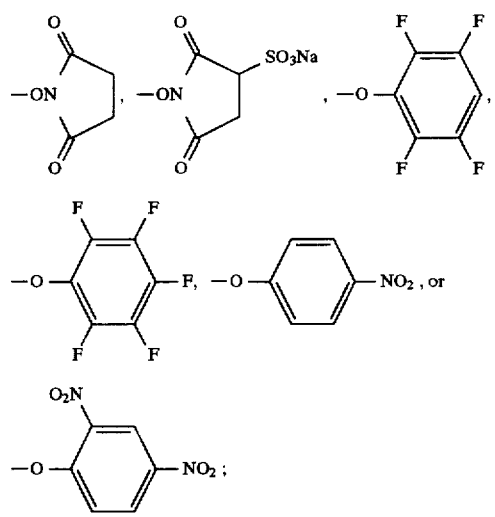

Alk¹ and Alk² are independently a bond or branched or unbranched (C₁–C₁₀) alkylene chain;

Sp¹ is a bond, —S—, —O—, —CONH—, —NHCO—, —NR'—, —N(CH₂CH₂)₂N—, or —X—Ar'—Y—(CH₂)ₙ—Z wherein X, Y, and Z are independently a bond, —NR'—, —S—, or —O—, with the proviso that when n=0, then at least one of Y and Z must be a bond and Ar' is 1,2-, 1,3-, or 1,4-phenylene optionally substituted with one, two, or three groups of (C₁–C₅) alkyl, (C₁–C₄) alkoxy, (C₁–C₄) thioalkoxy, halogen, nitro, COOR', CONHR', O(CH₂)ₙCOOR', S(CH₂)ₙCOOR', O(CH₂)ₙCONHR', or S(CH₂)ₙCONHR', with the proviso that when Alk¹ is a bond, Sp¹ is a bond;

n is an integer from 0 to 5;

R' is a branched or unbranched (C₁–C₅) chain optionally substituted by one or two groups of —OH, (C₁–C₄) alkoxy, (C₁–C₄) thioalkoxy, halogen, nitro, (C₁–C₃) dialkylamino, or (C₁–C₃) trialkylammonium—A⁻ where A⁻ is a pharmaceutically acceptable anion completing a salt;

Ar is 1,2-, 1,3-, or 1,4-phenylene optionally substituted with one, two, or three groups of (C₁–C₆) alkyl, ($C_1$–$C_5$) alkoxy, ($C_1$–$C_4$) thioalkoxy, halogen, nitro, or COOR', CONHR', O($CH_2$)$_n$COOR', S($CH_2$)$_n$COOR', O($CH_2$)$_n$CONHR', or S($CH_2$)$_n$CONHR' wherein n and R' are as hereinbefore defined or a 1,2-, 1,3-, 1,4-, 1,5-, 1,6-, 1,7-, 1,8-, 2,3-, 2,6-, or 2,7-naphthylidene or

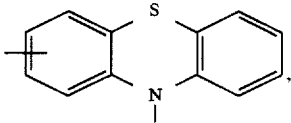

each naphthylidene or phenothiazine optionally substituted with one, two, three, or four groups of ($C_1$–$C_6$) alkyl, ($C_1$–$C_5$) alkoxy, ($C_1$–$C_4$) thioalkoxy, halogen, nitro, or COOR', CONHR', O($CH_2$)$_n$COOR', S($CH_2$)$_n$COOR', O($CH_2$)$_n$CONHR', or S($CH_2$)$_n$CONHR' wherein n and R' are as hereinbefore defined, with the proviso that when Ar is naphthylidene, $Z^1$ is not hydrogen and with the proviso that when Ar in phenothiazine, $Sp^1$ is a bond only connected to nitrogen;

$Sp^2$ is a bond, —S—, or —O—, with the proviso that when $Alk^2$ is a bond, $Sp^2$ is a bond;

$Z^1$ is H, ($C_1$–$C_5$) alkyl, or phenyl optionally substituted with one, two, or three groups of ($C_1$–$C_5$) alkyl, ($C_1$–$C_4$) alkoxy, ($C_1$–$C_4$) thioalkoxy, halogen, nitro, COOR', CONHR', O($CH_2$)$_n$COOR', S($CH_2$)$_n$COOR', O($CH_2$)$_n$CONHR', or S($CH_2$)$_n$CONHR' wherein n and R' are as hereinbefore defined;

$Z^2$ is oxygen; and m is 1, with the proviso that when Ar is unsubstituted 2,6-naphthylene or 1,3- or 1,4-phenylene optionally substituted with one group of ($C_1$–$C_6$) alkyl or ($C_1$–$C_5$) alkoxy and $Alk^2$ is a bond, then $Sp^1$ is not a bond, —O—, or —NHCO—.

DESCRIPTION OF THE DRAWINGS

FIG. 1: DNA and amino acid sequences (SEQ ID NO:1) for h-P67.6 light chain.

FIG. 2: DNA and amino acid sequences (SEQ ID NO:3) for h-P67.6 heavy chain.

BACKGROUND OF THE INVENTION

Figure 3:
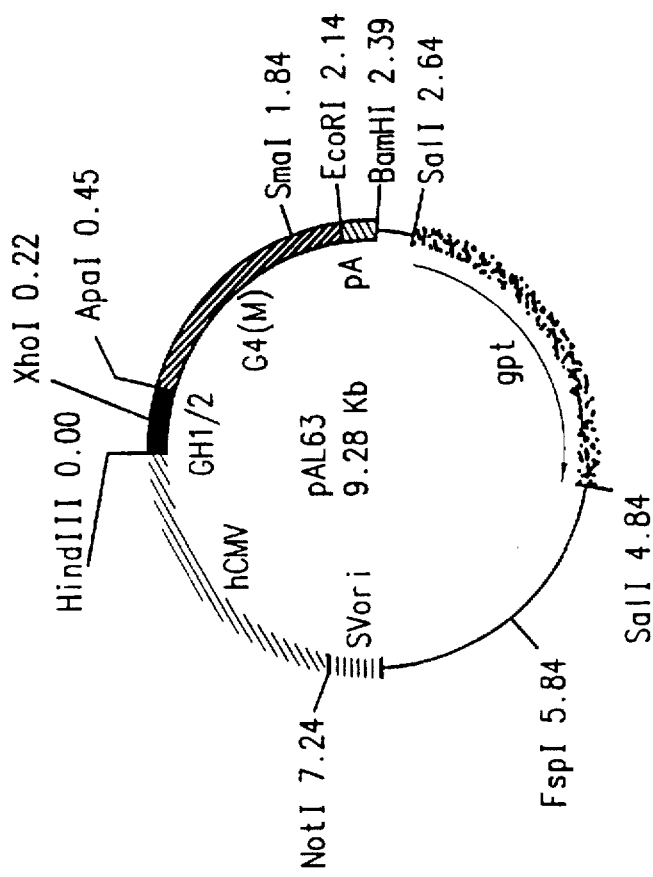
FIG. 3: Plasmid for h-P67.6 heavy chain expression.

Since the discovery of methodology for producing monoclonal antibodies was published in the 1970's (G. Köhler and C. Milstein, "Nature" 256, 495 (1975)), numerous attempts have been made to use these proteins to achieve selective targeting of antitumor agents to tumors. (E.g., see T. Ghose and A. H. Blair, "CRC Critical Rev. Drug Carrier Systems" 3, 263 (1987), G. A. Koppel, "Bioconjugate Chem." 1, 13 (1990), and J. Upeslacis and L. Hinman, "Ann. Rep. Med. Chem." 23, 151 (1988).) Although progress continues to be made in this field, most classical antitumor agents produce antibody conjugates which are relatively ineffective for a variety of reasons. Among the reasons for this ineffectiveness is the lack of potency of the chemotherapeutic agent and its poor utilization due to the lack of efficient release of the drug at its site of action.

The potent family of antibacterial and antitumor agents, known collectively as the calicheamicins or the LL-E33288 complex, are described and claimed in U.S. Pat. No. 4,970,198 (1990). The most potent of the agents is designated $\gamma_1^I$, which is herein referred to simply as gamma. The dihydro derivatives of these compounds are described in U.S. Pat. No. 5,037,651 (1991) and the N-acylated derivatives are described in U.S. Pat. No. 5,079,233 (1992). Related compounds which are also useful in this invention include the esperamicins which are described and claimed in U.S. Pat. No. 4,675,187 (1987); U.S. Pat. Nos. 4,539,203; 4,555,162; and 4,873,206. All of these compounds contain a methyltrisulfide that can be reacted with appropriate thiols to form disulfides, at the same time introducing a functional group such as a hydrazide or similar nucleophile. Examples of this reaction with the calicheamicins are given in U.S. Pat. No. 5,053,394 which also discloses targeted forms of the calicheamicins. All information in the above-mentioned patent citations is incorporated herein by reference. Two compounds which are useful for the synthesis of conjugates with carrier molecules, as disclosed and claimed in U.S. Pat. No. 5,053,394, are shown in Table 1.

TABLE 1

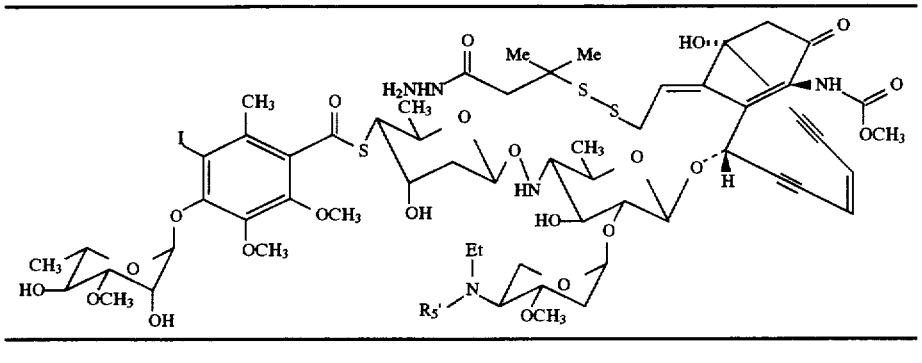

R₅' = H  gamma dimethyl hydrazide
R₅' = Ac  N-acetyl gamma dimethyl hydrazide

Included as carrier molecules in U.S. Pat. No. 5,053,394 are steroids, growth factors, antibodies, antibody fragments, and their genetically or enzymatically engineered counterparts, hereinafter referred to singularly or as a group as carrier. The essential property of the carrier is its ability to recognize an antigen or receptor associated with an undesired cell line. Examples of carriers are given in U.S. Pat. No. 5,053,394, and such carriers are also appropriate in the present invention. Antibody carriers can be from almost any mammalian species (eg. mouse, human, dog, etc.) and can be produced by various methods (eg. murine antibodies via hybridomas, human antibodies via hybridomas from transgenetic mice, etc).

Specific examples of carriers which are exemplified herein are the antibodies P67.6, A33, CT-M-01 and the "anti-Tac" antibody of Waldman. These antibodies are used here in two forms: a murine form, designated by an "m" (e.g., m-P67.6), and a genetically engineered, humanized form, designated by an "h" (e.g., h-P67.6) whenever appropriate. The basic technology for humanization is disclosed by Winter in U.S. Pat. No. 5,225,539 (1993) and by Adair in WO 91/09967 (1991). m-P67.6 is disclosed in I. D. Bernstein et al., "J. Clin. Invest." 79, 1153 (1987) and recognizes the CD33 antigen which is prevalent on certain human myeloid tumors, especially acute non-lymphocytic leukemia (ANLL).

Figure 1:
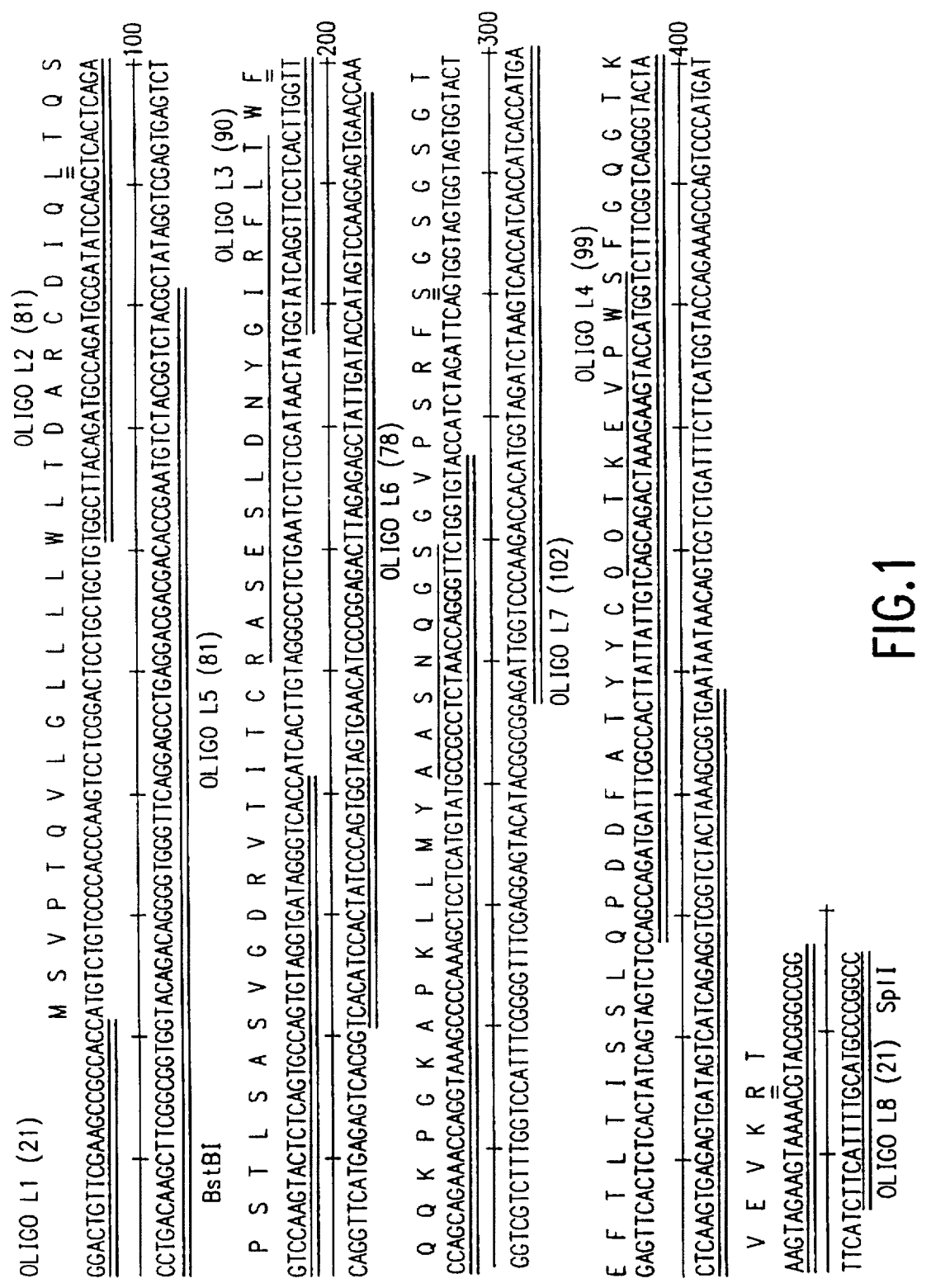
Figure 2:
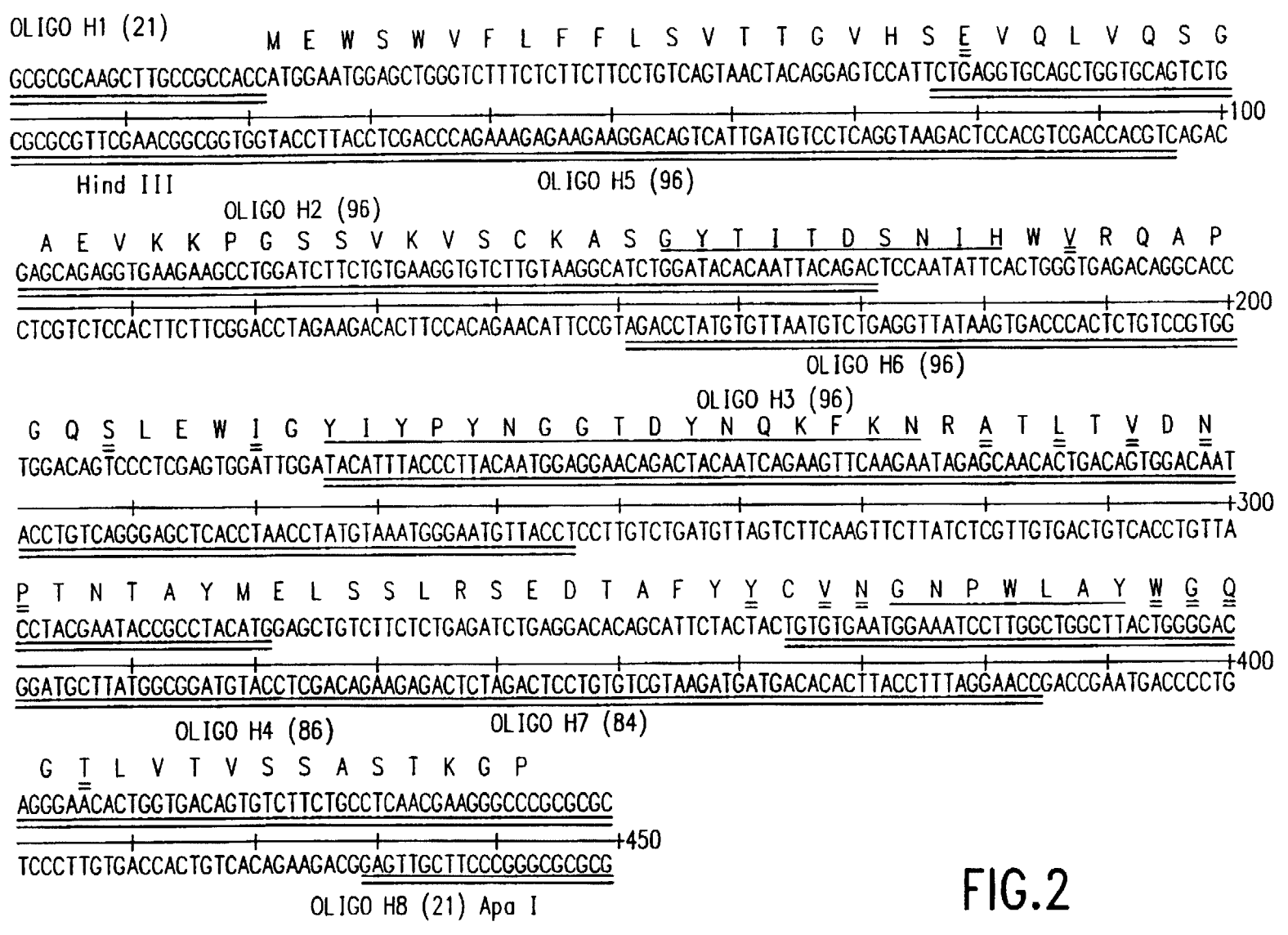

FIG. 1 and FIG. 2 show the DNA coding and predicted amino acid sequences of the variable regions of one particular h-P67.6 that is particularly suitable for use in the present invention. The framework for this antibody is the EU framework for human IgG₄ shown in Gottlieb et al., "Biochemistry: 9, 3115 and 3161 (1970) and the amino acid sequences set forth in FIG. 1 (SEQ ID NO: 2) and FIG. 2 (SEQ ID NO: 4). The antibody was prepared using the general strategy described in WO 91/09967.

Figure 4:
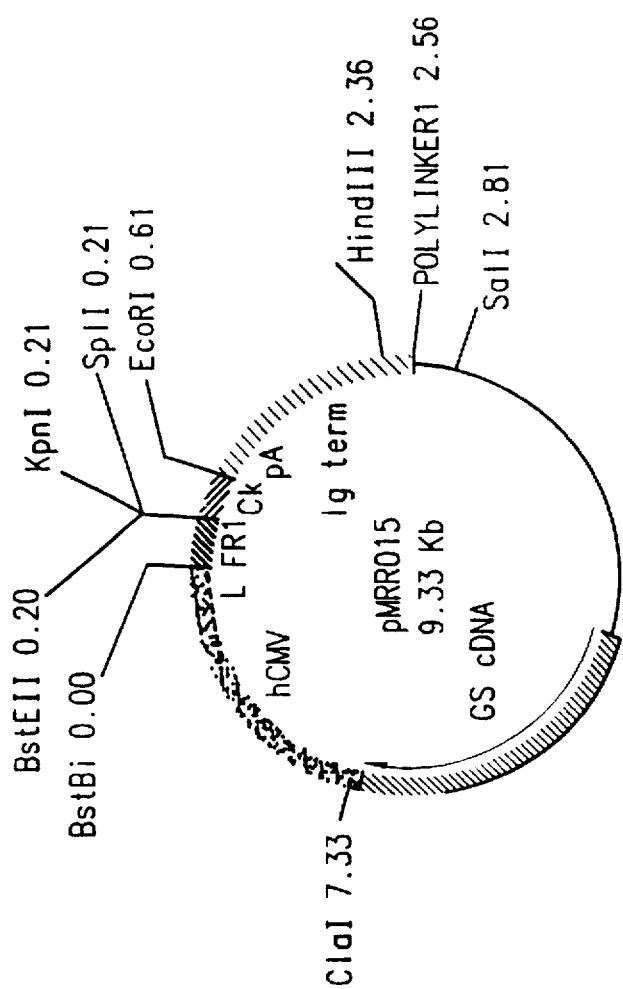
FIG. 4: Plasmid for insertion of h-P67.6 heavy chain.
Figure 5:
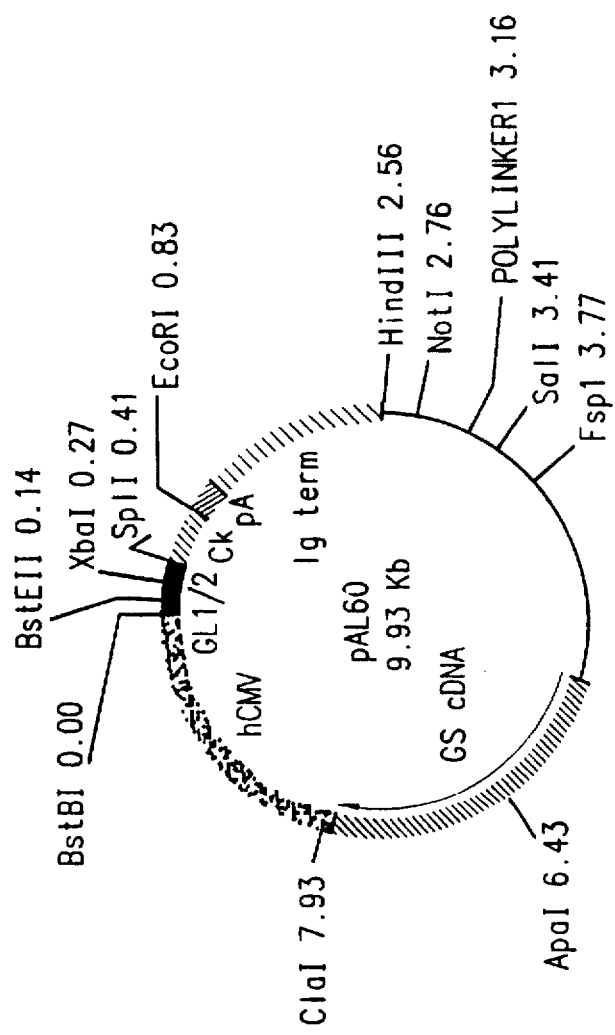
FIG. 5: Plasmid for h-P67.6 light chain expression.

With reference to FIGS. 1 and 2, the overlapping oligonucleotides that were synthesized (Oligo L1 through L8) are shown with double underlines, and the PCR assembly procedure (cf. WO 92/01059) was applied to these sequences. The CDR regions of the protein are designated with single underlines and other amino acids that were taken from the murine sequences are shown with a double underline. The restriction sites that were used to splice the sequences into plasmids are indicated at the beginning and end of the sequences. The variable portion of the heavy chain was cloned into plasmid pMRR14 (WO 93/06231) to give the plasmid designated pAL63 (FIG. 3) and the variable portion of the light chain was cloned into plasmid pMRR15 (FIG. 4) to give pAL60 (FIG. 5). Plasmids pMRR14 and pMRR15 contained the constant regions of the heavy and light chains, respectively, and therefore pAL63 and pAL60 contained complete sequences for the P67.6 heavy and light chains. The plasmids were cotransfected into CHO-L761 cells to generate a h-P67.6 producing line from which the h-P67.6 was purified by standard methods. The resultant h-P67.6 bound to HL60 cells in competition with murine antibody with about a 50% loss in immunoaffinity. This binding was inhibited by pre-incubation with soluble CD33 antigen.

The antibody m-CT-M-01 is disclosed in E.P. 86 401482.4/0208615 and recognizes the polyepithelial mucin (PEM) antigen present on many human solid tumors, particularly breast, lung, and ovarian. The humanized version of this antibody, h-CT-M-01, is described in WO 93/06231 (1993). The antibody m-A33 is disclosed in U.S. patent application Ser. Nos. 5,160,723 and 5,431,897 and is a murine antibody which recognizes a glycoprotein antigen present on colon cancer cells. The humanized version of this antibody, h-A33, is disclosed in UK Patent Application 9,315,249.4.

Anti-Tac is disclosed in T. A. Waldman et al., "J. Immunol." 126, 1393 (1981) and is a murine antibody reactive with the IL-2 receptor that is found on activated and functionally mature T cells, including abnormally activated leukemia cells.

The two basic types of conjugates disclosed in U.S. Pat. No. 5,053,394 are those which are attached to lysine residues of the antibody and those which are attached to the oxidized carbohydrate residues using the method taught in U.S. Pat. No. 4,671,958. Lysine attachment as it is disclosed in U.S. Pat No. 5,053,394 produces conjugates which are stable to hydrolysis under normal physiological conditions. The carbohydrate-based conjugates, which involve the formation of a hydrazone from a hydrazide or similar derivative, are hydrolytically unstable under certain conditions, and that is in many cases an advantage. Some instability is often needed to allow release of the drug once the conjugate has been internalized into the target cell, but a certain degree of stability is important to prevent premature release of the drug from the antibody. However, these carbohydrate-based conjugates suffer from various drawbacks. First, it is necessary to use periodate to generate aldehydes from the carbohydrate residues of the antibody. Antibodies contain cysteines, cystines, methionines, tryptophans, or tyrosines residues which are necessary for proper functioning of the antibody. However, these same amino acids can be sensitive to periodate oxidation, and if such oxidation takes place to an amino acid which either is part of the antigen binding site of the antibody or a structurally important region near the antigen binding site, its immunoaffinity can be significantly diminished. A second drawback of using the carbohydrates for conjugation is the variability of the hydrazones and related structures that are generated from the naturally-occurring sugars and the hydrazide derivative. Not only are the hydrazones subject to different rates of hydrolysis due to differences in their local structure, but other structures, such as hydrated species, piperadines, etc. can also be generated. Any one conjugate may contain structures that are either too stable or to labile for optimum activity.

Limited examples of how too combine some of the properties of the carbohydrate-based conjugates and the lysine-based conjugates have appeared using other less potent classes of anticancer agents. Cullinan in U.S. Pat. Nos. 5,006,652 and 5,094,849 teaches that certain bifunctional compounds containing both carboxylic acid and aldehyde or keto functionality can be used as spacers between the lysines of antibodies and hydrazide derivatives of the Vinca alkaloids, while Johnson in U.S. Pat. Nos. 5,028,697 and 5,144,012 teaches similar art for methotrexate analogs. Sinam et al. also disclose similar constructs in WO Pat. No. 90/03401. In none of these cases is it demonstrated that this method is useful for preparing conjugates of the methyltrisulfide antitumor antibiotics, especially the calicheamicins or esperamicins. The cited patents do not demonstrate that these constructs made with either the Vinca alkaloids, the methotrexate analogs, or other agents are superior in their biological profile to conjugates made using lysine-based or carbohydrate-based conjugates.

The present invention describes a series of conjugates prepared from the potent methyltrisulfide antitumor antibiotics made with an improved linker system that gives conjugates which in many cases are vastly superior biologically to conjugates of the same drugs made by other methods.

DETAILED DESCRIPTION OF THE INVENTION

The conjugates of this invention use linkers that can be added to a derivative of a drug, particularly hydrazides and related nucleophiles, prepared from the methyltrisulfide containing antitumor antibiotics. The linkers require a carbonyl group on one end for formation of a Schiff's base, particularly a hydrazone, and a carboxylic acid on the other end. The carboxylic acid can be activated and subsequently reacted with the lysines of an antibody or other targeting protein or with an amine, alcohol, or other appropriate nucleophile on other targeting agents which have been chosen for their ability to target undesired cell populations. These constructs, which for antibodies contain elements of both the lysine-based conjugates and the carbohydrate-based conjugates, not only overcome the disadvantages of previously disclosed constructs, but have the additional advantage that they can be fine-tuned by varying the structure of the linker to "design in" the optimum amount of hydrolytic stability/instability. This can result in maximum toxicity to the target cells with minimal toxicity to the non-target cells. The optimum hydrazone stability/instability is not necessarily the same for each drug and targeting agent combination.

The method of constructing the conjugates described in this patent produces conjugates of the methyltrisulfide antitumor antibiotics which are unexpectedly stable relative to the carbohydrate based conjugates without loss of activity. In some cases, the conjugates are 100 times more potent than the corresponding conjugates made by the carbohydrate-based method and, in addition, show reduced cytotoxicity against non-target cell lines. This results in conjugates with up to 10,000-fold selectivity between target and non-target cell lines.

The linkers required for the construction of these conjugates can be represented by the following formula:

$Alk^1$ and $Alk^2$ are independently a bond or branched or unbranched ($C_1$–$C_{10}$) alkylene chain. $Sp^1$ is a bond, —S—, —O—, —CONH—, —NHCO—, —NR'—, —N(CH$_2$CH$_2$)$_2$N—, or —X—Ar'—Y—(CH$_2$)$_n$—Z wherein n is an integer from 0 to 5, X, Y, and Z are independently a bond, —NR'—, —S—, or —O—, and Ar' is 1,2-, 1,3-, or 1,4-phenylene optionally substituted with one, two, or three groups of ($C_1$–$C_5$) alkyl, ($C_1$–$C_4$) alkoxy, ($C_1$–$C_4$) thioalkoxy, halogen, nitro, COOR', CONHR', O(CH$_2$)$_n$COOR', S(CH$_2$)$_n$COOR', O(CH$_2$)$_n$CONHR', or S(CH$_2$)$_n$CONHR' wherein n is as hereinbefore defined, with the proviso that when $Alk^1$ is a bond, $Sp^1$ is also a bond. R' is a branched or unbranched ($C_1$–$C_5$) chain optionally substituted by one or two groups of —OH, ($C_1$–$C_4$) alkoxy, ($C_1$–$C_4$) thioalkoxy, halogen, nitro, ($C_1$–$C_3$) dialkylamino, or ($C_1$–$C_3$) trialkylammonium—A$^-$ where A$^-$ is a pharmaceutically acceptable anion completing a salt. $Sp^2$ is a bond, —S—, or —O—, with the proviso that when $Alk^2$ is a bond, $Sp^2$ is also a bond. $Z^3$ is a hydroxyl group, and m is 1.

The groups $Alk^1$, $Sp^1$, $Alk^2$ and $Sp^2$ in combination, as well as the group Ar discussed below, allow for spacing of the carbonyl group from the carboxylic acid. Furthermore, $Alk^1$ and $Sp^1$ can influence the reactivity of the carboxyl group both during and after it has been activated. When $Alk^2$ and $Sp^2$ together are a bond, the $Sp^1$ group also influences the reactivity of the carbonyl group on the other end of the linker and the stability of the product formed from reactions at that carbonyl. The group R' can be used to influence the solubility and other physiochemical properties of these compounds. A preferred embodiment for $Alk^1$ is ($C_2$–$C_5$) alkylene, and for $Sp^1$ is an oxygen atom. A preferred embodiment for the groups $Alk^2$ and $Sp^2$ together is a bond.

With reference to the structure shown above, the group $Z^2$ is an oxygen atom. The group $Z^1$ is H, ($C_1$–$C_5$) alkyl, or phenyl optionally substituted with one, two, or three groups of ($C_1$–$C_5$) alkyl, ($C_1$–$C_4$) alkoxy, ($C_1$–$C_4$) thioalkoxy, halogen, nitro, COOR', CONHR', O(CH$_2$)$_n$COOR', S(CH$_2$)$_n$COOR', O(CH$_2$)$_n$CONHR', or S(CH$_2$)$_n$CONHR' wherein n and R' are as hereinbefore defined. The group $Z^1$ has a pronounced effect on the reactivity of the carbonyl group and on the stability of the products formed from reactions at the carbonyl. When $Z^1$ is aryl and the product is, for example, a hydrazone, the hydrazone is relatively stable; when $Z^1$ is hydrogen, then an intermediate level of stability is obtained, and when $Z^1$ is ($C_1$–$C_6$) alkyl, relatively less stable hydrazones are formed. As stated earlier, stability is important to prevent premature release of the drug from the antibody, but some instability is needed to allow release of the drug once the conjugate has been internalized into target cells. A preferred embodiment for the $Z^1$ group is ($C_1$ to $C_3$).

The group Ar is 1,2-, 1,3-, or 1,4-phenylene optionally substituted with one, two, or three groups of ($C_1$–$C_6$) alkyl, ($C_1$–$C_5$) alkoxy, ($C_1$–$C_4$) thioalkoxy, halogen, nitro, COOR', CONHR', O(CH$_2$)$_n$COOR', S(CH$_2$)$_n$COOR', O(CH$_2$)$_n$ CONHR', or S(CH$_2$)$_n$CONHR' wherein n and R' are as hereinbefore defined or a 1,2-, 1,3-, 1,4-, 1,5-, 1,6-, 1,7-, 1,8-, 2,3-, 2,6-, or 2,7-naphthylidene or

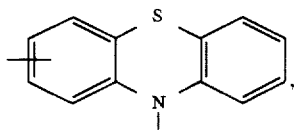

wherein Sp$^1$ a bond only connected to the nitrogen of the phenothiazine, each optionally substituted with one, two, three, or four groups of (C$_1$–C$_6$) alkyl, (C$_1$–C$_5$) alkoxy, (C$_1$–C$_4$) thioalkoxy, halogen, nitro, or COOR', CONHR', O(CH$_2$)$_n$COOR', S(CH$_2$)$_n$COOR', O(CH$_2$)$_n$CONHR', or S(CH$_2$)$_n$CONHR' wherein n and R' are as hereinbefore defined;

The choice of Ar has a significant influence on the stability of the products derived from the carbonyl when Alk$^2$ and Sp$^2$ are together a bond. Both the relative position of Sp$^1$ and Sp$^2$ as well as the presence of additional substituents on Ar can be used to fine-tune the hydrolytic behavior of the product formed from the carbonyl. A preferred embodiment for Ar is 1,2-, 1,3-, or 1,4-phenylene, or 1,2-, 1,3-, 1,4-, 1,5-, 1,6-, 1,7-, 1,8-, 2,3-, 2,6-, or 2,7-naphthylidene.

The structures of specific examples of linkers which are useful in the present invention are as follows:

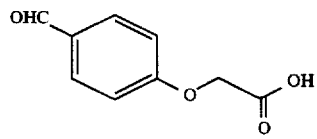

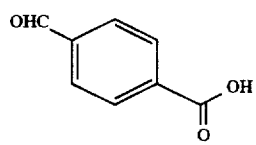

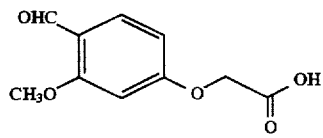

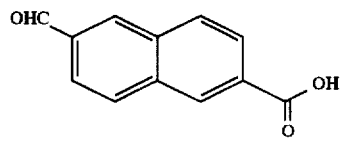

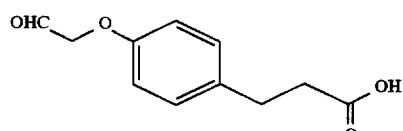

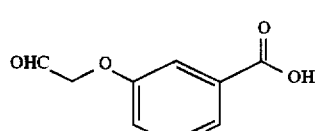

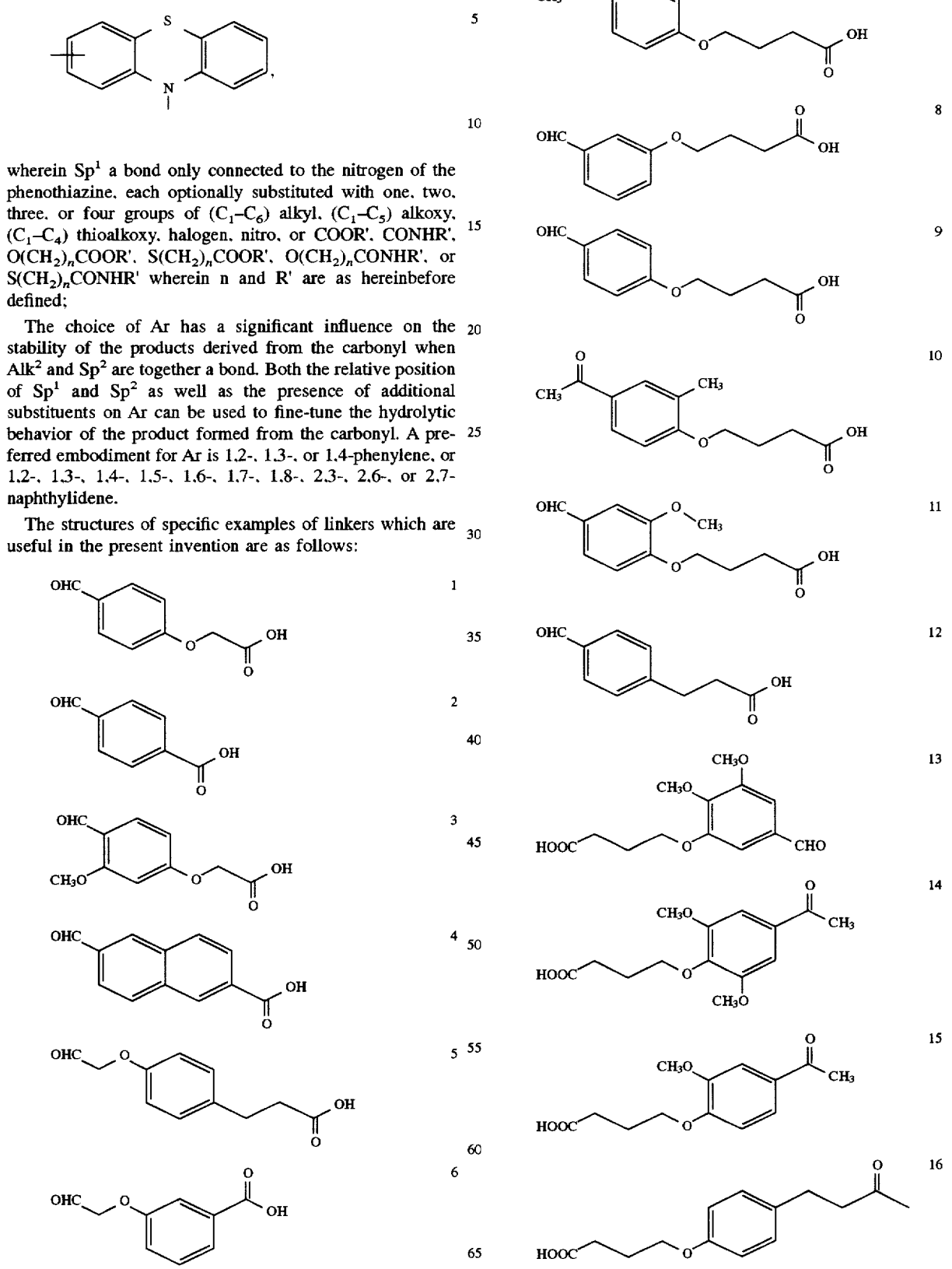

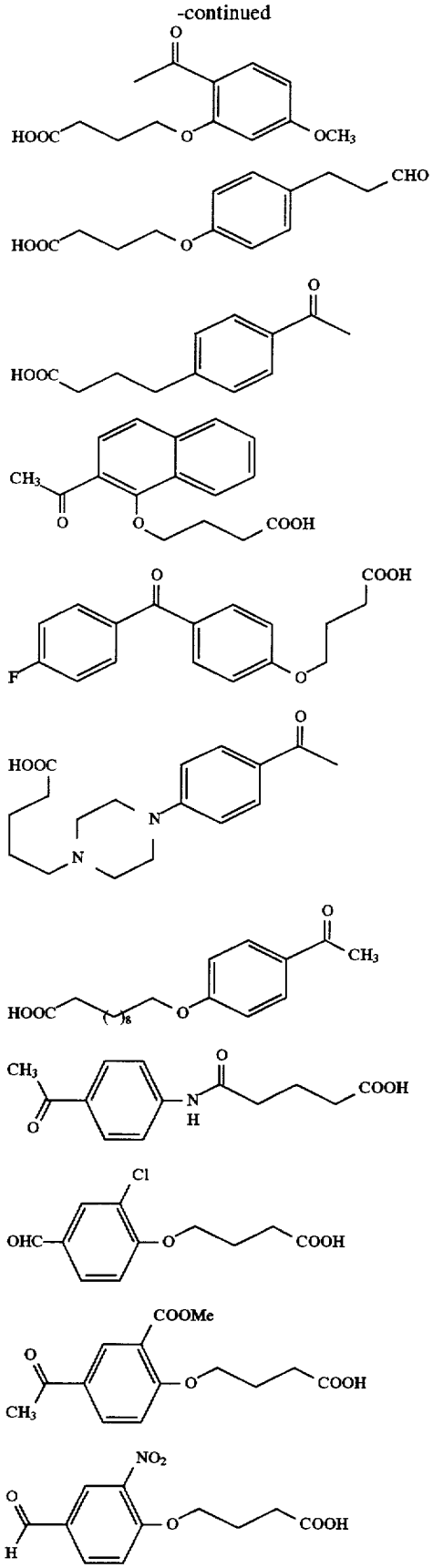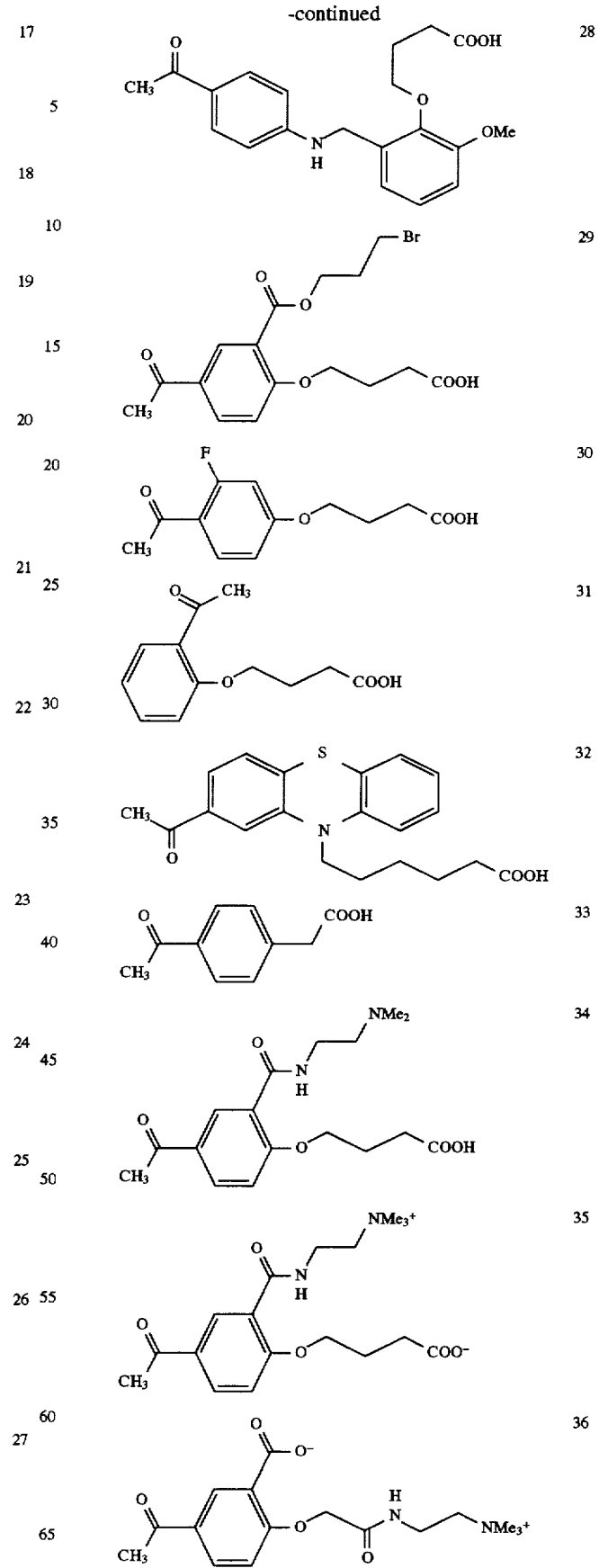

Only a few of the more simple of these linkers are commercially available, i.e., linkers 1, 2, 3, 19, 23, 24, and 33. Linker 20 is listed by the Chemical Abstract Services with registry number 5084-45-7. Many linkers which contain aryl ethers as a part of their structure, such as 7, 8, 10, 13, 14, 15, 16, 17, 20, 21, 25, 28, 30, and 31, can be made by alkylating a phenolic ketone with an electrophile, such as ethyl 4-bromo-butyrate, using an appropriate base, such as potassium carbonate, in an appropriate solvent, such as N,N-dimethyl formamide, and then converting the ester into the required carboxylic acid by hydrolysis with, for example, sodium hydroxide or potassium carbonate in aqueous methanol. This strategy can also be used with linkers such as 5, 6, 9, 11, 18, or 27, where the carbonyl is carried through the initial steps of the preparation in a masked form, such as an olefin or an alcohol. The carbonyl can then be generated later, as described in the examples, by oxidation with ozone or pyridinium chlorochromate, resp. This procedure is especially valuable when a more reactive carbonyl is present in the final linker.

When necessary, the required carboxylic acid can be introduced in a masked form as in the preparation of linker 26. In this case the phenol is alkylated with 5-bromo-1-pentene and the acid is liberated from the olefin by reaction with ozone followed by pyridinium chlorochromate oxidation. Linkers such as 22 or 32 can be made by alkylating an appropriate secondary amine (a piperazine or phenothiazine derivative, resp.) with an appropriate electrophile and then exposing the required carboxylic acid in a later step, similar to the previously mentioned strategies. Linker 12 was made by reduction of the corresponding cinnamate with hydrogen. Although this reaction gave a relatively impure product, the crude mixture was useful for conversion to the required hydrazone because none of the by-products contained aldehyde groups. Structures with more elaborate substituents, such as linkers 33, 34, 35, or 36, can be made from simpler structures by, for example, reacting an ester with an appropriate nucleophile or by quaternizing an amine with an electrophile, such as methyl iodide.

The linkers defined above can be used to form conjugates as follows:

Scheme 1

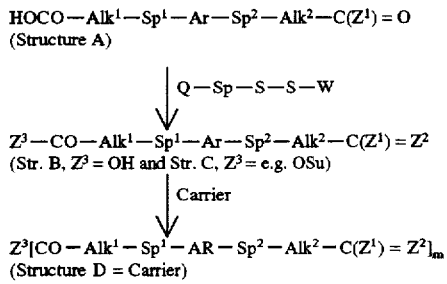

With reference to Scheme 1 above, the linker of structure A, wherein $Z^1$, $Alk^1$, $Sp^1$, $Ar$, $Sp^2$, and $Alk^2$ are as hereinbefore defined, is condensed with a compound of structure Q-Sp-S-S-W, which itself is derived from a methyltrithio antitumor antibiotic, and wherein W is

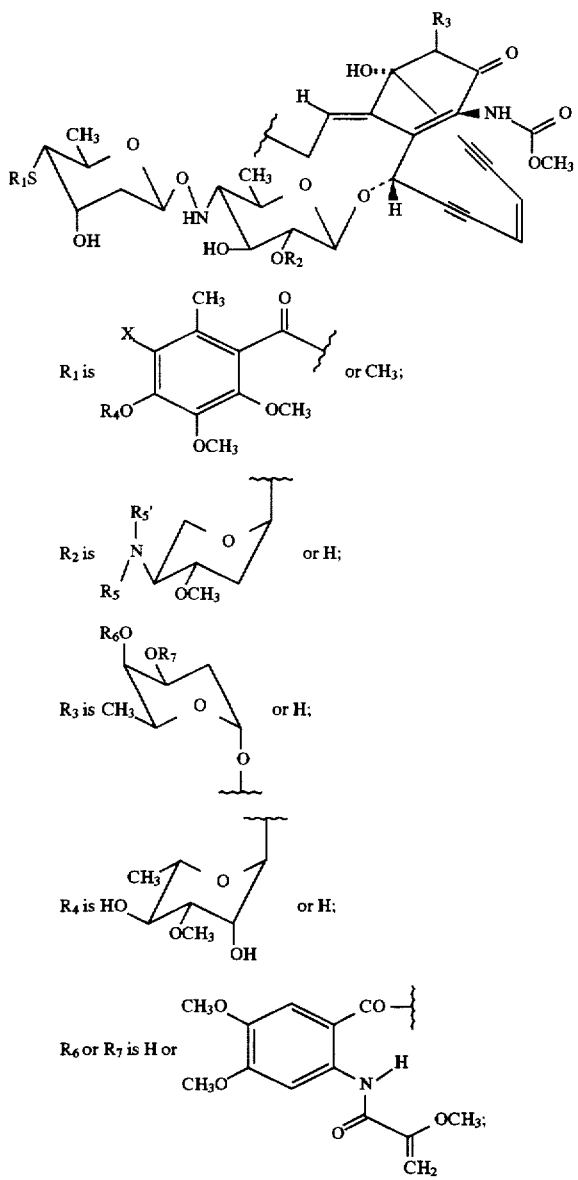

$R_5$ is —$CH_3$, —$C_2H_5$, or —$CH(CH_3)_2$; X is an iodine or bromine atom; $R_5'$ is a hydrogen or the group RCO, wherein R is hydrogen, branched or unbranched ($C_{1-10}$) alkyl or ($C_1$–$C_{10}$) alkylene group, a ($C_6$–$C_{11}$) aryl group, a ($C_6$–$C_{11}$) aryl-alkyl ($C_1$–$C_5$) group, or a heteroaryl or heteroaryl-alkyl ($C_1$–$C_5$) group wherein heteroaryl is defined as 2- or 3-furyl, 2- or 3-thienyl, 2- or 3-(N-methylpyrrolyl), 2-, 3-, or 4-pyridinyl, 2-, 4-, or 5-(N-methylimidazolyl), 2-, 4-, or 5-oxazolyl, 2-, 3-, 5-, or 6-pyrimidinyl, 2-, 3-, 4-, 5-, 6-, 7-, or 8-quinolyl, or 1-, 3-, 4-, 5-, 6-, 7-, or 8-isoquinolyl, all aryl and heteroaryl optionally substituted by one or more hydroxy, amino, carboxy, halo, nitro, lower ($C_1$–$C_3$) alkoxy, or lower ($C_1$–$C_5$) thioalkoxy groups; Sp is a straight or branched-chain divalent or trivalent ($C_1$–$C_{18}$) radical, divalent or trivalent aryl or heteroaryl radical, divalent or trivalent ($C_3$–$C_{18}$) cycloalkyl or heterocycloalkyl radical, divalent or trivalent aryl- or heteroaryl-alkyl ($C_1$–$C_{18}$) radical, divalent or trivalent cycloalkyl- or heterocycloalkyl-alkyl ($C_1$–$C_{18}$) radical or divalent or trivalent ($C_2$–$C_{18}$) unsaturated alkyl radical, wherein heteroaryl is furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein if Sp is a trivalent radical, it can be additionally substituted by lower ($C_1$–$C_5$) dialkylamino, lower ($C_1$–$C_5$) alkoxy, hydroxy, or lower ($C_1$–$C_5$) alkylthio groups; and Q is $H_2NHNCO$—, $H_2NHNCS$—, $H_2NHNCONH$—, $H_2NHNCSNH$—, or $H_2NO$—, to produce a compound of structure B, wherein $Z^1$, Alk$^1$, Sp$^1$, Ar, Sp$^2$, and Alk$^2$ are as hereinbefore defined, $Z^2$ is Q-Sp-S-S-W, wherein Sp and W are as herein above defined, Q is =NHNCO—, =NHNCS—, =NHNCONH—, =NHNCSNH—, or =NO—, and $Z^3$ is —OH.

The condensation can be run in most compatible organic solvents, but is particularly efficient in alcoholic solvents such as methanol or ethanol. This condensation reaction is acid catalyzed. The carboxylic acid in the linkers themselves is sufficient in many cases to catalyze this reaction, but adding a compatible acid catalyst, such as about 5% acetic acid, helps improve the rate of reaction in many cases. The temperature of this reaction can be from about ambient temperature to the reflux temperature of the solvent. The products are isolated in pure form by removing the volatile solvents and purifying the mixture by chromatography on a suitable medium such as BIOSIL A™, a modified silica gel available from Bio-Rad. It should be understood that the products of structure B, as well as the products from the further transformation of these compounds, exist as easily-interconverted syn and anti isomers at the locus defined as Q, and that these products can exist in different hydrated forms, depending on the exact conditions of solvent and the pH at which these compounds are examined. Such differing physical forms are also included within the scope of this patent.

The carboxylic acid of structure B ($Z^3$=—OH) is next converted to an activated ester in preparation for conjugation of these intermediates with carrier molecules. Such transformations convert $Z^3$ (structure B) to halogen, —$N_3$,

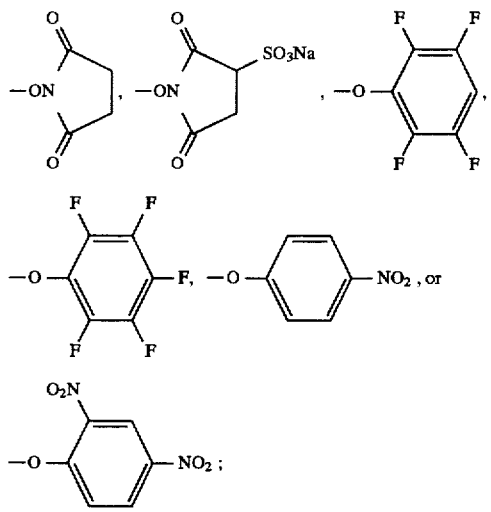

For example, reaction of the carboxyl form of structure B ($Z^3$=—OH) with a coupling agent, such as 1,3-dicyclohexylcarbodiimide or 1-(3-dimethylaminopropyl)-3-ethylcarbodiimide hydrochloride, and N-hydroxysuccinimide or other comparable carboxyl-activating group in an inert solvent, such as N,N-dimethylformamide, tetrahydrofuran, or acetonitrile, leads to the formation of an activated ester, such as the N-hydroxysuccinimide ester described herein. These active esters can be isolated in pure form by removal of the volatile solvents and chromatography on an appropriate medium, such as BIOSIL A™. Alternately, the coupling reaction can be quenched with a polymeric carboxylic acid, filtered, and stripped of organic solvents, and the crude product can be used in the following step without further purification. This is especially useful if the active ester is difficult to handle, such as when

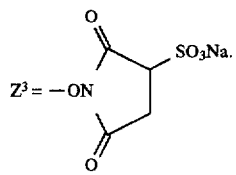

The final step in the construction of the conjugates of this patent involves the reaction of an activated ester (structure C) with a targeting molecule, as shown in Scheme 1. This produces a compound of structure D, wherein $Z^1$, $Z^2$, Alk$^1$, Sp$^1$, Ar, Sp$^2$, and Alk$^2$ are as hereinbefore defined, m is 0.1 to 15, and $Z^3$ is a protein such as a growth factor or a mono- or polyclonal antibody, their antigen-recognizing fragments, or their chemically or genetically manipulated counterparts or a steroid, wherein a covalent bond to a protein is an amide formed from reaction with lysine side chains and the covalent bond to a steroid is an amide or an ester.

This conjugation reaction can be carried out in various appropriate buffers, such as borate, phosphate, or HEPES at slightly basic pH (pH –7.4 to 8.5). The final construct can then be purified by appropriate methods, such as gel-exclusion chromatography, to remove unattached drug and aggregates to yield monomeric conjugates. This sequence of steps constitutes Method A as described in greater detail in the Examples section of this patent.

Alternative methods for constructing the conjugates of Scheme 1 are also contemplated as shown in Scheme 2.

Scheme 2

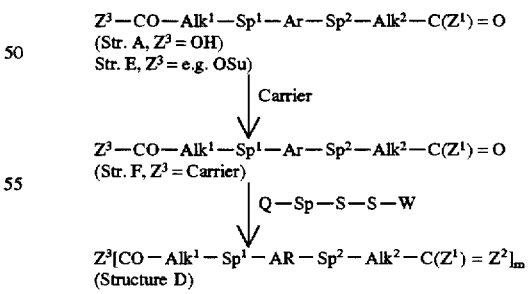

For example, the linker (structure A as defined above) can be converted to an active ester and reacted with the targeting molecule prior to the reaction with the drug. Such manipulations convert structure A into structure E, wherein $Z^1$, Alk$^1$, Sp$^1$, Ar, Sp$^2$, and Alk$^2$ are as hereinbefore defined, $Z^2$ is an oxygen atom, and $Z^3$ is halogen, —$N_3$,

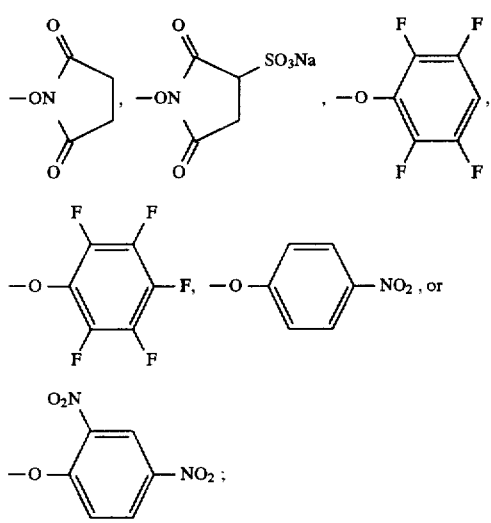

The activated ester is then reacted with the carrier to produce structure F, wherein $Z^1$, $Alk^1$, $Sp^1$, Ar, $Sp^2$, and $Alk^2$ are as hereinbefore defined, $Z^2$ is an oxygen atom, m is about 1 to about 20, and $Z^3$ is a protein selected from mono- and polyclonal antibodies, their antigen-recognizing fragments, and their chemically or genetically manipulated counterparts and growth factors and their chemically or genetically manipulated counterparts, wherein a covalent bond to the protein is an amide formed from reaction with lysine side chains, or a steroid, wherein the covalent bond to the steroid is an amide or an ester;

Once the targeting molecule has been modified with the linker, it can be reacted with a compound of structure Q-Sp-S-S-W, which itself is derived from a methyltrithio antitumor antibiotic, and wherein W and Sp are as hereinbefore defined, and Q is $H_2NHNCO$—, $H_2NHNCS$—, $H_2NHNCONH$—, $H_2NHNCSNH$—, or $H_2NO$— to produce a compound of Structure D (vida supra).

Figure 6:
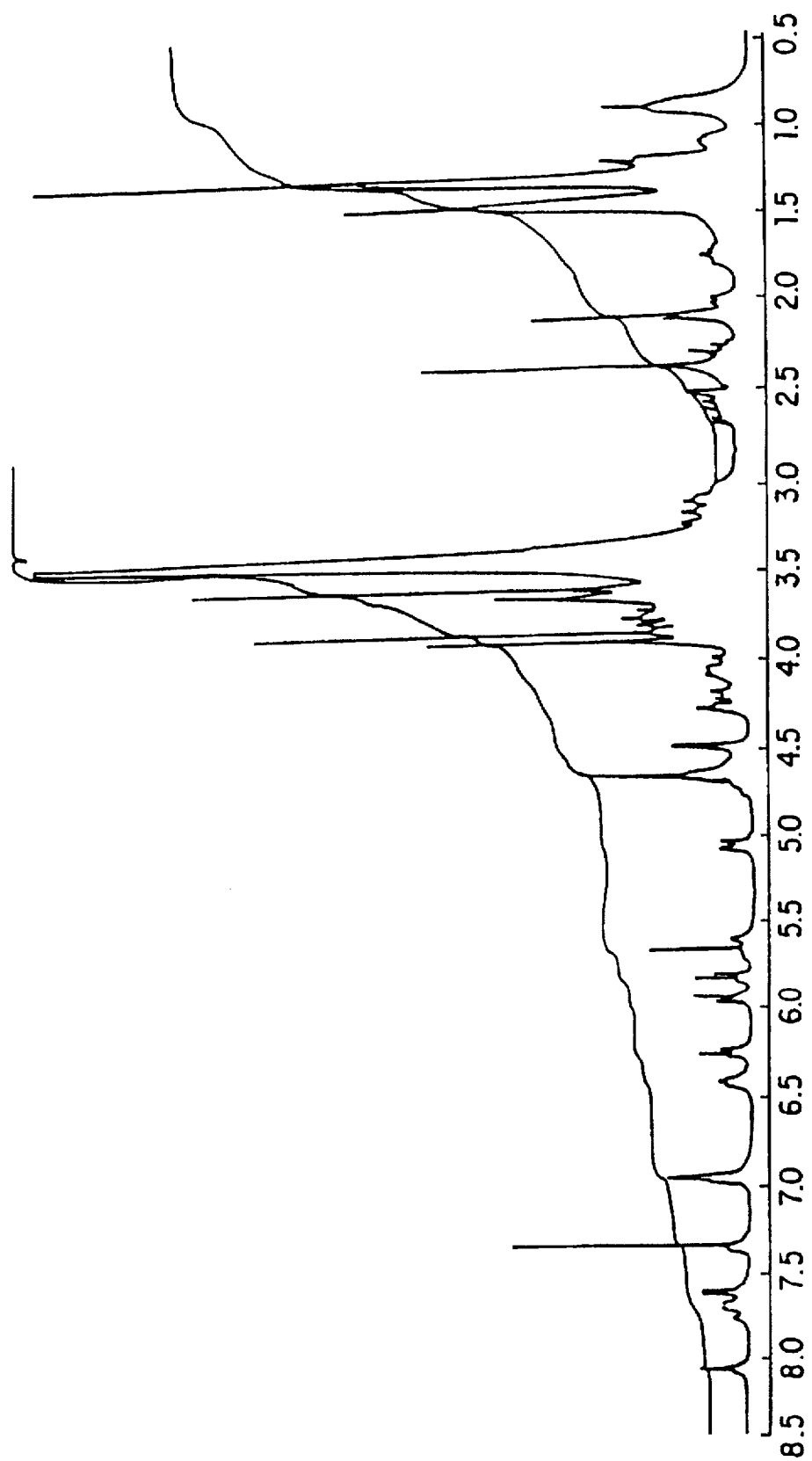
FIG. 6: The proton magnetic resonance spectrum of 4-formylphenoxyacetic acid condensed with Calicheamicin N-acetyl gamma dimethyl hydrazide.

This sequence of steps in Scheme 2 constitutes Method B in the Examples section of this patent. Similar antibody-carbonyl constructs are covered in U.S. Pat. No. 5,144,012 mentioned above. Most of the linkers exemplified herein are new and offer the advantage that a much broader range of structural types and hence a broader range of stabilities is demonstrated. As a specific example, the acetophenone linkers, which are new to this patent, produced conjugates with better hydrolytic release properties of drug and which are more potent when used with the examples of the antibodies shown here. Specifically, the two conjugates prepared from h-P67.6 using 4-formylbenzenepropanoic acid or 4-acetylbenzenebutanoic acid condensed with calicheamicin N-acetyl gamma hydrazide (the two conjugates only differ by having $Z^1$=—H and $Z^1$=—$CH_3$, respectively, in structure 3 of FIG. 6) gave in vitro $IC_{50}$'s of 1.0 and 0.012 ng/mL, and specificity indices of 950 and 26,000, respectively. Although the acetophenone based linkers are seen to be superior in this case, it is not necessarily easy to predict which linker will be superior for any given targeting agent-drug construct.

BIOLOGICAL CHARACTERIZATION

Assessment of the biological properties of the conjugates included measuring their ability to recognize the antigen on target cell lines, relative to the unmodified antibody, and determining their selectivity and cytotoxic potentials, using the following methods:

IMMUNOAFFINITY ASSAYS

Relative immunoaffinities of conjugates are determined in a competitive binding assay in which varying concentrations of test conjugate are allowed to compete with a fixed amount of the same antibody labeled with $^{125}$I-Bolton Hunter reagent for binding to a fixed number of cells. For m- or h-P67.6, HEL 92.1.7 human erythroleukemia cells [ATCC (American Type Culture Collection) TIB 180] are used at a concentration of $10^7$ cells/mL; for CT-M-01, cell line A2780DDP (E. M. Newman, et al., "Biochem. Pharmacol." 37, 443 (1988)) is used; and for m- or h-A33, cell line COLO 205 (ATCC CCL 222) is used. The concentration of test conjugate required to obtain 50% inhibition of binding of the labeled antibody to target cells is compared with the concentration of a reference preparation of native antibody required for 50% inhibition.

Samples for assay are adjusted to ~300 μg protein/mL in medium and six serial four-fold dilutions of each are prepared in medium (RPMI-1640 containing 5% heat-inactivated fetal calf serum), for a total of seven concentrations of each sample. The reference antibody is diluted in the same way. An aliquot of 0.05 mL of each dilution is transferred to a 12×75 mm plastic tube, and 0.05 mL of labeled reference antibody at 4 μg/mL is added. The tubes are mixed and chilled at 4° C. Then 0.1 mL of chilled cell suspension is added to each tube. All tubes are mixed again, and incubated for 1 hr at 4° C.

Controls to determine maximal binding and non-specific binding are included in each assay. Maximal binding is determined by mixing 0.05 mL of medium, 0.05 mL of $^{125}$I-antibody, and 0.1 mL of cells; non-specific binding is determined by mixing 0.05 mL of 500 μg/mL of native antibody, 0.05 mL of iodinated antibody, and 0.1 mL of cells.

At the end of the incubation, cells are washed twice, by centrifugation and resuspension, with 3 mL of cold PBS each time. The cells are resuspended in 0.5 mL of PBS, transferred to clean tubes, and radioactivity is determined in a gamma-counter.

The percent inhibition of binding is calculated by the following equation:

$$\% I = \{[(cpm_{maxbinding} - cpm_{non\text{-}specific}) - (cpm_{sample} - cpm_{non\text{-}specific})] \div (cpm_{max\ binding} - cpm_{non\text{-}specific})\} \times 100$$

The percent inhibition values are plotted against sample concentrations, and from the resulting curves the sample concentration that gives 50% inhibition of binding ($IC_{50}$) is interpolated. The relative immunoaffinity of each tested conjugate is then determined as follows:

Relative Immunoaffinity=$IC_{50}$(reference)÷$IC_{50}$(sample)

IN VITRO CYTOTOXICITY ASSAY

Cytotoxic activities are determined in an in vitro pulse assay in which varying concentrations of test conjugate are incubated with antigen-positive and antigen-negative cells for 1 hr, then cultured for three days. Viability is assessed by [$^3$H]thymidine incorporation during the final 24 hr of culture. As a measure of potency, the concentration of test conjugate required to inhibit [$^3$H]thymidine incorporation by 50% ($IC_{50}$) is determined from the titration curve. The specificity is determined by comparing $IC_{50}$ values on antigen-positive and antigen-negative cells for P67.6, A33, and m-CT-M-01 or by use of a conjugate of the same drug with the non-targeting antibody P67.6 for h-CT-M-01 conjugates or MOPC-21 for anti-Tac conjugates. MOPC-21 (F. Melchers, "Biochem. J." 119, 765 (1970)) is an antibody which does not recognize any normally occurring, physiologically pertinent antigen.

For P67.6, antigen-positive HL-60 human promyelocytic leukemia cells (ATCC CCL 240) and antigen-negative Raji human Burkitt lymphoma cells (ATCC CCL 86) are used; for A33, antigen-positive COLO 205 cells and antigen-negative Raji cells are used; and for h-CT-M-01, ZR-75-1 cells (ATCC CRL1500) are used. For m-CT-M-01 antigen-positive A2780DDP cells and antigen-negative Raji cells are used, and for h-CT-M-01, ZR-75-1 cells (ATCC CRL1500) are used. Cells are collected by centrifugation, counted, and resuspended in fresh medium (RPMI-1640+5% heat-inactivated fetal calf serum+antibiotics) at a cell concentration of ~$10^6$/mL.

Samples for assay are readjusted to ~1 µg/mL of drug equivalents in medium and five serial ten-fold dilutions of each are prepared in medium, for a total of six concentrations of each sample. In addition, a medium control is included with each sample set, as well as calicheamicin N-acetyl gamma as a drug control. An aliquot of 0.1 mL of cell suspension is added to 17×100 mm plastic tubes containing 0.1 mL of sample; a separate series of tubes is prepared for each cell line. The tubes are loosely capped and incubated for 1 hr at 37° C. in a humidified atmosphere of 5% $CO_2$ in air. At the end of the incubation, cells are washed twice by centrifugation and resuspended with 8 mL of medium each time. Cell pellets are resuspended in 1 mL of medium and plated in triplicate in 96-well microtiter plates at 0.2 mL/well. The plates are incubated for 2 days at 37° C. as above. Then 0.1 mL of medium is removed from each well and replaced with 0.1 mL of fresh medium containing 0.1 µCi of [$^3$H]thymidine. Plates are returned to the incubator for one more day. Plates are frozen and thawed, and cells are harvested on glass fiber filter mats. The amount of [$^3$H]thymidine incorporated is determined by liquid scintillation counting.

The measured cpm of the triplicate cultures of each sample dilution are averaged and the percent inhibition of [$^3$H]thymidine incorporation is calculated by the following equation, where the values for no inhibition and maximal inhibition come from the medium controls, and the highest concentration of calicheamicin N-acetyl gamma, respectively:

$$\% I = \{[(cpm_{no\ inhibition} - cpm_{max\ inhibition}) - (cpm_{sample} - cpm_{max\ inhibition})] \div (cpm_{no\ inhibition} - cpm_{max\ inhibition})\} \times 100$$

The percent inhibition values are plotted against sample concentrations, and from the resulting curves the sample concentration that gives 50% inhibition of [$^3$H]thymidine incorporation ($IC_{50}$) is interpolated. For P67.6, A33, and m-CT-M-01 conjugates, the specificity of a particular conjugate for antigen-positive cells is calculated by taking the ratio of the $IC_{50}$ against non-target cells to the $IC_{50}$ against target cells. The same ratio is calculated for the free drug. Then, to correct for inherent differences in the sensitivities of the two cell lines to the drug, the Specificity Index for each sample is calculated as follows:

Specificity Index = [$IC_{50}$ (sample on antigen neg) + $IC_{50}$ (sample on antigen pos) + [$IC_{50}$ (drug on antigen neg) + $IC_{50}$ (drug on antigen pos)]

For conjugates of Anti-Tac or h-CT-M-01, the Specificity Index is calculated as the ratio of $IC_{50}$'s for the non-targeting conjugate and the targeting conjugate as follows:

Specificity Index=$IC_{50}$(non-targeting conjugate)÷$IC_{50}$(targeting conjugate)

IN VIVO ANTITUMOR ASSAY

Human tumors (either ~$10^7$–$10^8$ cells or 5 to 8 fragments of solid tumors 2 mm$^3$ in size) are implanted subcutaneously into athymic mice (nude mice) and test samples are inoculated intraperitoneally (ip) at several dose levels on a q 4 day×3 schedule, starting 2–3 days after tumor implantation with 5 mice per test group and 10 in the saline control group. Tumor mass is estimated by measuring the tumor length and width once weekly up to 42 days post tumor implantation with a Fowler ultra CAL II electronic caliper and using the formula: mg tumor={Length(mm)×Width(mm)}/2. Tumor growth inhibition is calculated as the ratio of the mean tumor mass of treated animals compared with untreated controls and is expressed as "% T/C". (0% T/C implies no detectable tumor. All control animals routinely develop easily measurable tumor.)

EX VIVO INHIBITION OF COLONY FORMATION

For P67.6 conjugates, human leukemic bone marrow cells which are CD-33 positive are plated in the presence of 2 ng/mL drug equivalents. The number of colonies which form are counted and reported as the percent versus a control which consists of a h-CT-M-01 conjugate which does not recognize the CD-33 antigen. All the data reported were generated with bone marrow from one patient whose leukemic cells had good antigen expression and good response to this general type of treatment.

For anti-Tac, peripheral blood from CML patients was tested. Progenitor cells for cells of the various hematopoietic lineages can be detected by culturing bone marrow cells and blood cells in a semisolid matrix such as methylcellulose and observing the formation of colonies containing mature differentiated cells. There are progenitor cells that proliferate to form colonies of granulocytes or macrophages, or both, called colony-forming units for granulocytes-macrophages (CFU-GM). Some CFU-GM form colonies within seven days (D7 CFU-GM); some require fourteen days for colony formation (D14 CFU-GM) [N. Jacobsen, et al., "Blood" 52: 221, (1978), and Ferrero D et al. "Proc. Natl. Acad. Sci. USA" 80: 4114, (1983)]. Inhibition of the growth of D14 CFU-GM on blood cells treated with anti-Tac was compared to those treated with non-targeting MOPC 21 conjugates. The number of D14 CFU-GM colonies are plotted against sample concentrations, and from the resulting curves the sample concentration that gives 50% inhibition of D14 CFU-GM colony growth is interpolated. Specificity was measured by the ratio of the $IC_{50}$ of the non-targeting conjugate versus the $IC_{50}$ of the targeting conjugate. Normal blood does not produce CFU-GM colonies and normal bone marrow D14 CFU-GM colonies are not inhibited by anti-Tac conjugates.

The invention is further described with the following non-limiting preparations and examples. (Preparations describe the syntheses of compounds useful in this invention but for which there is known prior art. Examples describe the syntheses of compounds which are useful and new to this invention.)

SYNTHESIS OF STRUCTURES A (SCHEME 1 AND SCHEME 2)

Example 1, Compound 5

4-(2-Oxoethoxy)benzenepropanoic acid

4-Hydroxybenzenepropanoic acid (500 mg, 3.01 mmol) is allowed to react with 910 mg (7.52 mmol) of allyl bromide by the same procedure described in Example 2 to give 610 mg (82%) of 2-propenyl-4-(2-propenyloxy) benzenepropanoic ester as a colorless oil. The product is utilized in the next reaction without further purification. The $^1$H NMR (300 MHz, CDCl$_3$) is consistent with the desired product; IR (neat) 3450, 1740, 1650, 1610, 1510 cm$^{-1}$; MS (CI low res) m/e 247 (M+H), 229, 215, 187, 175; Analysis calculated for C$_{15}$H$_{18}$O$_3$: C, 73.15; H, 7.37; found: C, 73.09; H, 6.74.

2-Propenyl-4-(2-propenyloxy)benzenepropanoic ester (271 mg, 1.1 mmol) is treated with 0.14 mL (1.38 mmol) of 10M sodium hydroxide solution according to the same procedure described for Example 2 to give 196 mg (86%) of 4-(2-propenyloxy)benzenepropanoic acid as a white powder. The product is utilized in the next reaction without further purification: m.p. 88°–89°; the $^1$H NMR (300 MHz, CDCl$_3$) is consistent with the desired product; IR (KBr) 3200, 1720, 1700, 1610 cm$^{-1}$; MS (CI low res) m/e 207 (M+H), 189, 175, 147; Analysis calculated for C$_{12}$H$_{14}$O$_3$: C, 69.89; H, 6.84; found: C, 69.87; H, 6.68.

4-(2-Propenyloxy)benzenepropanoic acid (120 mg, 0.58 mmol) is treated with ozone by the procedure described in Example 2 to give 100 mg (82%) of 4-(2-oxoethoxy) benzenepropanoic acid as a white powder: m.p. 95°–100°; the $^1$H NMR (300 MHz, CDCl$_3$) is consistent with the desired product; IR (KBr) 3400, 1740, 1720, 1610 cm$^{-1}$; MS (CI low res) m/e 207, 191, 179, 165, 149.

Example 2, Compound 6

3-(2-Oxoethoxy)benzoic acid

A mixture of 1.0 g (7.24 mmol) of 3-hydroxybenzoic acid, 3.0 g (25.3 mmol) of allyl bromide, and 5 g (36.2 mmol) of potassium carbonate in 4 mL of N,N-dimethylformamide is stirred at room temperature for 12 hours. The mixture is diluted with 20 mL of ether and washed five times with 20 mL of water. The organic layer is then washed successively with 20 mL of saturated sodium bicarbonate solution and 20 mL of saturated sodium chloride solution. The organic layer is separated and dried over magnesium sulfate. The mixture is filtered and the organic solution is concentrated in vacuo to give 1.4 g (88%) of 3-(2-propenyloxy)benzoic acid, 2-propenyl ester as a clear colorless oil. The product is utilized in the next reaction without further purification. The $^1$H NMR (300 MHz, CDCl$_3$) is consistent with the desired product; IR (KBr) 1720, 1650, 1600 cm$^{-1}$; MS (CI low res) m/e 219 (M+H), 203, 175, 161; Analysis calculated for C$_{13}$H$_{14}$O$_3$: C, 71.54; H, 6.47; found: C, 70.31; H, 5.97.

A solution of 917 mg (4.2 mmol) of 3-(2-propenyloxy) benzoic acid, 2-propenyl ester in 9 mL of methanol/water (3:2) at room temperature is treated with 0.53 mL (5.25 mmol) of 10M sodium hydroxide solution. The solution is allowed to stir for one hour then acidified with 5 mL of 10% sodium bisulfate solution and extracted with 25 mL of ethyl acetate. The organic layer is washed with saturated sodium chloride solution, dried over magnesium sulfate, and concentrated in vacuo to give 732 mg (97%) of 3-(2-propenyloxy)benzoic acid as a white powder. The product is utilized in the next reaction without further purification; m.p. 78°–79°; the $^1$H NMR (300 MHz, CDCl$_3$) is consistent with the desired product; IR (KBr) 3000, 1690, 1620, 1590 cm$^{-1}$; MS (CI low res) m/e 179 (M+H), 161, 135; Analysis calculated for C$_{10}$H$_{10}$O$_3$: C, 67.41; H, 5.66; found: C, 67.37; H, 5.59.

A solution of 300 mg (1.68 mmol) of 3-(2-propenyloxy) benzoic acid in 5 mL of methylene chloride is cooled to −78° C. Ozone is introduced by bubbling the gas into the solution through a glass tube until a blue color persists. The solution is then purged with a stream of argon and 1 mL of methyl sulfide is added. The solution is diluted with 20 mL of ether and washed with water. The organic layer is separated and allowed to stand over magnesium sulfate then concentrated in vacuo to give 283 mg (93%) of 3-(2-oxoethoxy)benzoic acid as a colorless oil. The product is utilized in the next reaction without further purification: m.p. 120°–130°; the $^1$H NMR (300 MHz, CDCl$_3$) is consistent with the desired product; IR (KBr) 3400, 3000, 1680, 1590 cm$^{-1}$; MS (CI low res) m/e 181 (M+H), 163, 139, 119.

Preparation 3, Compound 7

4-(4-Acetylphenoxy)butanoic acid

A solution of 0.90 g (6.61 mmol) of 4'-hydroxyacetophenone, and 1.93 g (9.92 mmol) of ethyl 4-bromobutyrate in 1.80 mL of N,N-dimethylformamide is stirred for 48 hours, under dry conditions with 2.74 g (19.8 mmol) of potassium carbonate and 0.110 g (0.66 mmol) of potassium iodide. The reaction mixture is then evaporated under vacuum, and the residue partitioned between ether and water. The organic phase is separated, washed thrice with water, dried with magnesium sulfate, filtered, and evaporated under vacuum to give a brown solid. This is recrystallized from a warm ether-hexane mixture. The beige crystals are air dried, leaving 0.84 g (51%) of 4-(4-acetylphenoxy)butanoic acid, ethyl ester: m.p. 59°–61° C.; IR (KBr) 1740, 1670 cm$^{-1}$; $^1$H-NMR (CDCl$_3$) is consistent with the desired product; MS (FAB) m/e 251.1285 Δ=−0.2 mmμ (M$^+$+H). Analysis calculated. for C$_{14}$H$_{18}$O$_4$: C, 67.18; H, 7.25; O, 25.57. Found: C, 67.16; H, 7.16; O, 25.68.

A sample of 0.25 g (1.00 mmol) of 4-(4-acetylphenoxy) butanoic acid, ethyl ester (example 1) is dissolved in 15 mL of methanol/water (3:2), with stirring. Then, 0.21 g (1.50 mmol) of potassium carbonate is added and the reaction is stirred for 18 hours under an argon atmosphere. Next, the reaction mixture is evaporated under vacuum and the residue dissolved in 20 mL of a 0.1N solution of sodium hydroxide. This basic solution is washed with ether, the aqueous phase acidified by addition of sodium bisulfate, and the resulting mixture extracted with ethyl acetate. This solution is then dried with magnesium sulfate, filtered and evaporated, leaving an off-white solid. This is crystallized from ethyl acetate with the addition of an equal volume of ether. This provides 0.18 g (80%) of 4-(4-acetylphenoxy)butanoic acid as light beige crystals: m.p. 148°–50° C.; IR (KBr) 1730, 1650 cm$^{-1}$; $^1$H-NMR (CDCl$_3$) is consistent with the desired product; MS (FAB) m/e 223.0974 Δ=−0.4 mmμ (M$^+$+H). Analysis calculated. for C$_{12}$H$_{14}$O$_4$: C, 64.85; H, 6.35; O, 28.80. Found: C, 64.61; H, 6.36; O, 29.03.

Preparation 4, Compound 8

4-(3-Formylphenoxy)butanoic acid

3-Hydroxybenzaldehyde (900 mg, 7.37 mmol) is treated with 2.16 g (11.05 mmol) of ethyl 4-bromobutyrate, 3.06 g (22.11 mmol) of potassium carbonate, and a catalytic amount (110 mg 0.74 mmol) of sodium iodide under the same conditions as in Preparation 3 to give a yellow oil. Purification by flash chromatography using hexane/ethyl acetate (10:1) gives 1.61 g of 4-(3-formylphenoxy)butanoic acid, ethyl ester as a light yellow oil. The $^1$H NMR (300 MHz, CDCl$_3$) is consistent with the desired product; IR (neat) 1730, 1700, 1600, 1580 cm$^{-1}$; MS (CI low res) m/e 237 (M+H), 191, 115.

A solution of 385 mg (1.63 mmol) of 4-(3-formylphenoxy)butanoic acid, ethyl ester and 850 mg (6.15 mmol) of potassium carbonate is stirred in 6 mL of methanol/water (3:2) at room temperature for 8 hours. The solution is then concentrated in vacuo. The residue is dissolved in 10 mL of 0.1N sodium hydroxide solution and washed with 20 mL of ether. The aqueous layer is separated and acidified with sodium bisulfate and extracted with ethyl acetate. The organic layer is washed with saturated sodium chloride solution, then dried over magnesium sulfate. The mixture is then filtered and concentrated in vacuo to give 315 mg of 4-(3-formylphenoxy)butanoic acid as a white solid. The product is utilized in the next reaction without further purification. m.p. 62°–63°; the $^1$H NMR (300 MHz, CDCl$_3$) is consistent with the desired product; IR (KBr) 3400, 3000, 1700, 1690, 1590 cm$^{-1}$; MS (CI low res) m/e 209 (M+H), 191, 123.

Preparation 5. Compound 9

4-(4-Formylphenoxy)butanoic acid

4-Hydroxybenzyl alcohol (1 g, 8.06 mmol) is treated with 1.73 g (8.86 mmol) of ethyl 4-bromobutyrate, 3.34 g (24.2 mmol) of potassium carbonate and a catalytic amount (120 mg 0.81 mmol) of sodium iodide under the same conditions as described in Preparation 3 to give 1.73 g of 4-[4-(hydroxymethyl)phenoxy]butanoic acid, ethyl ester as a light brown oil (90%). The product is utilized in the next reaction without further purification. The $^1$H NMR (300 MHz, CDCl$_3$) is consistent with the desired product; IR (neat) 3400, 1730, 1610, 1580, 1510 cm$^{-1}$; MS (CI) m/e 238, 221, 115.

A mixture of 230 mg (0.97 mmol) of 4-[4-(hydroxymethyl)phenoxy]butanoic acid, ethyl ester, 624.2 mg (2.9 mmol) of pyridinium chlorochromate, and a catalytic amount of 4 Å molecular sieve is stirred in 2 mL of methylene chloride at room temperature for 3 hours. The mixture is diluted with 20 mL of ether, filtered and concentrated in vacuo to give 175 mg (76%) of a light yellow oil. The oil (150 mg, 0.63 mmol) is dissolved in 2.3 mL of methanol/water (3:2) and treated with 307 mg (2.22 mmol) of potassium carbonate according to the procedure described for Example 4 to give 100 mg (75%) of 4-(4-formylphenoxy)butanoic acid as a white powder. The product is used without further purification. The $^1$H NMR (300 MHz, CDCl$_3$) is consistent with the desired product; IR (KBr) 3000, 1740, 1660 cm$^{-1}$; MS (CI (low res)) m/e 209 (M+H), 191, 123.

Preparation 6. Compound 10

4-(4-Acetyl-2-methylphenoxy)butanoic acid

Utilizing the procedure of Preparation 3, 2.00 g (13.32 mmol) of 4-hydroxy-3-methylacetophenone is alkylated with ethyl 4-bromobutyrate. This produces 3.45 g (98%) of 4-(4-acetyl-2-methylphenoxy)butanoic acid, ethyl ester as a golden oil, after drying at 75° C., under vacuum: IR (neat) 1740, 1675 cm$^{-1}$; $^1$H-NMR (CDCl$_3$) is consistent with the desired product; MS (FAB) m/e 265 (M$^+$+H). Analysis calculated. for C$_{15}$H$_{20}$O$_4$: C, 68.16; H, 7.63; O, 24.21. Found: C, 67.92; H, 7.44; O, 24.64.

Following the method of Preparation 3, 2.50 g (9.46 mmol) of 4-(4-acetyl-2-methylphenoxy)butanoic acid, ethyl ester is saponified to give the desired compound as a solid. It is recrystallized from ethyl acetate/ether leaving 1.32 g (59%) of 4-(4-acetyl-2-methylphenoxy)butanoic acid as white crystals: m.p. 114°–16° C.; IR (KBr) 1730, 1650 cm$^{-1}$; $^1$H-NMR (CDCl$_3$) is consistent with the desired product; MS (FAB) m/e 237 (M$^+$+H). Analysis calculated. for C$_{13}$H$_{16}$O$_4$: C, 66.08; H, 6.83; O, 27.09. Found: C, 65.88; H, 6.92; O, 27.20.

Preparation 7. Compound 11

4-(4-Formyl-2-methoxyphenoxy)butanoic acid

4-Hydroxy-3-methoxybenzyl alcohol (1 g, 6.49 mmol) is treated with 1.73 g (7.13 mmol) of ethyl 4-bromobutyrate, 2.69 g (19.46 mmol) of potassium carbonate and a catalytic amount (97.22 mg 0.65 mmol) of sodium iodide as described in Preparation 3 to give 821 mg of 4-[4-(hydroxymethyl)-2-methoxyphenoxy]butanoic acid, ethyl ester as a light brown oil (47%). The $^1$H NMR (300 MHz, CDCl$_3$) is consistent with the desired product; IR (neat) 3500, 1730, 1620, 1600 cm$^{-1}$; MS (CI (low res)) m/e 269 (M+H), 251, 223, 195.

4-[4-(Hydroxymethyl)-2-methoxyphenoxy]butanoic acid, ethyl ester (431 mg, 1.61 mmol) is treated with 1.0 g (4.8 mmol) of pyridinium chlorochromate by the procedure described in Example 5 to give 280 mg (65%) of 4-(4-formyl-2-methoxyphenoxy)butanoic, ethyl ester as a colorless oil. The $^1$H NMR (300 MHz, CDCl$_3$) is consistent with the desired product; IR (neat) 1730, 1690, 1600, 1580 cm$^{-1}$.

4-(4-Formyl-2-methoxyphenoxy)butanoic acid, ethyl ester (240 mg, 0.90 mmol) is dissolved in 3 mL of methanol/water (3:2) and treated with 435 mg (3.15 mmol) of potassium carbonate according to the procedure described for Example 4 to give 125 mg (58%) of 4-(4-formyl-2-methoxyphenoxy)butanoic acid as a white powder: m.p. 143°–148°; the $^1$H NMR (300 MHz, CDCl$_3$) is consistent with the desired product; IR (KBr) 3575, 3500, 1720, 1700, 1680, 1600, 1585 cm$^{-1}$; MS (CI (low res)) m/e 239 (M+H), 221, 207, 153.

Preparation 8. Compound 12

4-Formylbenzenepropanoic acid

A mixture of 253 mg (1.44 mmol) of 4-formylcinnamic acid and 32.61 mg of platinum oxide in 10 mL of methanol is stirred overnight at room temperature under an atmosphere of hydrogen supplied by a balloon. The mixture is filtered through celite and concentrated in vacuo. The residue is dissolved in 0.1N sodium hydroxide solution and washed with ether. The aqueous layer is then acidified and the product is extracted with ethyl acetate. The organic layer is washed with saturated sodium chloride solution and dried over magnesium sulfate. The solvent is removed in vacuo to afford an inseparable mixture of 4-formylphenylpropanoic acid and other reduction products. The mixture is utilized in the next reaction without characterization or further purification.

Preparation 9. Compound 13

4-(2,3-Dimethoxy-5-formylphenoxy)butanoic acid

Employing the method of Preparation 3, 3.30 g (18.41 mmol) of 3,4-dimethoxy-5-hydroxybenzaldehyde is alkylated with ethyl 4-bromobutyrate. 4-(2,3-Dimethoxy-5-formylphenoxy)butanoic acid, ethyl ester is obtained as a yellow-orange oil after drying under high vacuum at 60° C. (5.45 g, 100%): IR (neat) 1735, 1690 cm$^{-1}$; $^1$H-NMR (CDCl$_3$) is consistent with the desired product; MS (FAB) m/e 297 (M$^+$+H). Analysis calculated. for C$_{15}$H$_{20}$O$_6$: C, 60.80; H, 6.80; O, 32.40. Found: C, 60.51; H, 6.86; O, 32.63.

27

Following the procedure of Preparation 3, a sample of 4.70 g (15.86 mmol) of 4-(2,3-dimethoxy-5-formylphenoxy)butanoic acid, ethyl ester is saponified giving the desired compound as a cream colored solid. This is recrystallized from ethyl acetate/ether, leaving 3.65 g (86%) of 4-(2,3-dimethoxy-5-formylphenoxy)butanoic acid as off-white crystals: m.p. 90°–92° C.; IR (KBr) 1710, 1690 cm$^{-1}$; $^1$H-NMR (CDCl$_3$) is consistent with the desired product; MS (FAB) m/e 269 (M$^+$+H). Analysis calculated. for C$_{13}$H$_{16}$O$_6$: C, 58.20; H, 6.01; O, 35.79. Found: C, 58.10; H, 6.09; O, 35.81.

Preparation 10. Compound 14

4-(4-Acetyl-2,6-dimethoxyphenoxy)butanoic acid

Utilizing the procedure of Preparation 3, 2.61 g (13.32 mmol) of 4-acetyl-2,6-dimethoxyphenol is treated with ethyl 4-bromobutyrate. This gives the desired product after drying at −70° C., under high vacuum, as a brown oil. This is chromatographed on a column of silica gel, and eluted with a 1:1 mixture of ether/hexane leaving 0.40 g (10%) of 4-(4-acetyl-2,6-dimethoxyphenoxy)butanoic acid, ethyl ester as a colorless oil: IR (neat) 1735, 1675 cm$^{-1}$; $^1$H-NMR (CDCl$_3$) is consistent with the desired product; MS (FAB) m/e 311.1489 Δ=+0.6 mmµ (M$^+$+H). Analysis calculated. for C$_{16}$H$_{22}$O$_6$: C, 61.92; H, 7.14; O, 30.94. Found: C, 61.48; H, 7.04; O, 31.48.

Following the method of Preparation 3, 0.179 g (0.577 mmol) of 4-(4-acetyl-2,6-dimethoxyphenoxy)butanoic acid, ethyl ester is treated with potassium carbonate, producing an off-white solid. Recrystallization from ethyl acetate/hexane gives 4-(4-acetyl-2,6-dimethoxyphenoxy)butanoic acid as white crystals (0.14 g, 88%): m.p. 122°–24° C.; IR (KBr) 1735, 1660 cm$^{-1}$; $^1$H-NMR (CDCl$_3$) is consistent with the desired product; MS (FAB) m/e 283 (M$^+$+H). Analysis calculated. for C$_{14}$H$_{18}$O$_6$: C, 59.57; H, 6.43; O, 34.01. Found: C, 59.34; H, 6.40; O, 34.26.

Preparation 11. Compound 15

4-(4-Acetyl-2-methoxyphenoxy)butanoic acid

Employing the procedure of Preparation 3, 2.21 g (13.32 mmol) of 4-hydroxy-3-methoxyacetophenone is alkylated, producing a solid. This is recrystallized as in Preparation 3, leaving 3.23 g (86%) of 4-(4-acetyl-2-methoxyphenoxy) butanoic acid, ethyl ester as white crystals: m.p. 53°–55° C.; IR (KBr) 1745, 1675 cm$^{-1}$; $^1$H-NMR (CDCl$_3$) is consistent with the desired product; MS (FAB) m/e 281 (M$^+$+H). Analysis calculated. for C$_{15}$H$_{20}$O$_5$: C, 64.27; H, 7.19; O, 28.54. Found: C, 64.26; H, 7.05; O, 28.69.

Following the method of Preparation 3, 2.74 g (9.78 mmol) of 4-(4-acetyl-2-methoxyphenoxy)butanoic acid, ethyl ester is saponified. This produces 4-(4-acetyl-2-methoxyphenoxy)butanoic acid as off-white crystals after recrystallization from ethyl acetate (1.61 g, 87%): m.p. 161°–63° C.; IR (KBr) 1720, 1670 cm$^{-1}$; $^1$H-NMR (CDCl$_3$) is consistent with the desired product; MS (FAB) m/e 253 (M$^+$+H). Analysis calculated. for C$_{13}$H$_{16}$O$_5$: C, 61.90; H, 6.39; O, 31.71. Found: C, 61.75; H, 6.37; O, 31.88.

Preparation 12. Compound 16

4-|4-(3-oxobutyl)phenoxy|butanoic acid

4-Hydroxybenzylacetone (2 g, 12.18 mmol) is treated with 2.61 g (13.4 mmol) of ethyl 4-bromobutyrate, 5.05 g (36.5 mmol) of potassium carbonate and a catalytic amount

28

(182 mg 1.22 mmol) of sodium iodide in 2 mL N,N-dimethylformamide as described in Preparation 3 to give 2.73 g of 4-[4-(3-oxobutyl)phenoxy]butanoic, ethyl ester as a light brown oil (80%): m.p. 32°–34°; the $^1$H NMR (300 MHz, CDCl$_3$) is consistent with the desired product; IR (neat) 1730, 1720, 1610, 1580, 1510 cm$^{-1}$; MS (CI (low res)) m/e 279 (M+H), 233, 221; Analysis calculated for C$_{16}$H$_{22}$O$_4$: C, 69.04; H, 7.97; found: C, 68.33; H, 7.68.

4-|4-(3-Oxobutyl)phenoxy|butanoic acid, ethyl ester (716 mg, 2.57 mmol) is dissolved in 5 mL of methanol/water (3:2) and treated with 1.24 g (9.0 mmol) of potassium carbonate according to the procedure described for Example 4 to give 385 mg (60%) of 4-[4-(3-oxobutyl)phenoxy] butanoic acid as a white powder: m.p. 97°–99°; the $^1$H NMR (300 MHz, CDCl$_3$) is consistent with the desired product; IR (neat) 1730, 1700, 1620, 1520 cm$^{-1}$; Analysis calculated for C$_{14}$H$_{18}$O$_4$: C, 67.18; H, 7.25; found: C, 66.55; H, 7.09.

Example 13. Compound 17

4-(2-Acetyl-5-methoxyphenoxy)butanoic acid

Following the procedure of Preparation 3, 2.21 g (13.32 mmol) of 2-hydroxy-4-methoxyacetophenone is alkylated and worked up as before to leave 3.40 g (91%) of 4-(2-acetyl-5-methoxyphenoxy)butanoic acid, ethyl ester as a yellow oil: IR (neat) 1740, 1665 cm$^{-1}$; $^1$H-NMR (CDCl$_3$) is consistent with the desired product; MS (FAB) m/e 281 (M$^+$+H). Analysis calculated. for C$_{15}$H$_{20}$O$_5$: C, 64.27; H, 7.19; O, 28.54. Found: C, 64.06; H, 7.24; O, 28.70.

Utilizing the method of Preparation 3, 2.50 g (8.92 mmol) of 4-(2-acetyl-5-methoxyphenoxy)butanoic acid, ethyl ester is treated with potassium carbonate, producing a white solid. This is recrystallized from ethyl acetate/ether leaving 1.61 g (71%) of 4-(2-acetyl-5-methoxyphenoxy)butanoic acid as colorless crystals: m.p. 127°–29° C.; IR (KBr) 1720, 1655 cm$^{-1}$; $^1$H-NMR (CDCl$_3$) is consistent with the desired product; MS (FAB) m/e 253 (M$^+$+H). Analysis calculated. for C$_{13}$H$_{16}$O$_5$: C, 61.90; H, 6.39; O, 31.71. Found: C, 61.82; H, 6.37; O, 31.81.

Preparation 14. Compound 18

4-[4-(3-Oxopropyl)phenoxy]butanoic acid

Following the procedure of Preparation 3, 2.80 g (18.41 mmol) of 3-(4-hydroxyphenyl-1-propanol) is alkylated with ethyl 4-bromobutyrate. The product is dried at 70° C., under high vacuum, leaving 4.70 g (96%) of 4-[4-(3-hydroxypropyl)phenoxy]butanoic acid, ethyl ester as a colorless oil: IR (neat) 3400 (br.), 1735 cm$^{-1}$; $^1$H-NMR (CDCl$_3$) is consistent with the desired product; MS (CI) m/e 267 (M$^+$+H). Analysis calculated. for C$_{15}$H$_{22}$O$_4$: C, 67.65; H, 8.33; O, 24.03. Found: C, 67.40; H, 8.20; O, 24.38.

After the method of Preparation 3, 4.13 g (15.51 mmol) of 4-[4-(3-hydroxypropyl)phenoxy]butanoic acid, ethyl ester is saponified with potassium carbonate to produce a solid. This is recrystallized from an ethyl acetate-hexane mixture giving 2.45 (66%) of 4-[4-(3-hydroxypropyl) phenoxy]butanoic acid as white crystals: m.p. 92°–94° C.; IR (KBr) 3420 (br.), 1710 cm$^{-1}$; $^1$H-NMR (CDCl$_3$) is consistent with the desired product; MS (CI) m/e 239 (M$^+$+H). Analysis calculated. for C$_{13}$H$_{18}$O$_4$: C, 65.53; H, 7.61; O, 26.86. Found: C, 65.75; H, 7.87; O, 26.38.

A 1.19 g (5.00 mmol) sample of 4-[4-(3-hydroxypropyl) phenoxy]butanoic acid is dissolved with stirring in 250 mL of methylene dichloride. Next, 3.77 g (17.49 mmol) of pyridinium chlorochromate is added, the mixture is stirred for 4 hours, and then filtered through a celite pad. The reaction mixture is then diluted with an equal volume of ether, precipitating out salts. This mixture is then filtered through a silica gel pad, and the filtrate evaporated, giving a brown solid. The solid is recrystallized from an ether-hexane mixture producing 0.21 (18%) of 4-[4-(3-oxopropyl) phenoxy]butanoic acid as off-white crystals: m.p. 100°–03° C.; IR (KBr) 1715 cm$^{-1}$; $^1$H-NMR (CDCl$_3$) is consistent with the desired product; MS (CI) m/e 237 (M$^+$+H). Analysis calculated for C$_{13}$H$_{16}$O$_4$: C, 66.09; H, 6.83; O, 27.09. Found: C, 65.91; H, 6.72; O, 27.35.

Example 15. Compound 20

4-[(2-Acetyl-1-naphthalenyl)oxy]butanoic acid

A 3.42 g (18.37 mmol) sample of 1-hydroxy-2-acetonapthone is alkylated as in Preparation 3. The crude product is dried under high vacuum at 60° C. to give 5.21 g (94%) of 4-[(2-acetyl-1-naphthalenyl)oxy]butanoic acid, ethyl ester as a golden liquid: IR (neat) 1730, 1665 cm$^{-1}$; $^1$HNMR (CDCl$_3$) is consistent with the desired product; MS (FAB) m/e 301 (M$^+$+H). Analysis calculated for C$_{18}$H$_{20}$O$_4$: C, 71.98; H, 6.71; O, 21.31. Found: C, 72.11; H, 6.58; O, 21.31.

Utilizing the method of Preparation 3, 2.84 g (9.46 mmol) of 4-[(2-acetyl-1-naphthalenyl)oxy]butanoic acid, ethyl ester is saponified. The crude product is recrystallized from ethyl acetate/ether to give 1.15 g (45%) of 4-[(2-acetyl-1-naphthalenyl)oxy]butanoic acid as golden crystals: m.p. 104°–06° C.; IR (KBr) 1720, 1640 cm$^{-1}$; $^1$HNMR (CDCl$_3$) is consistent with the desired product; MS (FAB) m/e 273 (M$^+$+H). Analysis calculated for C$_{16}$H$_{16}$O$_4$: C, 70.58; H, 5.92; O, 23.50. Found: C, 70.40; H, 5.89; O, 23.71.

Preparation 16. Compound 21

4-[4-(4-Fluorobenzoyl)phenoxy]butanoic acid

Following the method of Preparation 3, 3.98 g (18.41 mmol) of 4-fluoro-4'-hydroxybenzophenone is alkylated with ethyl 4-bromobutyrate. The crude yellow solid product is recrystallized from ether providing 2.97 g (49%) of 4-[4-(4-fluorobenzoyl)phenoxy]butanoic acid, ethyl ester as white crystals: m.p. 57°–59° C.; IR (KBr) 1735, 1645 cm$^{-1}$; $^1$HNMR (CDCl$_3$) is consistent with the desired product; MS (FAB) m/e 311 (M$^+$+H). Analysis calculated for C$_{19}$H$_{19}$O$_4$F: C, 69.08; H, 5.80; F, 5.75; O, 19.37. Found: C, 69.09; H, 5.62; F, 5.95; O, 19.34.

Utilizing the procedure of Preparation 3, 0.48 g (1.45 mmol) of 4-[4-(4-fluorobenzoyl)phenoxy]butanoic acid, ethyl ester is saponified. The crude white solid product is recrystallized from an ether-hexane mixture leaving 0.16 g (36%) of 4-[4-(4-fluorobenzoyl)phenoxy]butanoic acid as white crystals: m.p. 109°–111° C.; IR (KBr) 1735, 1700 1640 cm$^{-1}$; $^1$HNMR (CDCl$_3$) is consistent with the desired product; MS (FAB) m/e 303 (M$^+$+H). Analysis calculated for C$_{17}$H$_{15}$O$_4$F: C, 67.54; H, 5.00; F, 6.28; O, 21.18. Found: C, 67.28; H, 4.89; F, 6.41; O, 21.42.

Example 17. Compound 22

4-(4-Acetylphenyl)-1-piperazinevaleric acid

4'-Piperazinoacetophenone (102 mg) is dissolved in 1 mL of N,N-dimethylformamide. After addition of methyl 5-bromovalerate (0.077 mL) and potassium carbonate (69 mg), the mixture is stirred at room temperature for 65 hours. TLC (10% MeOH/CH$_2$Cl$_2$) should show a single product spot without residual starting material. The reaction solution is evaporated under vacuum. The residue is taken up in methylene chloride, washed twice with water and dried over sodium sulfate. Evaporation of the solvent yields 137 mg of 4-(4-acetylphenyl)-1-piperazinevaleric acid, methyl ester as yellow crystals whose $^1$H-NMR (CDCl$_3$) spectrum is consistent with the assigned structure.

4-(4-Acetylphenyl)-1-piperazinevaleric acid, methyl ester (15.3 mg) is suspended in 0.1 mL of potassium hydroxide solution (33.2 mg/mL). After heating at 100° C. for 150 min, the starting material is completely dissolved and absent by TLC (10% MeOH/CH$_2$Cl$_2$). After acidifying the reaction solution to pH 4 by adding 0.2N HCl, the aqueous solution is extracted with methylene chloride. After evaporation of the organic layer to dryness, the residue is dissolved in methylene chloride and filtered. Evaporation of the organic layer gives 7 mg of 4-(4-acetylphenyl)-1-piperazinevaleric acid as a white solid. $^1$H-NMR (CDCl$_3$) spectrum is consistant with the assigned structure. MS (FAB) m/e 305 (M$^+$+H), 327 (M$^+$+Na), 348 (M$^+$+2Na—H).

Preparation 18. Compound 25

4-(2-Chloro-4-formylphenoxy)butanoic acid

Following the procedure of Preparation 3, 2.88 g (18.41 mmol) of 3-chloro-4-hydroxybenzaldehyde is alkylated as before. This produces 4.65 g (93%) of 4-(2-chloro-4-formylphenoxy)butanoic acid, ethyl ester as an orange oil: IR (neat) 1730, 1685 cm$^{-1}$; $^1$HNMR (CDCl$_3$) is consistent with the desired product; MS (CI) m/e 271 (M$^+$+H). Analysis calculated for C$_{13}$H$_{15}$O$_4$Cl: C, 57.68; H, 5.58; Cl, 13.10; O, 23.64. Found: C, 58.05; H, 5.37; Cl, 12.43; O, 24.15.

After the method of Preparation 3, 3.52 g (13.00 mmol) of 4(2-chloro-4-formylphenoxy)butanoic acid, ethyl ester is saponified to give a white solid. This is recrystallized from ethyl acetate resulting in 1.78 g (56%) of 4-(2-chloro-4-formylphenoxy)butanoic acid as white crystals: m.p. 128°–31° C.; IR (KBr) 1730, 1650 cm$^{-1}$; $^1$HNMR (CDCl$_3$) is consistent with the desired product; MS (CI) m/e 243 (M$^+$+H). Analysis calculated for C$_{11}$H$_{11}$O$_4$Cl: C, 54.45; H, 4.57; Cl, 14.61; O, 26.37. Found: C, 54.61; H, 4.70; Cl, 14.25; O, 26.42.

Example 19. Compound 26

5-Acetyl-2-(3-carboxypropoxy)benzoic acid, methyl ester

Under dry condition, 3.58 g (18.41 mmol) of 5-acetylsalicylic acid, methyl ester is dissolved in 25 mL of dry N,N-dimethylformamide. To this solution is added 3.07 g (20.58 mmol) of 5-bromo-1-pentene, 6.83 (20.58 mmol) of potassium carbonate, and 0.246 g (1.65 mmol) of potassium iodide, and the reaction mixture is stirred for 24 hours at ambient temperature. Another portion of 5-bromopentene is added to the reaction, followed by one-half portions of the other two reagents above, and stirring is continued for 72 hours. The mixture is then evaporated under high vacuum at 70° C. The residue is partitioned between ether/water and the organic phase is separated, dried with magnesium sulfate, filtered, and evaporated under vacuum to leave 4.60 g (95%) of 5-acetyl-2-(4-pentenyloxy)benzoic acid, methyl ester as a yellow liquid: IR (neat) 1735, 1710, 1680 cm$^{-1}$; $^1$HNMR (CDCl$_3$) is consistent with the desired product; MS (FAB) m/e 263 (M$^+$+H). Analysis calculated for C$_{15}$H$_{18}$O$_4$: C, 68.69; H, 6.92; O, 24.40. Found: C, 68.60; H, 6.92; O, 24.46.

A sample of 0.203 g (0.775 mmol) of 5-acetyl-2-(4-pentenyloxy)benzoic acid, methyl ester is dissolved in 5 mL of methylene dichloride, under an argon atmosphere, and cooled to −78° C. in a dry ice acetone bath, with stirring. Next, ozone gas is passed through this solution for 10 minutes, until it turns a light bluish color. Then 0.5 mL of dimethyl sulfide is added to quench the reaction and it is allowed to warm to room temperature for 2 hours. The mixture is then evaporated under high vacuum, leaving the crude aldehyde product as an oil which is used "as is" for the second step. It is dissolved in 5 mL of N,N-dimethylformamide, and 1.02 g (2.71 mmol) of pyridinium dichromate is added. This reaction mixture is sealed and allowed to stand for 20 hours. It is next poured into 50 mL of water, extracted with ether, and the organic phase is washed with water again, dried with magnesium sulfate, filtered, and evaporated, which gives oily crystals. These are recrystallized from a mixture of ethyl acetate and hexane, producing 0.109 g (50%) of 5-acetyl-2-(3-carboxypropoxy)benzoic acid, methyl ester as white crystals: m.p. 111°–113° C.; IR (KBr) 1725, 1645 cm$^{-1}$; $^1$HNMR (CDCl$_3$) is consistent with the desired product; MS (FAB) m/e 281 (M$^+$+H). Analysis calculated. for C$_{14}$H$_{16}$O$_6$: C, 60.00; H, 5.75; O, 34.25. Found: C, 59.96; H, 5.75; O, 34.27.

Preparation 20. Compound 27

4-(4-Formyl-2-nitrophenoxy)butanoic acid

4-Hydroxy-3-nitrobenzyl alcohol (1 g, 5.91 mmol) is treated with 1.44 g (7.39 mmol) of ethyl 4-bromobutyrate, 2.86 g (20.69 mmol) of potassium carbonate and a catalytic amount (88 mg 0.59 mmol) of sodium iodide as described in Preparation 3 to give 1.45 g of 4-[4-(hydroxymethyl)2-nitrophenoxy]butanoic acid, ethyl ester as a light yellow oil (86%). The $^1$H NMR (300 MHz, CDCl$_3$) is consistent with the desired product; IR (neat) 3400, 1730, 1710, 1630, 1580 cm$^{-1}$; MS (CI) m/e 284 (M+H), 238; Analysis calculated for C$_{13}$H$_{17}$O$_6$N: C, 55.12; H, 6.05; found: C, 55.36; H, 6.03.

4-[4-(Hydroxymethyl)2-nitrophenoxy]butanoic acid, ethyl ester (300 mg, 1.06 mmol) is treated with 799 mg (3.71 mmol) of pyridinium chlorochromate by the procedure described in Example 5 to give 188 mg (63%) of 4-(4-formyl-2-nitrophenoxy)butanoic acid, ethyl ester as a colorless oil. The $^1$H NMR (300 MHz, CDCl$_3$) is consistent with the desired product; IR (neat) 1730, 1700, 1610, 1570 cm$^{-1}$; MS (CI) m/e 282 (M+H).

4-(4-Formyl-2-nitrophenoxy)butanoic acid, ethyl ester (135 mg, 0.48 mmol) is dissolved in 3 mL of methanol/water (3:2) and treated with 232 mg (1.68 mmol) of potassium carbonate according to the procedure described for Example 4 to give 84 mg (69%) of 4-(4-formyl-2-nitrophenoxy)butanoic acid as a yellow powder: m.p. 136°–139°; the $^1$H NMR (300 MHz, CDCl$_3$) is consistent with the desired product; IR (KBr) 3400, 1730, 1700, 1650, 1600, 1570 cm$^{-1}$; MS (CI) m/e 254, 236, 224, 208, 196, 168.

Example 21. Compound 28

4-[2-[[(4-Acetylphenyl)amino]methyl]-6-methoxyphenoxy]butanoic acid 4-(2-Hydroxy-3-methoxybenzylamino)acetophenone (500 mg, 1.84 mmol) is treated with 629 mg (3.22 mmol) of ethyl 4-bromobutyrate, 764 mg (5.53 mmol) of potassium carbonate and a catalytic amount (182 mg, 1.22 mmol) of sodium iodide in 2 mL N,N-dimethylformamide as described in Preparation 3 to give 680 mg of 4-[2-[[(4-acetylphenyl)amino]methyl]-6-methoxyphenoxy]butanoic acid, ethyl ester as a light brown oil (95%). The $^1$H NMR (300 MHz, CDCl$_3$) is consistent with the desired product; IR (neat) 3400, 1730, 1660, 1600 cm$^{-1}$; MS (CI) m/e 386 (M+H), 115; Analysis calculated for C$_{22}$H$_{27}$O$_5$N: C, 68.55; H, 7.06; N, 3.63; found: C, 68.27; H, 6.81; N, 3.54.

4-[2-[[(4-Acetylphenyl)amino]methyl]-6-methoxyphenoxy]butanoic acid, ethyl ester (250 mg, 0.65 mmol) is dissolved in 5 mL of methanol/water (3:2) and treated with 313 mg (2.27 mmol) of potassium carbonate according to the procedure described for Example 4 to give 166 mg (71%) of 4-[2-[[(4-acetylphenyl)amino]methyl]-6-methoxyphenoxy]butanoic acid as a red colored solid: m.p. 85°–95° C.; The $^1$H NMR (300 MHz, CDCl$_3$) is consistent with the desired product; IR (KBr) 3400, 1720, 1630, 1580 cm$^{-1}$; MS (CI) m/e calculated for C$_{20}$H$_{23}$O$_5$NNa: 380.1473, found 380.1482; 358 (M+H), 233, 223, 221, 136.

Example 22. Compound 29

5-Acetyl-2-(3-carboxypropoxy)-benzoic acid, 1-(3-bromopropyl) ester

To a solution of 0.744 g (3.00 mmol) of 5-acetyl-2-(4-pentenyloxy)-benzoic acid (Example 19), under an argon atmosphere, with stirring, in 36 mL of methylene dichloride, is added 1.67 g (12.0 mmol) of 3-bromopropanol. This is followed by 0.912 g (9.0 mmol) of triethyl amine and by 1.66 g (3.75 mmol) of benzotriazol-1-yloxytris (dimethylamino) phosphonium hexafluorophosphate and the reaction is stirred for 20 hours. The mixture is then evaporated, under high vacuum at 65° C. The residue is partitioned between ether and water, the ether phase is washed twice more with water, dried with magnesium sulfate, filtered, and evaporated leaving a gum. This is chromatographed on a column of silica gel, and eluted with ethyl acetate/hexane (1:2) to give 0.80 g (72%) of 5-acetyl-2-(4-pentenyloxy)benzoic acid, 1-(3-bromopropyl) ester as a colorless oil: IR (neat) 1730, 1700, 1680 cm$^{-1}$; $^1$HNMR (CDCl$_3$) is consistent with the desired product; MS (FAB) m/e 369 (M$^+$+H). Analysis calculated for C$_{17}$H$_{21}$O$_4$Br: C, 55.30; H, 5.73; O, 17.33; Br 21.64. Found: C, 55.34; H, 5.44; O, 17.34; Br 21.88.

Following the procedure of Example 19, 0.377 g (1.02 mmol) of 5-acetyl-2-(4-pentenyloxy)-benzoic acid, 1-(3-bromopropyl) ester is ozonized, and then further oxidized with pyridinium dichromate producing a colorless gum which partially crystallizes. This is recrystallized from a mixture of equal parts of ethyl acetate and hexane leaving 0.277 g (70%) of 5-acetyl-2-(3-carboxypropoxy)-benzoic acid, 1-(3-bromopropyl) ester as white crystals: m.p. 103°–05° C.; IR (KBr) 1730, 1645 cm$^{-1}$; $^1$HNMR (CDCl$_3$) is consistent with the title product; MS (CI) m/e 389 (M$^+$+H). Analysis calculated for C$_{16}$H$_{19}$O$_6$Br: C, 49.63; H, 4.95; O, 24.79; Br, 20.63. Found: C, 49.90; H, 4.75; O, 24.94; Br, 20.39.

Preparation 23. Compound 30

4-(4-Acetyl-3-fluorophenoxy)butanoic acid

A solution of 2-fluoro-4-methoxyacetophenone in 5 mL of DMSO is stirred at 100° C. in the presence of 730 mg (15 mmol) of sodium cyanide to give a dark viscous sludge. The mixture is allowed to cool, then poured into 50 mL of ice water and acidified with 6N aqueous HCl. The acidic solution is extracted with ethyl acetate (50 mL×2) and the organic layers are combined and washed with water. The organic layer is then extracted twice with 1.0N aqueous sodium hydroxide solution. The basic layer is washed once with ether, then acidified with solid sodium bisulfate and extracted with ethyl acetate twice. The ethyl acetate layers are combined, then washed with 10% sodium bisulfate solution and saturated sodium chloride solution. The organic phase is dried over magnesium sulfate and concentrated in vacuo at ambient temperature to give 143 mg (31%) of an oil.

The oil isolated above is dissolved in 1 mL of N,N-dimethylformamide and treated with 205 mg (1.05 mmol) of ethyl 4-bromobutyrate, 4.07 g (2.95 mmol) of potassium carbonate and a catalytic amount (1.26 mg, 0.008 mmol) of sodium iodide according to the procedure described in Preparation 3 to give 39 g of 4-(4-acetyl-3-fluorophenoxy) butanoic acid, ethyl ester as a light brown oil (17%). The $^1$H NMR (300 MHz, CDCl$_3$) is consistent with the desired product; MS (CI (low res)) m/e calculated for $C_{14}H_{18}O_4F$: 269.1189, found 269.1191.

4-(4-Acetyl-3-fluorophenoxy)butanoic acid, ethyl ester (20 mg, 0.0745 mmol) is dissolved in 1 mL of methanol/water (3:2) and treated with 30.91 mg (0.22 mmol) of potassium carbonate according to the procedure described for Example 4 to give 14 mg (82%) of 4-(4-acetyl-3-fluorophenoxy)butanoic acid as a white powder: m.p. 110°–111° C.; The $^1$H NMR (300 MHz, CDCl$_3$) is consistent with the desired product; IR (KBr) 1710, 1670, 1610 cm$^{-1}$; MS m/e calculated for $C_{12}H_{13}O_4FNa$: 263.0695, found 263.0699.

Example 24. Compound 31

(2-Acetylphenoxy)butanoic acid

2-Acetylphenol (1 g, 7.34 mmol) is treated with 1.79 g (9.18 mmol) of ethyl 4-bromobutyrate, 3.55 g (25.71 mmol) of potassium carbonate and a catalytic amount (11 mg, 0.07 mmol) of sodium iodide as described in Preparation 3 to give 1.84 g of (2-acetylphenoxy)butyric acid, ethyl ester as a light yellow oil which solidified upon standing: m.p. 43°–45° C.; The $^1$H NMR (300 MHz, CDCl$_3$) is consistent with the desired product; IR (neat) 1730, 1660, 1600 cm$^{-1}$; MS (CI) m/e 251 (M+H), 232, 205.

(2-Acetylphenoxy)butanoic acid, ethyl ester (500 mg, 2.00 mmol) is dissolved in 3 mL of methanol/water (3:2) and treated with 828 mg (5.99 mmol) of potassium carbonate according to the procedure described for Example 4 to give 412 mg (93%) of (2-acetylphenoxy)butanoic acid as a white powder. The $^1$H NMR (300 MHz, CDCl$_3$) is consistent with the desired product; IR (KBr) 1710, 1670, 1590 cm$^{-1}$; MS m/e calculated for $C_{12}H_{15}O_4$: 223.0970, found 223.0971.

Example 25. Compound 32

2-Acetyl-10H-phenothiazine-10-hexanoic acid

A solution of 500 mg (2.07 mmol) of 2-acetylphenothiazine in 8 mL of tetrahydrofuran is cooled to −78° C. and 4.14 mL (2.07 mmol) of a 0.5M solution of potassium bis(trimethylsilyl)amide in toluene is added. After five minutes, a solution of [(6-bromohexyl)oxy]-(1,1-dimethylethyl)dimethyl silane in 2 mL of tetrahydrofuran is added and the reaction is allowed to warm to room temperature. The mixture is diluted with 25 mL of ethyl acetate and washed with 10% sodium bisulfate solution and saturated sodium chloride solution, then dried over magnesium sulfate and concentrated in vacuo to give a dark colored residue. Flash chromatography (3:1 hexane/ethyl acetate) provides 318 mg (33%) of 1-[10-[6-[[(1,1-dimethylethyl) dimethylsilyl]oxy]hexyl]-10H-phenothiazin-2-yl]ethanone as a dark colored oil. The $^1$H NMR (300 MHz, CDCl$_3$) is consistent with the desired product; IR (neat) 1680, 1600, 1560 cm$^{-1}$; MS m/e calculated for $C_{26}H_{37}NO_2SSi$: 455.2314, found 455.2312.

A solution of 150 mg (0.33 mmol) of 1-[10-[6-[[(1,1-dimethylethyl)dimethylsilyl]oxy]hexyl]-10H-phenothiazin-2-yl]ethanone in 0.6 mL of tetrahydrofuran is treated with 0.41 mL (0.41 mmol) of 1M tetrabutylammonium fluoride in tetrahydrofuran. The reaction is stirred for 3 hours at room temperature, then diluted with 20 mL of ethyl acetate. The organic layer is washed successively with 10% sodium bisulfate solution and saturated sodium chloride solution, then dried over magnesium sulfate and concentrated in vacuo to give 114 mg of 1-[10-(6-hydroxyhexyl)-10H-phenothiazin-2-yl]ethanone as a dark oil. The $^1$H NMR (300 MHz, CDCl$_3$) is consistent with the desired product; IR (neat) 3400, 1680, 1590, 1560 cm$^{-1}$; MS m/e calculated for $C_{20}H_{23}NO_2S$: 341.1449, found 341.1456.

A solution of 41 mg (0.12 mmol) of 1-[10-(6-hydroxyhexyl)-10H-phenothiazin-2-yl]ethanone in 0.16 mL of N,N-dimethylformamide is treated with 158 mg (0.42 mmol) of pyridinium dichromate and stirred at room temperature for 12 hours. The mixture is diluted with ether and filtered through a pad of celite with the aid of 100 mL of ether. The filtrate is washed successively with 10% sodium bisulfate solution and saturated sodium chloride solution, then dried over magnesium sulfate and concentrated in vacuo to give 10 mg (23%) of 2-acetyl-10H-phenothiazine-10-hexanoic acid as a dark residue. The $^1$H NMR (300 MHz, CDCl$_3$) is consistent with the desired product. MS (CI) m/e 323 (M$^+$+H).

Example 26. Compound 34

5-Acetyl-2-(3-carboxypropoxy)-N-(2-dimethylaminoethyl)benzamide

A sample of 0.140 g (0.50 mmol) of 5-acetyl-2-(3-carboxypropoxy)-benzoic acid, methyl ester (Example 19) is heated on a steam bath, under dry conditions with 5.49 mL (50.0 mmol) of N,N-dimethylethylenediamine for 5 hours. The mixture is allowed to cool for 20 hours to ambient temperature and evaporated under vacuum at 55° C. The brown gum produced is triturated with ether, and the remaining residue taken up in water and acidified with hydrochloric acid. This is then extracted with ethyl acetate, and the aqueous solution is evaporated under vacuum, leaving a gum. It is next triturated with hot chloroform and this solution is evaporated to give a brown glass. This is chromatographed on a preparatory silica gel plate which is eluted with a 9/1 mixture of chloroform to methanol. The product band is cut from the plate, triturated with the above solvent mixture, filtered, and evaporated leaving 0.025 g (15%) of 5-acetyl-2-(3-carboxypropoxy)-N-(2-dimethylaminoethyl) benzamide as a light brown gum: MS (FAB) m/e 337.1753 Δ=+0.9 mmμ (M$^+$+H), 359 (M$^+$+Na). $^1$HNMR (CDCl$_3$) is consistent with the desired product.

Example 27. Compound 35

5-Acetyl-2-(3-carboxypropoxy)-N-(2-trimethylaminoethyl)-benzamide, internal salt To 100 mg of 5-acetyl-2-(3-carboxypropoxy)-N-(2-dimethylaminoethyl)-benzamide in 2 mL of methanol and 8 mL of pH 8.6 phosphate buffer is added 0.5 mL of dimethyl sulfate. The reaction pH is monitored about every 30 minutes and 0.1N sodium hydroxide is added as needed to return the pH to ~8.5. After 4 hours the solvents are removed under vacuum and the product is purified on BioSil A with a methanol-in-chloroform gradient to give 5-acetyl-2-(3-carbomethoxypropoxy)-N-(2-trimethylaminoethyl)-benzamide, chloride which is taken on to the next step. $^1$H-NMR (CDCl$_3$): 8.6 ppm (1H, d), 8.1 ppm (1H, dd), 7.1 ppm (1H, d), 4.3 ppm (2H, t), 4.0 ppm (2H, br t), 3.9 ppm (2H, br s), 3.7 ppm (3H, s), 3.7 ppm (1H, t), 3.3 ppm (9H, s), 2.1 ppm (3H, s), 2.1 ppm (2H, t), 2.3 ppm (2H, m).

The above product is dissolved in 2 mL of tetrahydrofuran and treated with an excess of 1N sodium hydroxide for 16 hours at ambient temperature. The organic cosolvent is removed under vacuum and the aqueous solution which remains is acidified with 1N HCl to a pH of about 5. The solution is then evaporated under vacuum to give a glass which crystallizes on standing. The resultant 5-acetyl-2-(3-carboxypropoxy)-N-(2-trimethylaminoethyl)benzamide, internal salt can be used without further purification. MS (FAB) m/e 351 (M$^+$+H).

Example 28, Compound 36

5-Acetyl-2-|N-(2-dimethylaminoethyl)-3-carboxamidopropoxy|benzoic acid, internal salt To 1.16 g of 5-acetylsalicylic acid, methyl ester in 10 mL of N,N-dimethylformamide is added 1 g of chloroacetic acid, methyl ester and 1.2 g of potassium carbonate. After stirring this mixture at ambient temperature for 16 hours the reaction is filtered, diluted with ethyl acetate, and washed once with water and twice with brine. The ethyl acetate is dried with magnesium sulfate, filtered, and evaporated to give 5-acetyl-2-(carboxymethoxy)benzoic acid as a crude product. Crystallization from methanol at −15° C. gives 0.6 g of white crystals. $^1$H-NMR (CDCl$_3$): 8.5 ppm (1H, d), 8.1 ppm (1H, dd), 6.9 ppm (1H, d), 4.8 ppm (2H, s), 4.0 ppm (3H, s), 3.8 ppm (3H, s), 2.6 ppm (3H, s).

450 mg of the above product is stirred in 1 mL of N,N-dimethylethylenediamine at ambient temperature for 16 hours. The reaction is then diluted with ethyl acetate and water. The water layer is extracted five times with ethyl acetate and the ethyl acetate from the various extractions is pooled, dried with magnesium sulfate, filtered, and evaporated to give 380 mg of 5-acetyl-2-[N-(2-dimethylaminoethyl)-3-carboxamidopropoxy]benzoic acid, methyl ester as a yellowish oil which is pure enough for further use. $^1$H-NMR (CDCl$_3$): 8.6 ppm (1H, d), 8.2 ppm (1H, dd), 8.1 ppm (1H, br t), 7.0 ppm (1H, d), 4.7 ppm (2H, s), 4.0 ppm (3H, s), 3.5 ppm (2H, q), 2.7 ppm (3H, s), 2.6 ppm (2H, t), 2.3 ppm (6H, s).

To 280 mg of the above compound in 15 mL of methanol and 5 mL of chloroform is added 1 mL of methyl iodide. After 3 hr at ambient temperature the volatile components are removed. 1H-NMR indicates the presence of the desired 5-acetyl-2-[N-(2-trimethylaminoethyl)-3-carboxamidopropoxy]benzoic acid, methyl ester, iodide. $^1$H-NMR (CDCl$_3$+CD$_3$OD): 8.8 ppm (1H, br t), 8.6 ppm (1H, d), 8.2 ppm (1H, dd), 7.1 ppm (1H, d), 4.7 ppm (2H, s), 4.0 ppm (3H, s), 3.9 ppm (2H, q), 3.8 ppm (2H, t), 3.4 (9H, s), 2.6 ppm (3H, s).

The above compound is dissolved in ~5 mL of methanol. Five equivalents of sodium hydroxide is added as a 5N solution in water. After 5 hours at ambient temperature the pH is adjusted to ~7.5 with dilute HCl and the volatile components are removed under vacuum to give a crude product containing 5-acetyl-2-[N-(2-trimethylaminoethyl)-3-carboxamidopropoxy]benzoic acid, internal salt. MS (CI) m/e 323 (M$^+$+H).

SYNTHESIS OF STRUCTURES B (SCHEME 1)
General Procedure

The drug-hydrazide derivative (Q-Sp-S-S-W wherein Q=H$_2$NHN—) is dissolved in alcohol or other compatible organic solvent containing ~3 to 10 equivalents of the carbonyl linker and ~1–10% acetic acid or other appropriate acid catalyst. A minimal amount of solvent gives a faster reaction. Anhydrous conditions give the best results as the condensation is an equilibrium reaction. The reaction is allowed to proceed at a temperature of ~20°–60° C. until complete by HPLC or alternately by TLC. This requires from a few hours to a day or more depending on the linker and the specific reaction conditions. The solvents are removed in vacuo and the crude product is purified on an appropriate silica gel, such as BIOSIL A™, using an appropriate solvent system, such as a gradient of 0 to 20% methanol in either chloroform or ethyl acetate. The products are sufficiently pure for subsequent steps.

Example 29

4-Formylphenoxyacetic acid (1) condensed with Calicheamicin N-acetyl gamma dimethyl hydrazide HPLC retention time: 4.4 min.
FAB MS: 1641 (M+H).
UV max at 291 and 305 nm (acetate).
$^1$H-NMR: See FIG. 6.

Preparation 30

Figure 7:
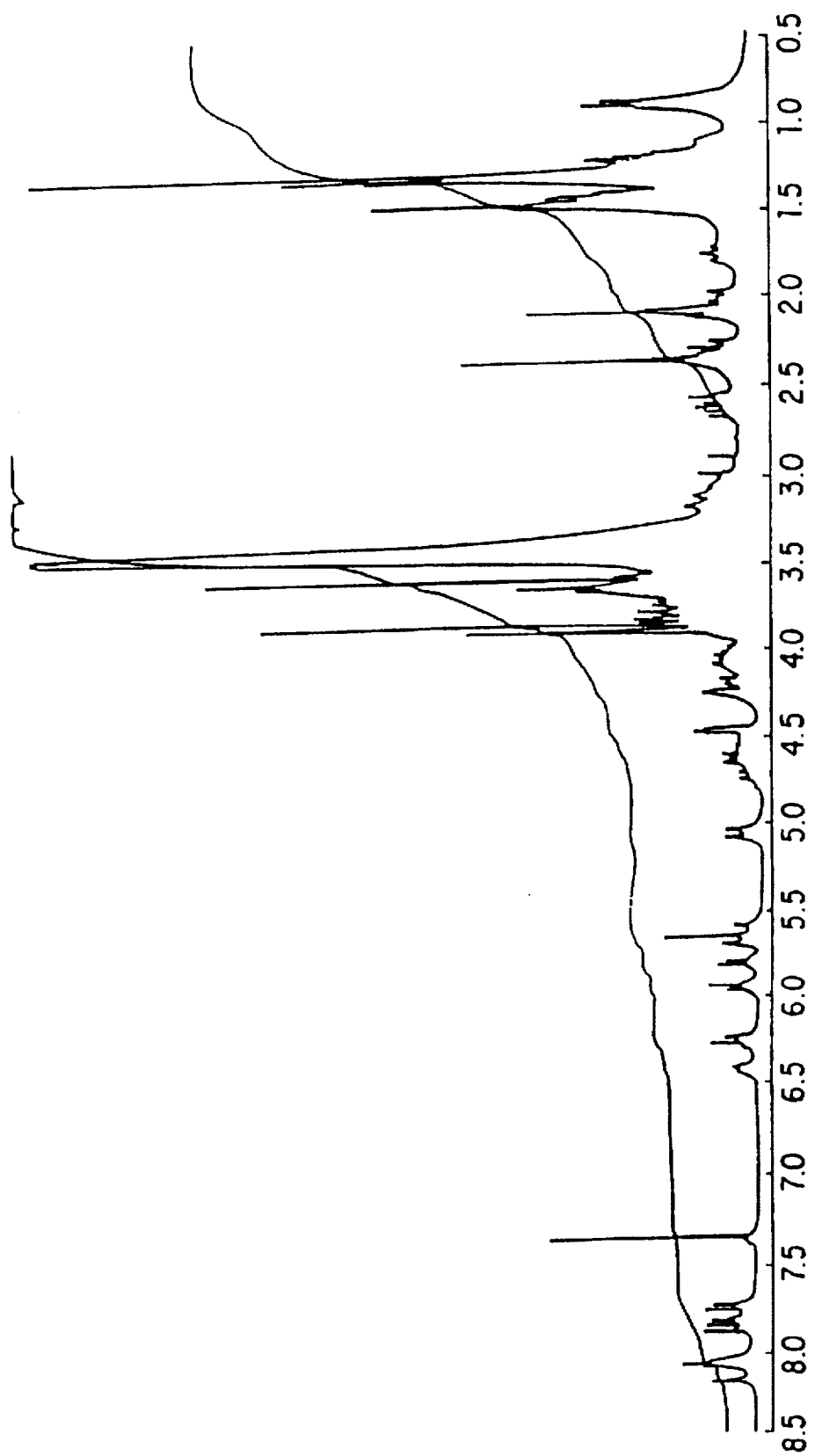
FIG. 7: The proton magnetic resonance spectrum of 4-formylbenzoic acid condensed with Calicheamicin N-acetyl gamma dimethyl hydrazide.

4-Formylbenzoic acid (2) condensed with Calicheamicin N-acetyl gamma dimethyl hydrazide HPLC retention time: 5.2 min.
FAB MS: 1611 (M+H).
UV max at 292 and 302 nm (ethanol).
$^1$H-NMR: See FIG. 7.

Preparation 31

Figure 8:
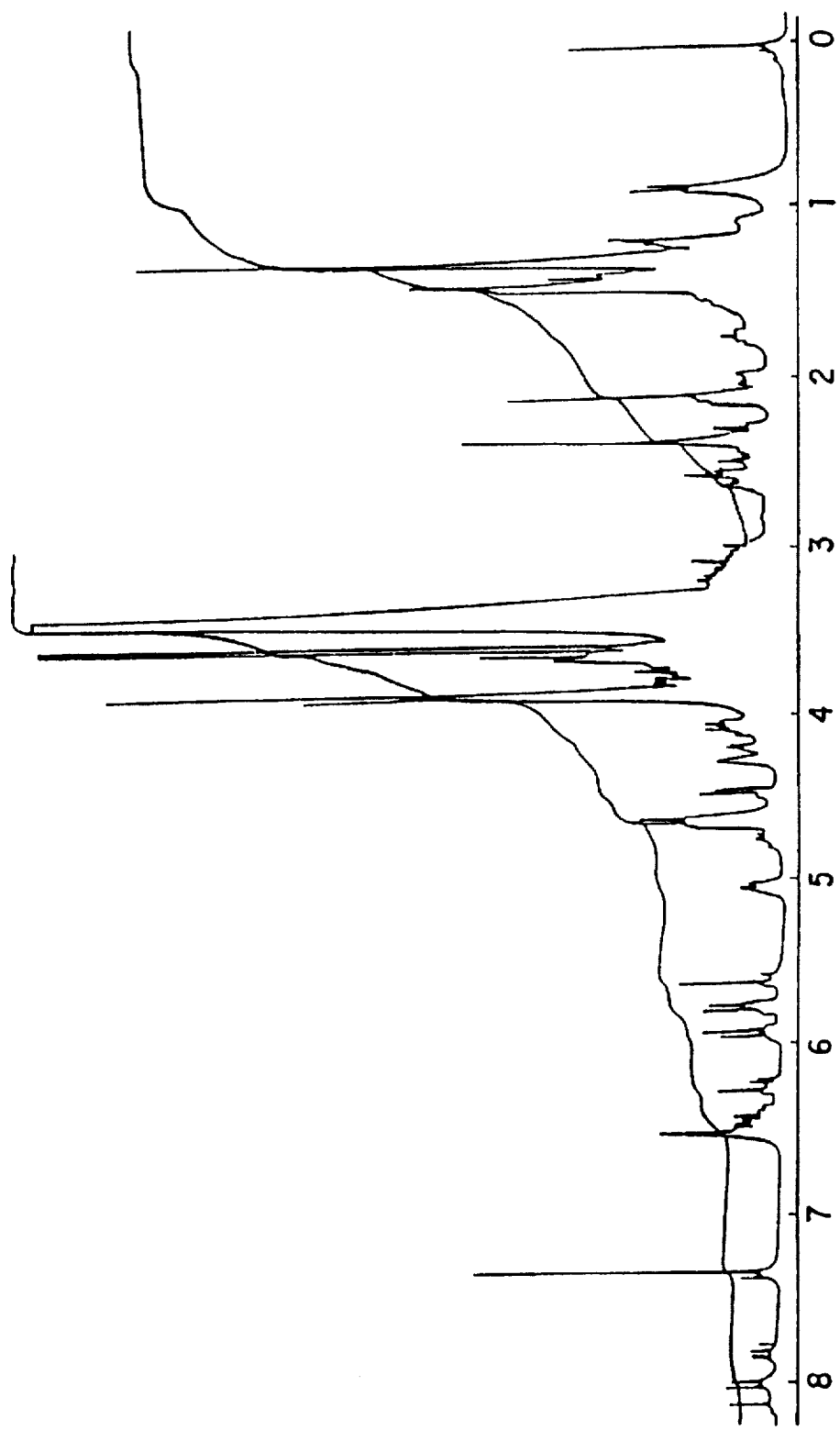
FIG. 8: The proton magnetic resonance spectrum of 4-formyl-3-methoxyphenoxyacetic acid condensed with Calicheamicin N-acetyl gamma dimethyl hydrazide.

4-Formyl-3-methoxyphenoxyacetic acid (3) condensed with Calicheamicin N-acetyl gamma dimethyl hydrazide HPLC retention time: 4.7 min.
FAB MS: 1671 (M+H).
UV max at 282, 291, and 325 nm (ethanol).
$^1$H-NMR: See FIG. 8.

Preparation 32

Figure 9:
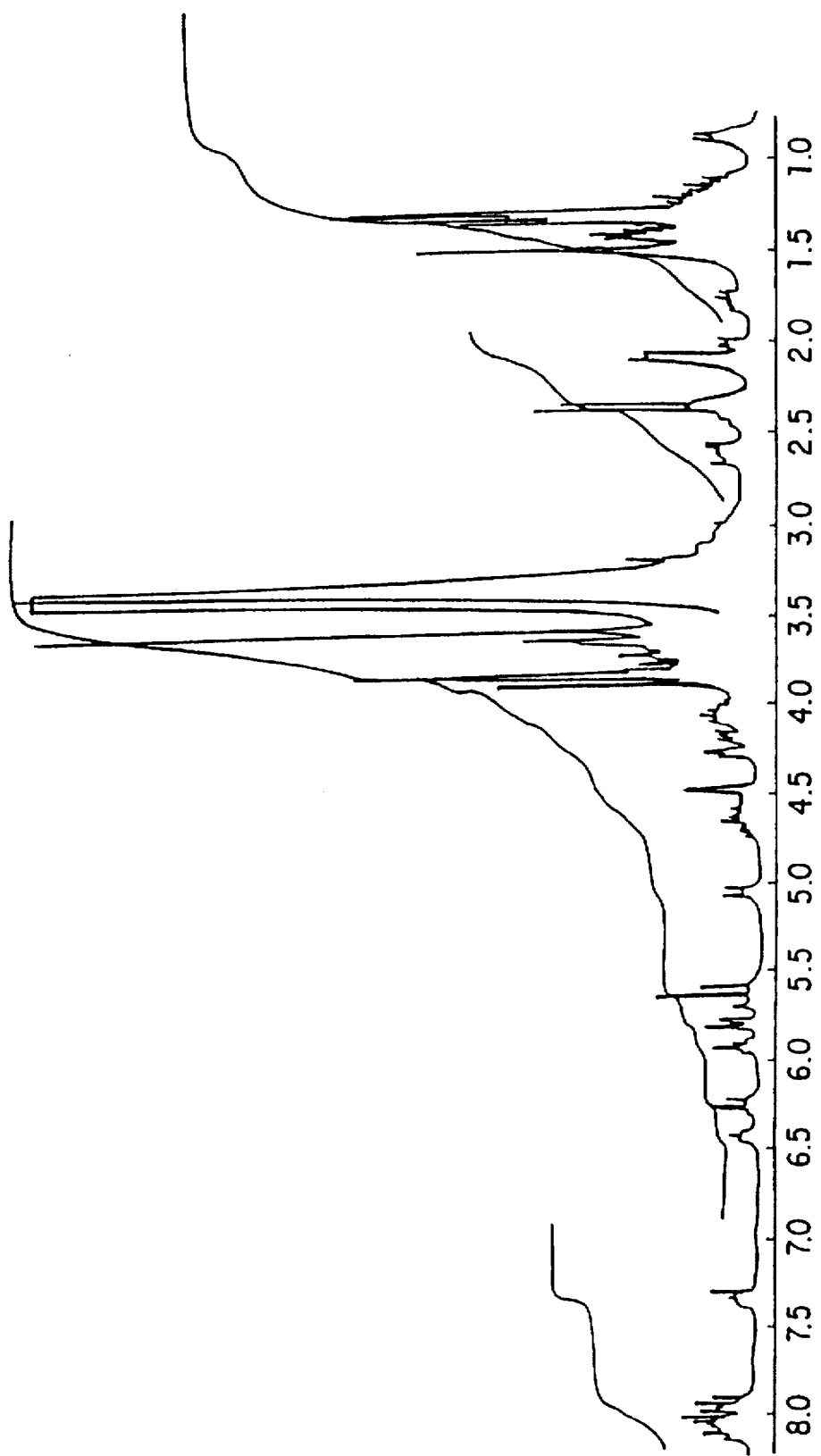
FIG. 9: The proton magnetic resonance spectrum of 6-formyl-2-naphthoic acid condensed with Calicheamicin N-acetyl gamma dimethyl hydrazide.

6-Formyl-2-naphthoic acid (4) condensed with Calicheamicin N-acetyl gamma dimethyl hydrazide HPLC retention time: 6.1 min.
FAB MS: 1661 (M+H).
UV max at 257, 267, 277, 313, and 321 nm (ethanol).
$^1$H-NMR: See FIG. 9.

Preparation 33

4-(2-Oxoethoxy)benzenepropanoic acid (5) condensed with Calicheamicin N-acetyl gamma dimethyl hydrazide HPLC retention time: 6.0 min.
FAB MS: 1669 (M+H).

UV—no maxima.

Preparation 34

3-(2-Oxoethoxy)benzoic acid (6) condensed with Calicheamicin N-acetyl gamma dimethyl hydrazide HPLC retention time: 5.5 min.
FAB MS: 1641 (M+H).
UV—no maxima.

Preparation 35

Figure 10:
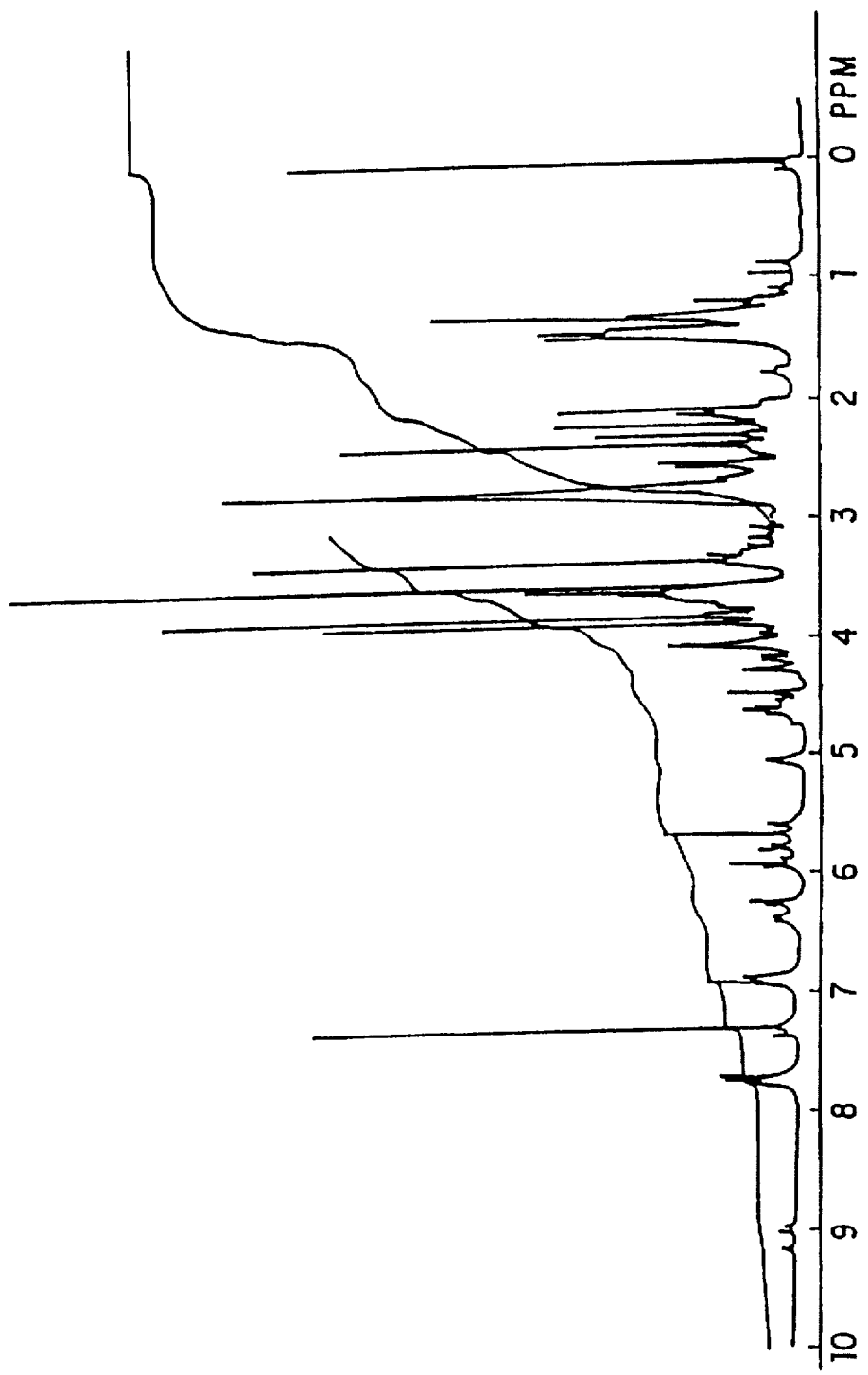
FIG. 10: The proton magnetic resonance spectrum of 4-(4-acetylphenoxy)butanoic acid condensed with Calicheamicin N-acetyl gamma dimethyl hydrazide.

4-(4-Acetylphenoxy)butanoic acid (7) condensed with Calicheamicin N-acetyl gamma dimethyl hydrazide HPLC retention time: 6.4 min.
FAB MS: 1683 (M+H).
UV max at 285 nm (ethanol).
$^1$H-NMR: See FIG. 10.

Preparation 36

4-(4-Acetylphenoxy)butanoic acid (7) condensed with calicheamicin gamma dimethyl hydrazide HPLC retention time: 6.2 min.
UV max at 285 nm (ethanol).

Preparation 37

4-(3-Formylphenoxy)butanoic acid (8) condensed with Calicheamicin N-acetyl gamma dimethyl hydrazide HPLC retention time: 6.3 min.
FAB MS: 1669 (M+H).

Preparation 38

Figure 12:
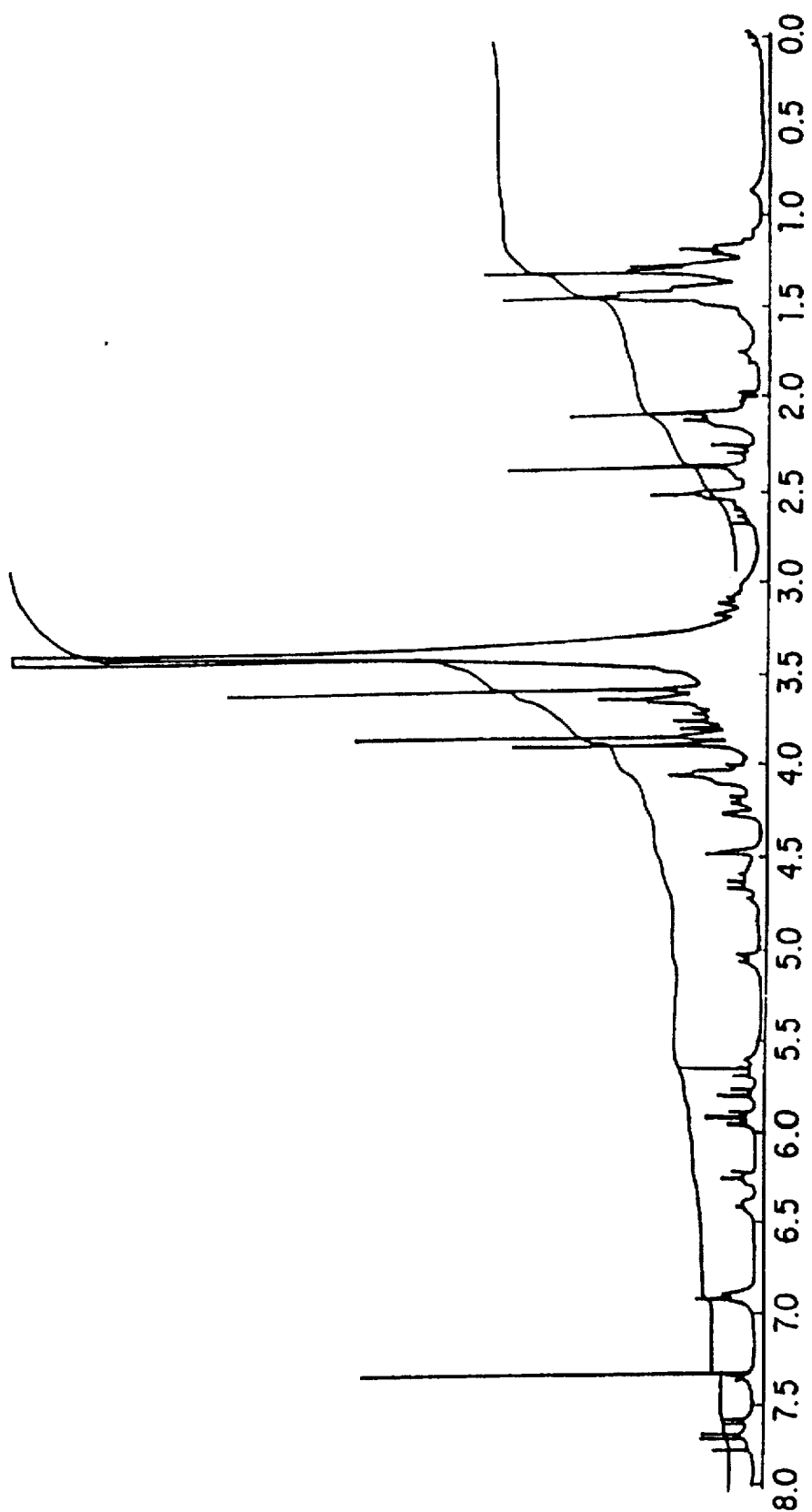
FIG. 12: The proton magnetic resonance spectrum of 4-(4-formylphenoxy)butanoic acid condensed with Calicheamicin N-acetyl gamma dimethyl hydrazide.

4-(4-Formylphenoxy)butanoic acid (9) condensed with Calicheamicin N-acetyl gamma dimethyl hydrazide HPLC retention time: 6.1 min.
FAB MS: 1669 (M+H).
UV max at 291 nm (ethanol).
$^1$H-NMR: See FIG. 12.

Preparation 39

4-(4-Acetyl-2-methylphenoxy)butanoic acid (10) condensed with Calicheamicin N-acetyl gamma dimethyl hydrazide HPLC retention time: 6.8 min.
FAB MS: 1697 (M+H).

Example 40

4-(4-Formyl-2-methoxyphenoxy)butanoic acid (11) condensed with Calicheamicin N-acetyl gamma dimethyl hydrazide HPLC retention time: 5.5 min.
FAB MS: 1699 (M+H).

UV max at 284, 300, and 316 nm (acetonitrile).

Example 41

4-Formylbenzenepropanoic acid (12) condensed with Calicheamicin N-acetyl gamma dimethyl hydrazide HPLC retention time: 5.6 min.
FAB MS: 1639 (M+H).

Example 42

4-(2,3-Dimethoxy-5-formylphenoxy)butanoic acid (13) condensed with Calicheamicin N-acetyl gamma dimethyl hydrazide HPLC retention time: 5.8 min.
FAB MS: 1729 (M+H).
UV max at 302 nm (ethanol).

Example 43

4-(4-Acetyl-2,6-dimethoxyphenoxy)butanoic acid (14) condensed with Calicheamicin N-acetyl gamma dimethyl hydrazide HPLC retention time: 6.0 min.
FAB MS: 1743 (M+H).
UV max at 287 nm (ethanol).

Example 44

4-(4-Acetyl-2-methoxyphenoxy)butanoic acid (15) condensed with Calicheamicin N-acetyl gamma dimethyl hydrazide HPLC retention time: 6.1 min.
FAB MS: 1713 (M+H).
UV max at 284 nm (ethanol).

Example 45

4-[4-(3-Oxobutyl)phenoxy]butanoic acetic acid (16) condensed with Calicheamicin N-acetyl gamma dimethyl hydrazide HPLC retention time: 6.6 min.
FAB MS: 1611 (M+H).
UV—no maxima.

Example 46

4-(2-Acetyl-5-methoxyphenoxy]butanoic acid (17) condensed with Calicheamicin N-acetyl gamma dimethyl hydrazide HPLC retention time: 6.5 min.
FAB MS: 1713 (M+H).
UV—no maxima.

Example 47

4-[4-(3-Oxopropyl)phenoxy]butanoic acid (18) condensed with Calicheamicin N-acetyl gamma dimethyl hydrazide HPLC retention time: 9.8 min.
FAB MS: 1697 (M+H).

UV—no maxima.

Example 48

4-Acetylbenzenebutanoic acid (19) condensed with Calicheamicin N-acetyl gamma dimethyl hydrazide HPLC retention time: 6.4 min.
FAB MS: 1667 (M+H).
UV max at 281 nm (ethanol).

Example 49

4-[(2-Acetyl-1-naphthalenyl)oxy] butanoic acid (20) condensed with Calicheamicin N-acetyl gamma dimethyl hydrazide HPLC retention time: 7.8 min.
FAB MS: 1733 (M+H).
UV—no maxima.

Example 50

4-[4-(4-Fluorobenzoyl)phenoxy]butanoic acid (21) condensed with Calicheamicin N-acetyl gamma dimethyl hydrazide HPLC retention time: 8.4 min.
FAB MS: 1763 (M+H).
UV max at 284 nm (ethanol).

Example 51

4-(4-Acetylphenyl)-1-piperazinepentanoic acid (22) condensed with Calicheamicin N-acetyl gamma dimethyl hydrazide HPLC retention time: 5.0 min.
FAB MS: 1641 (M+H).
UV max at 322 nm (ethanol).

Example 52

11-(4-Acetylphenoxy)undecanoic acid (23) condensed with Calicheamicin N-acetyl gamma dimethyl hydrazide HPLC retention time: 4.8 min (65% acetonitrile-isocratic).
FAB MS: 1781 (M+H).
UV max at 286 nm (ethanol).

Example 53

5-[(4-Acetylphenyl)amino]-5-oxopentanoic acid (24) condensed with Calicheamicin N-acetyl gamma dimethyl hydrazide HPLC retention time: 5.2 min.
FAB MS: 1710 (M+H).
UV max at 295 nm (ethanol).

Example 54

4-(2-Chloro-4-formylphenoxy)butanoic acid (25) condensed with Calicheamicin N-acetyl gamma dimethyl hydrazide HPLC retention time: 6.5 min.
FAB MS: 1704 (M+H).
UV max at 292 nm (ethanol).

Example 55

5-Acetyl-2-(3-carboxypropoxy)benzoic acid (26), methyl ester condensed with Calicheamicin N-acetyl gamma dimethyl hydrazide HPLC retention time: 6.1 min.
FAB MS: 1741 (M+H).
UV max at 285 nm (ethanol).

Example 56

4-(4-Formyl-2-nitrophenoxy)butanoic acid (27) condensed with Calicheamicin N-acetyl gamma dimethyl hydrazide HPLC retention time: 6.2 min.
FAB MS: 1741 (M+H).
UV max at 294 nm (ethanol).

Example 57

4-[2-[[(4-Acetylphenyl)amino]methyl]-6-methoxyphenoxy]butanoic acid (28) condensed with Calicheamicin N-acetyl gamma dimethyl hydrazide HPLC retention time: 7.7 min.
FAB MS: 1818 (M+H).
UV max at 323 nm (ethanol).

Example 58

4-(4-Acetyl-3-fluorophenoxy)butanoic acid (30) condensed with Calicheamicin N-acetyl gamma dimethyl hydrazide HPLC retention time: 6.1 min.
FAB MS: 1701 (M+H).
UV max at 273 nm (ethanol).

Example 59

4-(2-Acetylphenoxy)butanoic acid (31) condensed with Calicheamicin N-acetyl gamma dimethyl hydrazide HPLC retention time: 6.1 min.
FAB MS: 1683 (M+H).
UV—no maxima.

Example 60

2-Acetyl-10H-phenothiazine-10-hexanoic acid (32) condensed with Calicheamicin N-acetyl gamma dimethyl hydrazide HPLC retention time: 6.2 min.
FAB MS: 1833 (M+NH$_4$).
UV max at 281, strong shoulder at 356 nm (CH$_3$CN).

Example 61

4-Acetylphenylacetic acid (33) condensed with Calicheamicin N-acetyl gamma dimethyl hydrazide HPLC retention time: 5.0 min.
FAB MS: 1639 (M+H).

UV max at 281 nm (acetonitrile).

SYNTHESIS OF STRUCTURES C (SCHEME 1)
General Procedure

The carboxylic acid-hydrazones as obtained above are converted to the OSu esters ($Z^3$=N-succinimidyloxy) by dissolving them in an appropriate solvent such as acetonitrile or acetonitrile containing 10–20% N,N-dimethylforamide or tetrahydrofuran for better solubilization and adding ~2–5 equivalents of N-hydroxysuccinimide and ~2–10 equivalents of 1-(3-dimethylaminopropyl)-3-ethylcarbodiimide (EDCI) as the hydrochloride salt. The reaction is allowed to proceed at ambient temperature until complete as measured by HPLC or alternately by TLC, which is usually 1 to 8 hours. The solvents are then removed and the crude product is purified on an appropriate silica gel, such as BIOSIL A™, using an appropriate solvent system, such as a gradient of 0 to 20% methanol in either chloroform or ethyl acetate. The products are then sufficiently pure for the conjugation step.

Example 62

4-Formylphenoxyacetic acid (1) condensed with Calicheamicin N-acetyl gamma dimethyl hydrazide, N-hydroxysuccimide ester HPLC retention time: 6.5 min.

Example 63

4-Formylbenzoic acid (2) condensed with Calicheamicin N-acetyl gamma dimethyl hydrazide, N-hydroxysuccimide ester HPLC retention time: 6.6 min.
FAB MS: 1708 (M+H).
UV max at 310 nm (acetonitrile).

Example 64

4-Formyl-3-methoxyphenoxyacetic acid (3) condensed with Calicheamicin N-acetyl gamma dimethyl hydrazide, N-hydroxysuccimide ester HPLC retention time: 7.0 min.
FAB MS: 1768 (M+H).
UV max at 279, 288, and 320 nm (acetonitrile).

Example 65

6-Formyl-2-naphthoic acid (4) condensed with Calicheamicin N-acetyl gamma dimethyl hydrazide, N-hydroxysuccimide ester HPLC retention time: 7.4 min.
FAB MS: 1758 (M+H).
UV max at 272 and 323 nm (ethanol).

Example 66

4-(2-Oxoethoxy)benzenepropanoic acid (5) condensed with Calicheamicin N-acetyl gamma dimethyl hydrazide, N-hydroxysuccimide ester HPLC retention time: 7.1 min.
FAB MS: 1766 (M+H).

UV—no maxima.

Example 67

3-(2-Oxoethoxy)benzoic acid (6) condensed with Calicheamicin N-acetyl gamma dimethyl hydrazide, N-hydroxysuccimide ester HPLC retention time: 7.7 min.
UV—no maxima.

Figure 11:
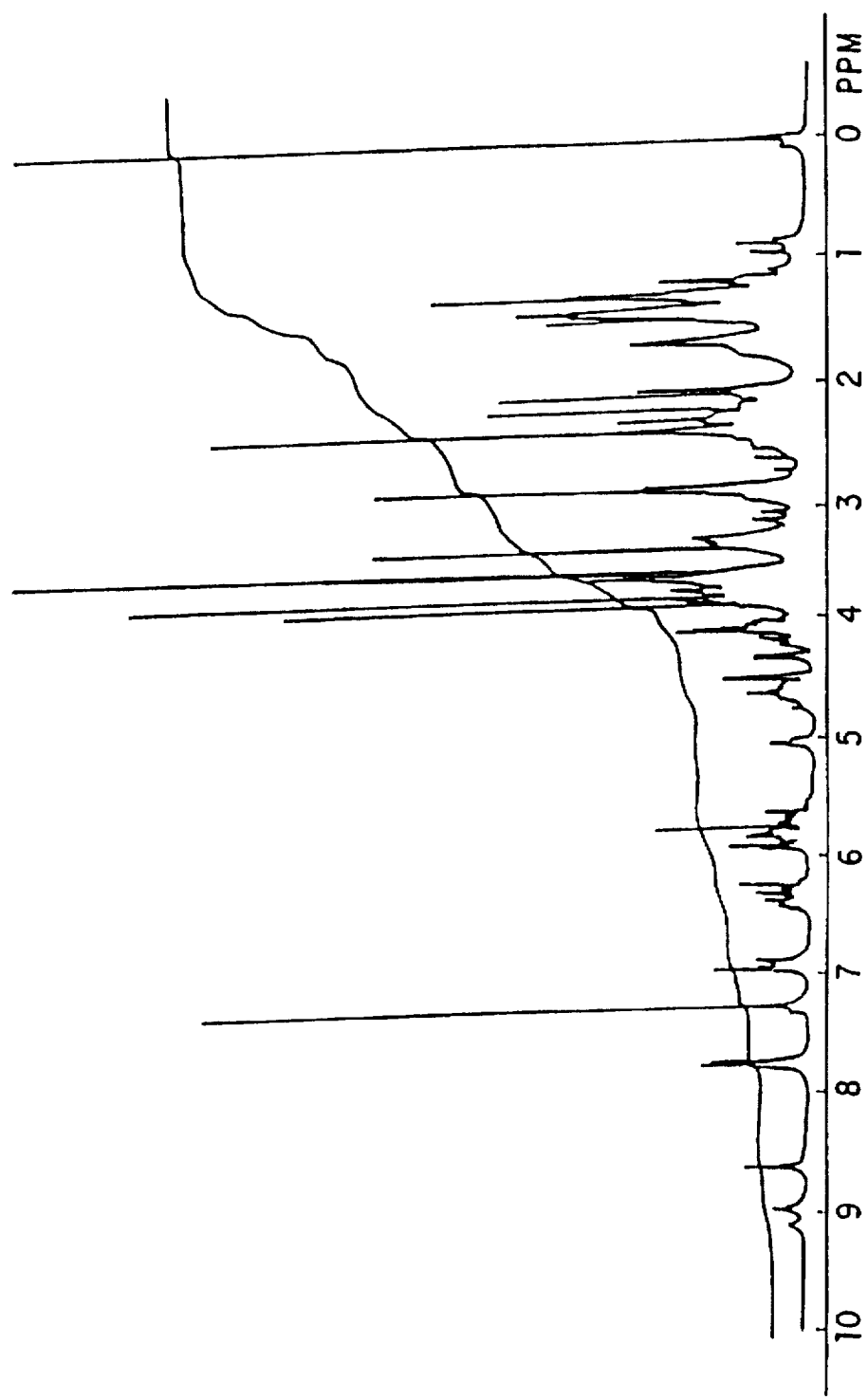
FIG. 11: The proton magnetic resonance spectrum of 4-(4-acetylphenoxy)butanoic acid condensed with Calicheamicin N-acetyl gamma dimethyl hydrazide, N-hydroxysuccinimide ester.

Example 68A 4-(4-Acetylphenoxy)butanoic acid (7) condensed with Calicheamicin N-acetyl gamma dimethyl hydrazide, N-hydroxysuccimide ester HPLC retention time: 7.5 min.
FAB MS: 1780 (M+H).
UV max at 283 nm (acetonitrile).
$^1$H-NMR: See FIG. 11.

Example 68B 4-(4-Acetylphenoxy)butanoic acid (7) condensed with Calicheamicin N-acetyl gamma dimethyl hydrazide, (1-hydroxy-2,5-dioxo-3-pyrrolidinesulfonic acid, monosodium salt) ester (i.e. ester with "sulfonato-N-hydroxysuccimide").

HPLC retention time: 5.2 min.
UV max at 278 nm (ethanol).

Example 69

4-(4-Acetylphenoxy)butanoic acid (7) condensed with calicheamicin gamma dimethyl hydrazide, N-hydroxysuccimide ester HPLC retention time: 7.6 min.
UV max at 283 nm (acetonitrile).

Example 70

4-(3-Formylphenoxy)butanoic acid (8) condensed with Calicheamicin N-acetyl gamma dimethyl hydrazide, N-hydroxysuccimide ester HPLC retention time: 7.4 min.
FAB MS: 1766 (M+H).
UV max at 283 nm (acetonitrile).

Example 71

4-(4-Formylphenoxy)butanoic acid (9) condensed with Calicheamicin N-acetyl gamma dimethyl hydrazide, N-hydroxysuccimide ester HPLC retention time: 7.0 min.
FAB MS: 1766 (M+H).
UV max at 289 nm (acetonitrile).

Example 72

4-(4-Acetyl-2-methylphenoxy)butanoic acid (10) condensed with Calicheamicin N-acetyl gamma dimethyl hydrazide, N-hydroxysuccimide ester HPLC retention time: 8.2 min.
FAB MS: 1794 (M+H).

Example 73

4-(4-Formyl-2-methoxyphenoxy)butanoic acid (11) condensed with Calicheamicin N-acetyl gamma dimethyl hydrazide, N-hydroxysuccimide ester HPLC retention time: 6.6 min.
FAB MS: 1796 (M+H).

Example 74

4-Formylbenzenepropanoic acid (12) condensed with Calicheamicin N-acetyl gamma dimethyl hydrazide, N-hydroxysuccimide ester HPLC retention time: 6.7 min.
FAB MS: 1736 (M+H).

Example 75

4-(2,3-Dimethoxy-5-formylphenoxy)butanoic acid (13) condensed with Calicheamicin N-acetyl gamma dimethyl hydrazide, N-hydroxysuccimide ester HPLC retention time: 6.7 min.
FAB MS: 1826 (M+H).
UV max at 298 nm (ethanol).

Example 76

4-(4-Acetyl-2,6-dimethoxyphenoxy)butanoic acid (14) condensed with Calicheamicin N-acetyl gamma dimethyl hydrazide, N-hydroxysuccimide ester HPLC retention time: 7.7 min.
FAB MS: 1840 (M+H).
UV max at 286 nm (acetonitrile).

Example 77

4-(4-Acetyl-2-methoxyphenoxy)butanoic acid (15) condensed with Calicheamicin N-acetyl gamma dimethyl hydrazide, N-hydroxysuccimide ester HPLC retention time: 7.2 min.
FAB MS: 1810 (M+H).
UV max at 284 nm (acetonitrile).

Example 78

4-[4-(3-Oxobutyl)phenoxy]butanoic acid (16) condensed with Calicheamicin N-acetyl gamma dimethyl hydrazide, N-hydroxysuccimide ester HPLC retention time: 7.9 min.
FAB MS: 1808 (M+H).
UV—no maxima.

Example 79

4-(2-Acetyl-5-methoxyphenoxy]butanoic acid (17) condensed with Calicheamicin N-acetyl gamma dimethyl hydrazide, N-hydroxysuccimide ester HPLC retention time: 7.4 min.
FAB MS: 1810 (M+H).
UV—no maxima.

Example 80

4-[4-(3-oxopropyl)phenoxy]butanoic acid (18) condensed with Calicheamicin N-acetyl gamma dimethyl hydrazide, N-hydroxysuccimide ester HPLC retention time: 13.1 min.
FAB MS: 1794 (M+H).
UV—no maxima.

Example 81

4-Acetylbenzenebutanoic acid (19) condensed with Calicheamicin N-acetyl gamma dimethyl hydrazide, N-hydroxysuccimide ester HPLC retention time: 7.7 min.

Example 82

4-[(2-Acetyl-1-naphthalenyl)oxy] butanoic acid (20) condensed with Calicheamicin N-acetyl gamma dimethyl hydrazide, N-hydroxysuccimide ester HPLC retention time: 9.4 min.
FAB MS: 1830 (M+H).
UV—no maxima.

Example 83

4-[4-(4-Fluorobenzoyl)phenoxy]butanoic acid (21) condensed with Calicheamicin N-acetyl gamma dimethyl hydrazide, N-hydroxysuccimide ester HPLC retention time: 9.3 min.
FAB MS: 1860 (M+H).
UV max at 284 nm (ethanol).

Example 84

4-(4-Acetylphenyl)-1-piperazinepentanoic acid (22) condensed with Calicheamicin N-acetyl gamma dimethyl hydrazide, N-hydroxysuccimide ester HPLC retention time: 6.3 min.
FAB MS: 1863 (M+H).
UV max at 306 nm (1:1 acetonitrile/chloroform).

Example 85

11-(4-Acetylphenoxy)undecanoic acid (23) condensed with Calicheamicin N-acetyl gamma dimethyl hydrazide, N-hydroxysuccimide ester HPLC retention time: 15.5 min.
FAB MS: 1878 (M+H).
UV max at 284 nm (ethanol).

Example 86

5-[(4-Acetylphenyl)amino]-5-oxopentanoic acid (24) condensed with Calicheamicin N-acetyl gamma dimethyl hydrazide, N-hydroxysuccimide ester HPLC retention time: 6.2 min.
FAB MS: 1807 (M+H).

Example 87

4-(2-Chloro-4-formylphenoxy)butanoic acid (25) condensed with Calicheamicin N-acetyl gamma dimethyl hydrazide, N-hydroxysuccimide ester HPLC retention time: 7.5 min.
FAB MS: 1800 (M+H).
UV max at 290 nm (acetonitrile).

Example 88

5-Acetyl-2-(3-carboxypropoxy)benzoic acid (26), methyl ester condensed with Calicheamicin N-acetyl gamma dimethyl hydrazide, N-hydroxysuccimide ester HPLC retention time: 7.2 min.
FAB MS: 1838 (M+H).
UV max at 284 nm (acetonitrile).

Example 89

4-(4-Formyl-2-nitrophenoxy)butanoic acid (27) condensed with Calicheamicin N-acetyl gamma dimethyl hydrazide, N-hydroxysuccimide ester HPLC retention time: 7.1 min.
FAB MS: 1811 (M+H).
UV max at 293 nm (ethanol).

Example 90

4-[2-[[(4-Acetylphenyl)amino]methyl]-6-methoxyphenoxy]butanoic acid (28) condensed with Calicheamicin N-acetyl gamma dimethyl hydrazide, N-hydroxysuccimide ester HPLC retention time: 9.2 min.
FAB MS: 1916 (M+H).
UV max at 309 nm (acetonitrile).

Example 91

4-(4-Acetyl-3-fluorophenoxy)butanoic acid (30) condensed with Calicheamicin N-acetyl gamma dimethyl hydrazide, N-hydroxysuccimide ester HPLC retention time: 8.2 min.
FAB MS: 1798 (M+H).
UV max at 270 nm (ethanol).

Example 92

4-(2-Acetylphenoxy)butanoic acid (31) condensed with Calicheamicin N-acetyl gamma dimethyl hydrazide, N-hydroxysuccimide ester HPLC retention time: 8.1 min.
FAB MS: 1780 (M+H).
UV—no maxima.

Example 93

2-Acetyl-10H-phenothiazine-10-hexanoic acid (32) condensed with Calicheamicin N-acetyl gamma dimethyl hydrazide, N-hydroxysuccimide ester HPLC retention time: 8.3 min.
FAB MS: 1930 (M+NH$_4$).
UV max at 292 nm (acetonitrile).

Example 94

4-Acetylphenylacetic acid (33) condensed with Calicheamicin N-acetyl gamma dimethyl hydrazide, N-hydroxysuccimide ester HPLC retention time: 7.2 min.
FAB MS: 1736 (M+H).
UV max at 280 nm (acetonitrile).

SYNTHESIS OF STRUCTURES D (METHOD A-SCHEME 1)

General Procedure

The activated ester from above is dissolved in an appropriate organic solvent, such as dimethylformamide, and added to a solution of antibody at ~1–15 mg/mL in an appropriate buffer, such as pH 7.4 phosphate (50 mM, 100 mM salt) such that the concentration of organic co-solvent is ~10–30% and ~2–10 equivalents of active ester are used per mole of antibody. The conjugation reaction is allowed to proceed at ambient temperature for ~4–24 hours. The solution is concentrated by use of a semipermeable membrane, if necessary, and purified by standard size-exclusion chromatography, such as with SEPHACRYL™ S-200 gel. The monomer fractions are pooled and the loading of drug on the antibody is estimated by UV-VIS absorbance at 280 nm for antibody and 333 nm or other appropriate wavelength for the calicheamicin hydrazones.

SYNTHESIS OF STRUCTURES E (SCHEME 2)

General Procedure

The carboxylic acids of the spacers are activated as the OSu esters ($Z^3$=N-succinimidyloxy) by dissolving them in an appropriate solvent such as tetrahydrofuran containing 10–20% dimethylformamide and adding ~2–3 equivalents of N-hydroxysuccinimide and ~2–5 equivalents of 1-(3-dimethylaminopropyl)-3-ethylcarbodiimide (EDCI) as the hydrochloride salt. The reaction is allowed to proceed at ambient temperature until complete as assessed by TLC, which is usually 1 to 8 hours. The solvents are then removed and the crude product is purified on an appropriate silica gel, such as BIOSIL A™, using an appropriate solvent system, such as a gradient of 0 to 5% methanol in chloroform. The products are generally purified further by recrystallization from a mixture of ethyl acetate-hexanes or other appropriate solvents.

The following preparations were made by the above procedure:

(SuOH=N-hydroxysuccinimide)

Preparation 95

4-Formylphenoxy acetic acid (1), N-hydroxysuccinimide ester

CI MS: 278 (MH$^+$), NMR (CDCl$_3$+D$_6$-DMSO): 9.9 ppm (1H, s, CH=O), 7.9 and 7.1 (2H each, d, ArH), 5.2 (2H, s, OCH$_2$), 2.9 (4H, s, CH$_2$CH$_2$).

Preparation 96

4-Formyl-3-methoxyphenoxy acetic acid (3), N-hydroxysuccinimide ester

CI MS: 308 (MH$^+$), NMR (CDCl$_3$): 10.3 ppm (1H, s, CH=O), 7.8 (1H, d, ArH), 6.6 (1H, dt, ArH), 6.55 (1H, d, ArH), 5.1 (2H, s, OCH$_2$), 3.95, (3H, s, OCH$_3$), 2.9 (4H, s, CH$_2$CH$_2$).

Preparation 97

4-(4-Acetylphenoxy)butanoic acid (7), N-hydroxysuccinimide ester

CI MS: 320 (MH$^+$), NMR (CDCl$_3$): 7.9 and 7.0 (2H each, d, ArH), 4.2 (2H, s, OCH$_2$), 2.9 (6H, m, CH$_2$CH$_2$+ O=CCH$_2$), 2.6 (3H, s, O=CCH$_3$), 2.3 (2H, m, CH$_2$).

SYNTHESIS OF STRUCTURES F (SCHEME 2)

General Procedure

The activated ester from above is dissolved in an appropriate organic solvent, such as N,N-dimethylformamide, and added to a solution of antibody at ~1–15 mg/mL in an appropriate buffer, such as pH 7.4 phosphate (50 mM, 100 mM salt) such that the concentration of organic co-solvent is ~10–25% and ~2–20 equivalents of active ester are used per mole of antibody. The conjugation reaction is allowed to proceed at ambient temperature for ~4–24 hours. The buffer is exchanged and the organic co-solvents and by-products are removed by use of a desalting column such as a PD-10 using pH 5.5 acetate buffer (25 mM acetate, 100 mM NaCl). The solution is concentrated by use of a semipermeable membrane, if necessary, and the product is used without further purification for the following step. The number of carbonyl groups incorporated per antibody is usually about half the number of equivalents of OSu ester used and can be further quantified by use of p-nitrophenyl hydrazine or other comparable method, if desired.

SYNTHESIS OF STRUCTURES D (METHOD B-SCHEME 2)

General Procedure

The drug hydrazide derivative is dissolved in an appropriate organic solvent, such as N,N-dimethylformamide, and added to a solution of antibody-linker conjugate (structure F) from the previous step at ~1–15 mg/mL in an appropriate buffer, such as pH acetate (25 mM, 100 mM salt) such that the concentration of organic co-solvent is ~10–15% and ~2–15 equivalents of hydrazide are used per mole of antibody. The conjugation reaction is allowed to proceed at ambient temperature for ~4–24 hours. The buffer is exchanged and the organic co-solvents and by-products are removed by use of a desalting column such as a PD-10 using pH 7.4 buffer (50 mM phosphate, 100 mM NaCl). The solution is concentrated by use of a semipermeable membrane, if necessary, and purified by standard size-exclusion chromatography, such as with SEPHACRYL™ S-200 gel. The monomer fractions are pooled and the loading of drug on the antibody is estimated by UV-VIS absorbence at 280 nm for antibody and 333 nm or other appropriate wavelength for the calicheamicin hydrazones.

Example 98 (Method A and B)

Conjugate of 4-formylphenoxyacetic acid (1) condensed with Calicheamicin N-acetyl gamma dimethyl hydrazide and h-P67.6

| Loading: 1.0 M/M, | Rel. Affinity: 0.65, |
|---|---|
| In vitro IC$_{50}$: 0.23 ng/mL, | Spec. Index: 1,600, |
| In vivo: 29% T/C (2 μg × 3 doses – 5/5 alive-28d), | |
| Ex vivo: 95% inhibition. | |

Example 99 (Method A and B)

Conjugate of 4-formylphenoxyacetic acid (1) condensed with Calicheamicin N-acetyl gamma dimethyl hydrazide and m-P67.6

| Loading: 1.5 M/M, | Rel. Affinity: 0.77, |
|---|---|
| In vitro IC$_{50}$: 0.068 ng/mL, | Spec. Index: 3,600, |
| Ex vivo: 90% inhibition. | |

Example 100 (Method A)

Conjugate of 4-formylphenoxyacetic acid (1) condensed with Calicheamicin N-acetyl gamma dimethyl hydrazide and m-CT-M-01

| Loading: 2.0 M/M, | Rel. Affinity: 0.84, |
|---|---|
| In vitro IC$_{50}$: 1.5 ng/mL, | Spec. Index: 59. |

Example 101 (Method A)

Conjugate of 4-formylbenzoic acid (2) condensed with Calicheamicin N-acetyl gamma dimethyl hydrazide and h-P67.6

| Loading: 4.8 M/M, | Rel. Affinity: 0.99, |
|---|---|
| In vitro IC$_{50}$: 4.8 ng/mL, | Spec. Index: >125, |
| Ex vivo: 63% inhibition. | |

Example 102 (Method A)

Conjugate of 4-formylbenzoic acid (2) condensed with Calicheamicin N-acetyl gamma dimethyl hydrazide and m-P67.6

| Loading: 4.0 M/M, | Rel. Affinity: 1.05, |
|---|---|
| In vitro IC$_{50}$: 4.0 ng/mL, | Spec. Index: >125. |

Example 103 (Method A)

Conjugate of 4-formylbenzoic acid (2) condensed with Calicheamicin N-acetyl gamma dimethyl hydrazide and m-CT-M-01

| Loading: 2.3 M/M, | Rel. Affinity: 0.90, |
|---|---|
| In vitro IC$_{50}$: 5.6 ng/mL, | Spec. Index: 32. |

Example 104 (Method A and B)

Conjugate of 4-formyl-3-methoxyphenoxyacetic acid (3) condensed with Calicheamicin N-acetyl gamma dimethyl hydrazide and h-P67.6

| Loading: 0.8 M/M, | Rel. Affinity: 0.81, |
|---|---|
| In vitro IC$_{50}$: 0.30 ng/mL, | Spec. Index: 375. |

Example 105 (Method A and B)

Conjugate of 4-formyl-3-methoxyphenoxyacetic acid (3) condensed with Calicheamicin N-acetyl gamma dimethyl hydrazide and m-P67.6

| | |
|---|---|
| Loading: 0.9 M/M, | Rel. Affinity: 0.76, |
| In vitro $IC_{50}$: 0.12 ng/mL, | Spec. Index: 1,200, |
| Ex vivo: 90% inhibition. | |

Example 106 (Method A)

Conjugate of 4-formyl-3-methoxyphenoxyacetic acid (3) condensed with Calicheamicin N-acetyl gamma dimethyl hydrazide and m-CT-M-01

| | |
|---|---|
| Loading: 2.1 M/M, | Rel. Affinity: 0.88, |
| In vitro $IC_{50}$: 5.6 ng/mL, | Spec. Index: 12. |

Example 107 (Method A)

Conjugate of 6-formyl-2-naphthoic acid (4) condensed with Calicheamicin N-acetyl gamma dimethyl hydrazide and m-P67.6

| | |
|---|---|
| Loading: 2.0 M/M, | Rel. Affinity: 0.73, |
| In vitro $IC_{50}$: 0.047 ng/mL, | Spec. Index: 675. |

Example 108 (Method A)

Conjugate of 4-(2-oxoethoxy)benzenepropanoic acid (5) condensed with Calicheamicin N-acetyl gamma dimethyl hydrazide and h-P67.6

| | |
|---|---|
| Loading: 1.1 M/M, | Rel. Affinity: 1.09, |
| In vitro $IC_{50}$: 2.22 ng/mL, | Spec. Index: 125. |

Example 109 (Method A)

Conjugate of 4-(2-oxoethoxy)benzenepropanoic acid (5) condensed with Calicheamicin N-acetyl gamma dimethyl hydrazide and m-P67.6

| | |
|---|---|
| Loading: 0.6 M/M, | Rel. Affinity: 1.11, |
| In vitro $IC_{50}$: 0.45 ng/mL, | Spec. Index: 200, |
| Ex vivo: 71% inhibition. | |

Example 110 (Method A)

Conjugate of 3-(2-oxoethoxy)benzoic acid (6) condensed with Calicheamicin N-acetyl gamma dimethyl hydrazide and h-P67.6

| | |
|---|---|
| Loading: 1.3 M/M, | Rel. Affinity: 1.19, |
| In vitro $IC_{50}$: 0.69 ng/mL, | Spec. Index: 100. |

Example 111 (Method A)

Conjugate of 3-(2-oxoethoxy)benzoic acid (6) condensed with Calicheamicin N-acetyl gamma dimethyl hydrazide and m-P67.6

| | |
|---|---|
| Loading: 0.8 M/M, | Rel. Affinity: 1.91, |
| In vitro $IC_{50}$: 0.32 ng/mL, | Spec. Index: 175. |

Example 112 (Method A)

Conjugate of 4-(4-acetylphenoxy)butanoic acid (7) condensed with Calicheamicin N-acetyl gamma dimethyl hydrazide and h-P67.6

| | |
|---|---|
| Loading: 2.7 M/M, | Rel. Affinity: 0.75, |
| In vitro $IC_{50}$: 0.098 ng/mL, | Spec. Index: 6,400, |
| In vivo: 0% T/C (1 µg × 3 doses, 5/5 alive-28d), | |
| 0% T/C (3 µg × 3 doses, 5/5 alive-28d), | |
| 0% T/C (6 µg × 3 doses, 5/5 alive-28d), | |
| Ex vivo: 96% inhibition. | |

Example 113 (Method A)

Conjugate of 4-(4-acetylphenoxy)butanoic acid (7) condensed with calicheamicin gamma dimethyl hydrazide and h-P67.6

| | |
|---|---|
| Loading: 3.2 M/M, | Rel. Affinity: 0.78 |
| In vitro $IC_{50}$: 0.001 ng/mL, | Spec. Index: 10,000 |

Example 114 (Method A or B)

Conjugate of 4-(4-acetylphenoxy)butanoic acid (7) condensed with Calicheamicin N-acetyl gamma dimethyl hydrazide and m-P67.6

| | |
|---|---|
| Loading: 1.7 M/M, | Rel. Affinity: 0.96, |
| In vitro $IC_{50}$: 0.017 ng/mL, | Spec. Index: 29,500, |
| In vivo: 22% T/C (0.5 µg × 3 doses, 5/5 alive-28d), | |
| 0% T/C (1 µg × 3 doses, 5/5 alive-28d), | |
| 1% T/C (3 µg × 3 doses, 5/5 alive-28d), | |
| 0% T/C (6 µg × 3 doses, 2/5 alive-28d), | |
| Ex vivo: 98% inhibition. | |

Example 115 (Method A)

Conjugate of 4-(4-acetylphenoxy)butanoic acid (7) condensed with Calicheamicin N-acetyl gamma dimethyl hydrazide and h-CT-M-01

| | |
|---|---|
| Loading: 3.4 M/M, | Rel. Affinity: not determined, |
| In vitro $IC_{50}$: 0.048 ng/mL, | Spec. Index: 6,200. |

Example 116 (Method A)

Conjugate of 4-(4-acetylphenoxy)butanoic acid (7) condensed with calicheamicin N-acetyl gamma dimethyl hydrazide and m-A33

| | |
|---|---|
| Loading: 1.1 M/M | Rel. Affinity: 0.68, |
| In vitro IC$_{50}$: 3.32 ng/mL, | Spec. Index: 0.72. |
| In vivo: 4% T/C (3 μg × 3 doses, 5/5 alive-28d), | |
| 5% T/C (6 μg × 3 doses, 5/5 alive-28d). | |

Example 117 (Method A)

Conjugate of 4-(4-acetylphenoxy)butanoic acid (7) condensed with calicheamicin N-acetyl gamma dimethyl hydrazide and h-A33

| | |
|---|---|
| Loading: 1.8 M/M | Rel. Affinity: 1.13, |
| In vitro IC$_{50}$: 4.03 ng/mL, | Spec. Index: 0.96. |

Example 118 (Method A)

Conjugate of 4-(4-acetylphenoxy)butanoic acid (7) condensed with calicheamicin gamma dimethyl hydrazide and h-A33

| | |
|---|---|
| Loading: 2.8 M/M, | Rel. Affinity: 0.91, |
| In vitro IC$_{50}$: 3.55 ng/mL, | Spec. Index: 2.6. |

Example 119 (Method A)

Conjugate of 4-(4-acetylphenoxy)butanoic acid (7) condensed with calicheamicin N-acetyl gamma dimethyl hydrazide and anti-Tac

| | |
|---|---|
| Loading: 2.1 M/M, | Rel. Affinity: not determined, |
| In vitro IC$_{50}$: 0.004 ng/mL, | Spec. Index: 250, |
| Ex vivo: IC$_{50}$: 1.0 ng/mL, | Spec. Index: 100. |

Example 120 (Method A)

Conjugate of 4-(3-formylphenoxy)butanoic acid (8) condensed with Calicheamicin N-acetyl gamma dimethyl hydrazide and m-P67.6

| | |
|---|---|
| Loading: 1.7 M/M, | Rel. Affinity: 1.00, |
| In vitro IC$_{50}$: 0.38 ng/mL, | Spec. Index: 1,700. |

Example 121 (Method A)

Conjugate of 4-(4-formylphenoxy)butanoic acid (9) condensed with Calicheamicin N-acetyl gamma dimethyl hydrazide and h-P67.6

| | |
|---|---|
| Loading: 2.8 M/M, | Rel. Affinity: 0.56, |
| In vitro IC$_{50}$: 0.52 ng/mL, | Spec. Index: 2,900, |
| In vivo: 12% T/C (1 μg × 3 doses, 5/5 alive-28d), | |
| 9% T/C (3 μg × 3 doses, 5/5 alive-28d), | |
| 3% T/C (6 μg × 3 doses, 4/5 alive-28d), | |
| Ex vivo: 98% inhibition. | |

Example 122 (Method A)

Conjugate of 4-(4-formylphenoxy)butanoic acid (9) condensed with Calicheamicin N-acetyl gamma dimethyl hydrazide and m-P67.6

| | |
|---|---|
| Loading: 1.8 M/M, | Rel. Affinity: 0.70, |
| In vitro IC$_{50}$: 0.087 ng/mL, | Spec. Index: 11,000, |
| In vivo: 17% T/C (0.5 μg × 3 doses, 5/5 alive-28d), | |
| 23% T/C (1 μg × 3 doses, 5/5 alive-28d), | |
| 9% T/C (3 μg × 3 doses, 5/5 alive-28d), | |
| 0% T/C (6 μg × 3 doses, 5/5 alive-28d). | |

Example 123 (Method A)

Conjugate of 4-(4-acetyl-2-methylphenoxy)butanoic acid (10) condensed with Calicheamicin N-acetyl gamma dimethyl hydrazide and h-P67.6

| | |
|---|---|
| Loading: 3.5 M/M, | Rel. Affinity: 1.16, |
| In vitro IC$_{50}$: 0.45 ng/mL, | Spec. Index: 2,900. |

Example 124 (Method A)

Conjugate of 4-(4-acetyl-2-methylphenoxy)butanoic acid (10) condensed with Calicheamicin N-acetyl gamma dimethyl hydrazide and m-P67.6

| | |
|---|---|
| Loading: 1.6 M/M, | Rel. Affinity: 1.07, |
| In vitro IC$_{50}$: 0.041 ng/mL, | Spec. Index: 5,100. |

Example 125 (Method A)

Conjugate of 4-(4-formyl-2-methoxyphenoxy)butanoic acid (11) condensed with Calicheamicin N-acetyl gamma dimethyl hydrazide and h-P67.6

| | |
|---|---|
| Loading: 2.6 M/M, | Rel. Affinity: 0.73, |
| In vitro IC$_{50}$: 3.8 ng/mL, | Spec. Index: 575. |

Example 126 (Method A)

Conjugate of 4-(4-formyl-2-methoxyphenoxy)butanoic acid (11) condensed with Calicheamicin N-acetyl gamma dimethyl hydrazide and m-P67.6

| | |
|---|---|
| Loading: 1.9 M/M, | Rel. Affinity: 0.22, |
| In vitro IC$_{50}$: 0.13 ng/mL, | Spec. Index: 1,800. |

Example 127 (Method A)

Conjugate of 4-formylbenzenepropanoic acid (12) condensed with Calicheamicin N-acetyl gamma dimethyl hydrazide and h-P67.6

| | |
|---|---|
| Loading: 2.5 M/M, | Rel. Affinity: 0.73, |
| In vitro $IC_{50}$: 1.0 ng/mL, | Spec. Index: 950. |

Example 128 (Method A)

Conjugate of 4-formylbenzenepropanoic acid (12) condensed with Calicheamicin N-acetyl gamma dimethyl hydrazide and m-P67.6

| | |
|---|---|
| Loading: 1.6 M/M, | Rel. Affinity: 0.73, |
| In vitro $IC_{50}$: 0.12 ng/mL, | Spec. Index: 2,000. |

Example 129 (Method A)

Conjugate of 4-(2,3-dimethoxy-5-formylphenoxy) butanoic acid (13) condensed with Calicheamicin N-acetyl gamma dimethyl hydrazide and h-P67.6

| | |
|---|---|
| Loading: 1.0 M/M, | Rel. Affinity: 1.16, |
| In vitro $IC_{50}$: 1.1 ng/mL, | Spec. Index: >375. |

Example 130 (Method A)

Conjugate of 4-(2,3-Dimethoxy-5-formylphenoxy) butanoic acid (13) condensed with Calicheamicin N-acetyl gamma dimethyl hydrazide and m-P67.6

| | |
|---|---|
| Loading: 1.8 M/M, | Rel. Affinity: 1.08, |
| In vitro $IC_{50}$: 0.062 ng/mL, | Spec. Index: >9,800. |

Example 131 (Method A)

Conjugate of 4-(4-acetyl-2,6-dimethoxyphenoxy) butanoic acid (14) condensed with Calicheamicin N-acetyl gamma dimethyl hydrazide and h-P67.6

| | |
|---|---|
| Loading: 2.6 M/M, | Rel. Affinity: 1.07, |
| In vitro $IC_{50}$: 0.24 ng/mL, | Spec. Index: >1,700. |

Example 132 (Method A)

Conjugate of 4-(4-acetyl-2,6-dimethoxyphenoxy) butanoic acid (14) condensed with Calicheamicin N-acetyl gamma dimethyl hydrazide and m-P67.6

| | |
|---|---|
| Loading: 1.7 M/M, | Rel. Affinity: 1.18, |
| In vitro $IC_{50}$: 0.015 ng/mL, | Spec. Index: >40,500. |

Example 133 (Method A)

Conjugate of 4-(4-acetyl-2-methoxyphenoxy) butanoic acid (15) condensed with Calicheamicin N-acetyl gamma dimethyl hydrazide and h-P67.6

| | |
|---|---|
| Loading: 2.3 M/M, | Rel. Affinity: 0.78, |
| In vitro $IC_{50}$: 0.23 ng/mL, | Spec. Index: 875. |

Example 134 (Method A)

Conjugate of 4-(4-acetyl-2-methoxyphenoxy) butanoic acid (15) condensed with Calicheamicin N-acetyl gamma dimethyl hydrazide and m-P67.6

| | |
|---|---|
| Loading: 1.7 M/M, | Rel. Affinity: 0.80, |
| In vitro $IC_{50}$: 0.029 ng/mL, | Spec. Index: 13,500. |

Example 135 (Method A)

Conjugate of 4-[4-(3-oxobutyl)phenoxy]butanoic acid (16) condensed with Calicheamicin N-acetyl gamma dimethyl hydrazide and m-P67.6

| | |
|---|---|
| Loading: 0.5 M/M, | Rel. Affinity: not determined, |
| In vitro $IC_{50}$: 9 ng/mL, | Spec. Index: 2. |

Example 136 (Method A)

Conjugate of 4-(2-acetyl-5-methoxyphenoxy] butanoic acid (17) condensed with Calicheamicin N-acetyl gamma dimethyl hydrazide and h-P67.6

| | |
|---|---|
| Loading: 2.3 M/M, | Rel. Affinity: 0.98, |
| In vitro $IC_{50}$: 0.088 ng/mL, | Spec. Index: 1,100. |

Example 137 (Method A)

Conjugate of 4-(2-acetyl-5-methoxyphenoxy] butanoic acid (17) condensed with Calicheamicin N-acetyl gamma dimethyl hydrazide and m-P67.6

| | |
|---|---|
| Loading: 1.6 M/M, | Rel. Affinity: 1.20, |
| In vitro $IC_{50}$: 0.0098 ng/mL, | Spec. Index: 21,500. |

Example 138 (Method A)

Conjugate of 4-[4-(3-oxopropyl)phenoxy]butanoic acid (18) condensed with Calicheamicin N-acetyl gamma dimethyl hydrazide and h-P67.6

| | |
|---|---|
| Loading: 1.0 M/M, | Rel. Affinity: 0.80, |
| In vitro $IC_{50}$: 1.1 ng/mL, | Spec. Index: 80. |

Example 139 (Method A)

Conjugate of 4-[4-(3-oxopropyl)phenoxy]butanoic acid (18) condensed with Calicheamicin N-acetyl gamma dimethyl hydrazide and m-P67.6

| | |
|---|---|
| Loading: 0.6 M/M, | Rel. Affinity: 1.21, |
| In vitro $IC_{50}$: 0.62 ng/mL, | Spec. Index: 90. |

Example 140 (Method A)

Conjugate of 4-acetylbenzenebutanoic acid (19) condensed with Calicheamicin N-acetyl gamma dimethyl hydrazide and h-P67.6

| | |
|---|---|
| Loading: 2.6 M/M, | Rel. Affinity: 0.50, |
| In vitro $IC_{50}$: 0.012 ng/mL, | Spec. Index: 2,600, |
| In vivo: 23% T/C (0.5 μg × 3 doses, 5/5 alive-28d), | |
| 10% T/C (1 μg × 3 doses, 5/5 alive-28d), | |
| 4% T/C (3 μg × 3 doses, 4/5 alive-28d), | |
| 0% T/C (6 μg × 3 doses, 2/5 alive-28d), | |
| Ex vivo: 99% inhibition. | |

Example 141 (Method A)

Conjugate of 4-acetylbenzenebutanoic acid (19) condensed with Calicheamicin N-acetyl gamma dimethyl hydrazide and m-P67.6

| | |
|---|---|
| Loading: 2.2 M/M, | Rel. Affinity: 0.42, |
| In vitro $IC_{50}$: 0.0082 ng/mL, | Spec. Index: 31,500, |
| In vivo: 21% T/C (0.5 μg × 3 doses, 5/5 alive-28d), | |
| 25% T/C (1 μg × 3 doses, 5/5 alive-28d), | |
| 0% T/C (3 μg × 3 doses, 4/5 alive-28d), | |
| 0% T/C (6 μg × 3 doses, 1/5 alive-28d), | |
| Ex vivo: 99% inhibition. | |

Example 142 (Method A)

Conjugate of 4-[(2-acetyl-1-naphthalenyl)oxy]butanoic acid (20) condensed with Calicheamicin N-acetyl gamma dimethyl hydrazide and h-P67.6

| | |
|---|---|
| Loading: 2.5 M/M, | Rel. Affinity: 0.50, |
| In vitro $IC_{50}$: 0.061 ng/mL, | Spec. Index: 5,000, |
| In vivo: 36% T/C (1 μg × 3 doses, 5/5 alive-28d), | |
| 22% T/C (3 μg × 3 doses, 5/5 alive-28d), | |
| 11% T/C (6 μg × 3 doses, 4/5 alive-28d), | |
| Ex vivo: 76% inhibition. | |

Example 143 (Method A)

Conjugate of 4-[(2-acetyl-1-naphthalenyl)oxy]butanoic acid (20) condensed with Calicheamicin N-acetyl gamma dimethyl hydrazide and m-P67.6

| | |
|---|---|
| Loading: 1.8 M/M, | Rel. Affinity: 0.66, |
| In vitro $IC_{50}$: 0.0067 ng/mL, | Spec. Index: 105,000. |

Example 144 (Method A)

Conjugate of 4-[4-(4-fluorobenzoyl)phenoxy]butanoic acid (21) condensed with Calicheamicin N-acetyl gamma dimethyl hydrazide and h-P67.6

| | |
|---|---|
| Loading: 2.5 M/M, | Rel. Affinity: 0.67, |
| In vitro $IC_{50}$: 99 ng/mL, | Spec. Index: 3. |

Example 145 (Method A)

Conjugate of 4-(4-(4-fluorobenzoyl)phenoxy]butanoic acid (21) condensed with Calicheamicin N-acetyl gamma dimethyl hydrazide and h-P67.6

| | |
|---|---|
| Loading: 1.8 M/M, | Rel. Affinity: 0.76, |
| In vitro $IC_{50}$: 63 ng/mL, | Spec. Index: 9. |

Example 146 (Method A)

Conjugate of 4-(4-acetylphenyl)-1-piperazinepentanoic acid (22) condensed with Calicheamicin N-acetyl gamma dimethyl hydrazide and h-P67.6

| | |
|---|---|
| Loading: 0.1 M/M, | Rel. Affinity: 0.98, |
| In vitro $IC_{50}$: 12 ng/mL, | Spec. Index: 2. |

Example 147 (Method A)

Conjugate of 11-(4-acetylphenoxy)undecanoic acid (23) condensed with Calicheamicin N-acetyl gamma dimethyl hydrazide and h-P67.6

| | |
|---|---|
| Loading: 0.5 M/M, | Rel. Affinity: 0.80, |
| In vitro $IC_{50}$: 0.43 ng/mL, | Spec. Index: 175. |

Example 148 (Method A)

Conjugate of 11-(4-acetylphenoxy)undecanoic acid (23) condensed with Calicheamicin N-acetyl gamma dimethyl hydrazide and m-P67.6

| | |
|---|---|
| Loading: 0.4 M/M, | Rel. Affinity: 1.16, |
| In vitro $IC_{50}$: 0.47 ng/mL, | Spec. Index: 125. |

Example 149 (Method A)

Conjugate of 5-[(4-acetylphenyl)amino]-5-oxopentanoic acid (24) condensed with Calicheamicin N-acetyl gamma dimethyl hydrazide and m-P67.6

| | |
|---|---|
| Loading: 2.0 M/M, | Rel. Affinity: 0.73, |
| In vitro $IC_{50}$: <0.005 ng/mL, | Spec. Index: >1,200. |

Example 150 (Method A)

Conjugate of 4-(2-chloro-4-formylphenoxy)butanoic acid (25) condensed with Calicheamicin N-acetyl gamma dimethyl hydrazide and h-P67.6

| Loading: 2.0 M/M, | Rel. Affinity: 0.31, |
|---|---|
| In vitro $IC_{50}$: 0.0071 ng/mL, | Spec. Index: 1,500. |

Example 151 (Method A)

Conjugate of 5-acetyl-2-(3-carboxypropoxy)benzoic acid (26), methyl ester condensed with Calicheamicin N-acetyl gamma dimethyl hydrazide and h-P67.6

| Loading: 2.0 M/M, | Rel. Affinity: 0.79, |
|---|---|
| In vitro $IC_{50}$: <0.005 ng/mL, | Spec. Index: >9,600. |

Example 152 (Method A)

Conjugate of 4-(4-formyl-2-nitrophenoxy)butanoic acid (27) condensed with Calicheamicin N-acetyl gamma dimethyl hydrazide and h-P67.6

| Loading: 1.5 M/M, | Rel. Affinity: 1.3, |
|---|---|
| In vitro $IC_{50}$: 0.023 ng/mL, | Spec. Index: >4,500. |

Example 153 (Method A)

Conjugate of 4-[2-[[(4-acetylphenyl)amino]methyl]-6-methoxyphenoxy]butanoic acid (28) condensed with Calicheamicin N-acetyl gamma dimethyl hydrazide and h-P67.6

| Loading: 2.0 M/M, | Rel. Affinity: 0.85, |
|---|---|
| In vitro $IC_{50}$: <0.005 ng/mL, | Spec. Index: >5,000. |

Example 154 (Method A)

Conjugate of 4-(4-acetyl-3-fluorophenoxy)butanoic acid (30) condensed with Calicheamicin N-acetyl gamma dimethyl hydrazide and h-P67.6

| Loading: 1.5 M/M, | Rel. Affinity: 1.01, |
|---|---|
| In vitro $IC_{50}$: 0.005 ng/mL, | Spec. Index: 4,800. |

Example 155 (Method A)

Conjugate of 4-(2-Acetylphenoxy)butanoic acid (31) condensed with Calicheamicin N-acetyl gamma dimethyl hydrazide and h-P67.6

| Loading: 1.5 M/M, | Rel. Affinity: 0.95, |
|---|---|
| In vitro $IC_{50}$: <0.005 ng/mL, | Spec. Index: >7,000. |

Example 156 (Method A)

Conjugate of 2-acetyl-10H-phenothiazine-10-hexanoic acid (32) condensed with Calicheamicin N-acetyl gamma dimethyl hydrazide and h-P67.6

| Loading: 1.5 M/M, | Rel. Affinity: 1.25, |
|---|---|
| In vitro $IC_{50}$: 0.021 ng/mL, | Spec. Index: 2,300. |

Example 157 (Method A)

Conjugate of 4-acetylphenylacetic acid (33) condensed with Calicheamicin N-acetyl gamma dimethyl hydrazide and h-P67.6

| Loading: 1.4 M/M, | Rel. Affinity: 0.91, |
|---|---|
| In vitro $IC_{50}$: <0.005 ng/mL, | Spec. Index: 4,700. |

The described conjugates are useful for inhibiting the growth of unwanted cells which is an important part of the invention. Accordingly, the invention also includes pharmaceutical compositions, most preferably a parenteral composition suitable for injection into the body of a warm-blooded mammal. Such compositions are formulated by methods which are commonly used in pharmaceutical chemistry. The conjugates are acceptably soluble in physiologically-acceptable fluids, such as physiological saline solutions and other aqueous solutions which can safely be administered parenterally.

Products for parenteral administration are often formulated and distributed in solid, preferably freeze-dried form, for reconstitution immediately before use. Such formulations are useful compositions of the present invention. Their preparation is well understood by pharmaceutical chemists; in general, they comprise mixtures of inorganic salts, to confer isotonicity, and dispersing agents, such as sucrose, to allow the dried preparation to dissolve quickly upon reconstitution. Such formulations are reconstituted with highly purified water or physiologically acceptable buffers to a known concentration, based on the drug. A preferred freeze-dried pharmaceutical composition for inhibiting the growth of cells is obtained by freeze-drying an approximately 1 mg/ml solution of the conjugate dissolved in about 5 mM sodium phosphate buffer at a pH of about 7.4 containing about 100 mM sodium chloride and about 100 mM sucrose. For the conjugate, which has the formula $Z^3[CO-Alk^1-Sp^1-Ar-Sp^2-Alk^2-C(Z^1)=Z^2]m$. $Z^3$ is preferably antibody h-CT-M-01 or h-p67.6; $Alk^1$ is preferably $C_4$ alkylene; $Sp^1$ is preferably —O—; Ar is preferably 1,4-phenylene; $Alk^2$ and $Sp^2$ preferably are together a bond; $Z^1$ is preferably $C_1$ alkyl; and $Z^2$ is preferably calicheamicin N-acetyl gamma dimethyl hydrazide.

The optimum dosage and administration schedule of conjugates of the invention must be determined by the treating physician, in light of the patient's condition.

It is customary, of course, to administer cytotoxic drugs in the form of divided doses, with intervals of days or weeks between each series of doses. The conjugates are effective over a wide dosage range, and dosages per week will usually fall within the range from about 1 to about 10,000 µg/m² of drug, more preferably in the range from about 10 to about 200 µg/m².

We claim:

1. A compound of the formula:

Z³CO-Alk¹-Sp¹-Ar-Sp²-Alk²-C(Z¹)=O wherein

Ar is a 1,2-, 1,8-, or 2,7-naphthylidene or

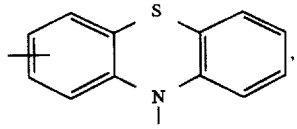

each naphthylidene or phenothiazine optionally substituted with one, two, three, or four groups of $(C_1-C_6)$ alkyl, $(C_1-C_5)$ alkoxy, $(C_1-C_4)$ thioalkoxy, halogen, nitro, or COOR', CONHR', O(CH₂)ₙCOOR', S(CH₂)ₙCOOR', O(CH₂)ₙCONHR', or S(CH₂)ₙCONHR' wherein n is an integer from 0 to 5 and R' is a branched or unbranched $(C_1-C_5)$ chain optionally substituted by one or two groups of —OH, $(C_1-C_4)$ alkoxy, $(C_1-C_4)$ thioalkoxy, halogen, nitro, $(C_1-C_3)$ dialkylamino, or $(C_1-C_3)$ trialkylammonium—A⁻ where A⁻ is a pharmaceutically acceptable anion completing a salt;

Z³ is halogen, hydroxy, OM wherein M is a metal completing a salt, —N₃,

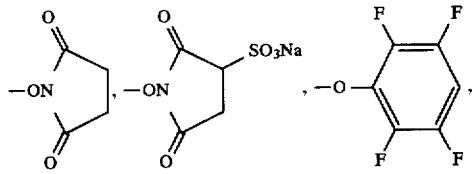

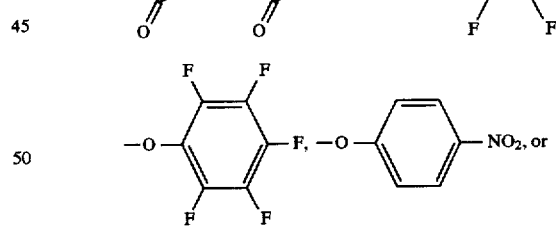

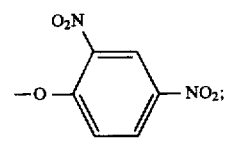

Alk¹ and Alk² are independently a bond or branched or unbranched $(C_1-C_{10})$ alkylene chain;

Sp¹ is a bond, —S—, —O—, —CONH—, —NHCO—, —NR'—, —N(CH₂CH₂)₂N—, or —X—Ar'—Y—(CH₂)ₙ—Z wherein X, Y, and Z are independently a bond, —NR'—, —S—, or —O—, with the proviso that when n=0, then at least one of Y and Z must be a bond, and Ar' is 1,2-, 1,3-, or 1,4-phenylene optionally substituted with one, two, or three groups of ($C_1$–$C_5$) alkyl, ($C_1$–$C_4$) alkoxy, ($C_1$–$C_4$) thioalkoxy, halogen, nitro, COOR', CONHR', O($CH_2$)$_n$COOR', S($CH_2$)$_n$COOR', O($CH_2$)$_n$CONHR', or S($CH_2$)$_n$CONHR' wherein n and R' are as hereinbefore defined, with the proviso that when $Alk^1$ is a bond, then $Sp^1$ is a bond and with the proviso that when Ar is phenothiazine, $Sp^1$ is a bond only connected to nitrogen and $Alk^1$ is not a bond;

$Sp^2$ is a bond, —S—, or —O—, with the proviso that when $Alk^2$ is a bond, $Sp^2$ is a bond;

$Z^1$ is H, ($C_1$–$C_5$) alkyl, or phenyl optionally substituted with one, two, or three groups of ($C_1$–$C_5$) alkyl, ($C_1$–$C_4$) alkoxy, ($C_1$–$C_4$) thioalkoxy, halogen, nitro, COOR', CONHR', O($CH_2$)$_n$COOR', S($CH_2$)$_n$COOR', O($CH_2$)$_n$CONHR', or S($CH_2$)$_n$CONHR' wherein n and R' are as hereinbefore defined, with the proviso that when Ar is naphthylidene, $Z^1$ is not hydrogen and with the proviso that when $Alk^1$ is a bond, $Sp^2$ is a bond, and $Alk^2$ is not a bond, then $Z^1$ is not $C_1$ alkyl.

2. A compound according to claim 1, wherein $Z^1$ is H or ($C_1$–$C_5$) alkyl and $Sp^2$ and $Alk^2$ are each a bond.

3. A compound according to claim 2, wherein $Sp^1$ is a bond, —S—, —O—, —CONH—, —NHCO—, —NR'—, or —N($CH_2CH_2$)$_2$N— and $Alk^1$ is a branched or unbranched ($C_1$–$C_{10}$) alkylene chain.

4. A compound according to claim 3, wherein

Ar is an unsubstituted 1,2-, 1,8-, or 2,7-naphthylidene or

5. A compound according to claim 4, wherein $Z^3$ is hydroxy,

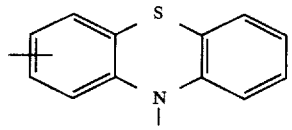

6. A compound of the formula:

$Z^3CO$-$Alk^1$-$Sp^1$-Ar-$Sp^2$-$Alk^2$-$C(Z^1)$=O wherein

Ar is 1,2-, 1,3-, or 1,4-phenylene optionally substituted with one, two, or three groups of ($C_1$–$C_6$) alkyl, ($C_1$–$C_5$) alkoxy, ($C_1$–$C_4$) thioalkoxy, halogen, nitro, or COOR', CONHR', O($CH_2$)$_n$COOR', S($CH_2$)$_n$COOR', O($CH_2$)$_n$CONHR', or S($CH_2$)$_n$CONHR' wherein n is an integer from 0 to 5 and R' is a branched or unbranched ($C_1$–$C_5$) chain optionally substituted by one or two groups of —OH, ($C_1$–$C_4$) alkoxy, ($C_1$–$C_4$) thioalkoxy, halogen, nitro, ($C_1$–$C_3$) dialkylamino, or ($C_1$–$C_3$) trialkylammonium—A$^-$ where A$^-$ is a pharmaceutically acceptable anion completing a salt;

$Z^3$ is halogen, hydroxy, OM wherein M is a metal completing a salt, —$N_3$,

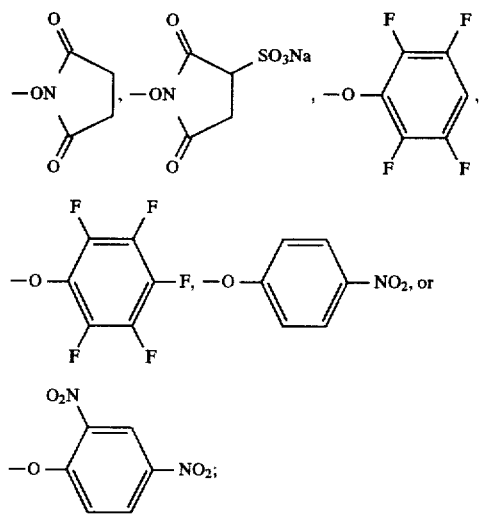

$Alk^1$ and $Alk^2$ are, independently, a branched or unbranched ($C_1$–$C_{10}$) alkylene chain.

$Sp^1$ is a bond, —S—, —O—, —CONH—, —NHCO—, —NR'—, —N($CH_2CH_2$)$_2$N—, or —X—Ar'—Y—($CH_2$)$_n$—Z wherein X, Y, and Z are independently a bond, —NR'—, —S—, or —O—, with the proviso that when n=0, then at least one of Y and Z must be a bond, and Ar' is 1,2-, 1,3-, or 1,4-phenylene optionally substituted with one, two, or three groups of ($C_1$–$C_5$) alkyl, ($C_1$–$C_4$) alkoxy, ($C_1$–$C_4$) thioalkoxy, halogen, nitro, COOR', CONHR', O($CH_2$)$_n$COOR', S($CH_2$)$_n$COOR', O($CH_2$)$_n$CONHR', or S($CH_2$)$_n$CONHR', wherein n and R' are as hereinbefore defined;

$Sp^2$ is a bond, —S—, or —O—, with the proviso that $Sp^1$ and $Sp^2$ are not both simultaneously a bond;

$Z^1$ is phenyl optionally substituted with one, two, or three groups of ($C_1$–$C_5$) alkyl, ($C_1$–$C_4$) alkoxy, ($C_1$–$C_4$) thioalkoxy, halogen, nitro, COOR', CONHR', O($CH_2$)$_n$COOR', S($CH_2$)$_n$COOR', O($CH_2$)$_n$CONHR', or S($CH_2$)$_n$CONHR' wherein n and R' are as hereinbefore defined.

7. A compound according to claim 6, wherein $Sp^1$ is a bond, —S—, —O—, —CONH—, —NHCO—, —NR'—, or —N($CH_2CH_2$)$_2$N—.

8. A compound according to claim 7, wherein Ar is unsubstituted 1,2-, 1,3-, or 1,4-phenylene.

9. A compound according to claim 8, wherein $Z^1$ is unsubstituted phenyl.

10. A compound according to claim 9, wherein $Z^3$ is hydroxy,

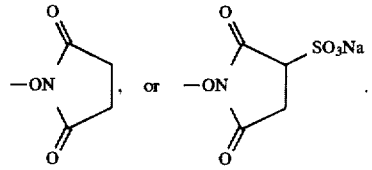

11. A compound of the formula:

$Z^3CO$-$Alk^1$-$Sp^1$-Ar-$Sp^2$-$Alk^2$-$C(Z^1)$=O wherein

Ar is 1,2-, 1,3-, or 1,4-phenylene substituted with COOR', CONHR', O($CH_2$)$_n$COOR', S($CH_2$)$_n$COOR', O($CH_2$)$_n$ CONHR', or S(CH₂)ₙCONHR' and optionally substituted with one or two groups of (C₁-C₆) alkyl, (C₁-C₅) alkoxy, (C₁-C₄) thioalkoxy, halogen, or nitro, wherein n is an integer from 0 to 5 and R' is a branched or unbranched (C₁-C5) chain optionally substituted by one or two groups of —OH, (C₁-C₄) alkoxy, (C₁-C₄) thioalkoxy, halogen, nitro, (C₁-C₃) dialkylamino, or (C₁-C₃) trialkylammonium—A⁻ where A⁻ is a pharmaceutically acceptable anion completing a salt;

Z³ is halogen, hydroxy, OM wherein M is a metal completing a salt, —N₃.

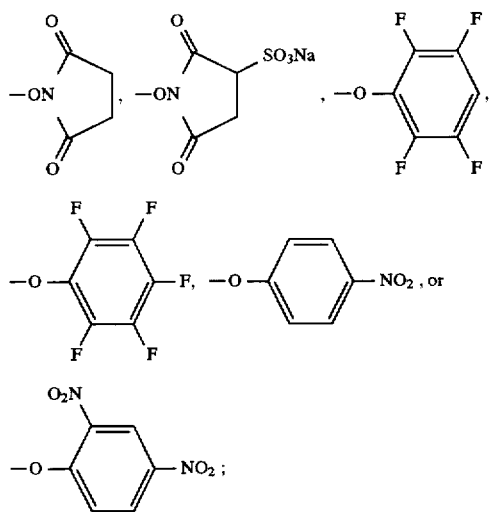

Alk¹ and Alk² are independently a bond or branched or unbranched (C₁-C₁₀) alkylene chain;

Sp¹ is a bond, —S—, —O—, —CONH—, —NHCO—, —NR'—, —N(CH₂CH₂)₂N—, or —X—Ar'—Y—(CH₂)ₙ—Z wherein X, Y, and Z are independently a bond, —NR'—, —S—, or —O—, with the proviso that when n=0, then at least one of Y and Z must be a bond, and Ar' is 1,2-, 1,3-, or 1,4-phenylene optionally substituted with one, two, or three groups of (C₁-C₅) alkyl, (C₁-C₄) alkoxy, (C₁-C₄) thioalkoxy, halogen, nitro, COOR', CONHR', O(CH₂)ₙCOOR', S(CH₂)ₙCOOR', O(CH₂)ₙCONHR', or S(CH₂)ₙCONHR', with the proviso that when Alk¹ is a bond, Sp¹ is a bond wherein n and R' are as hereinbefore defined, with the proviso that when Ar is 1,3- or 1,4-phenylene optionally substituted with one group of (C₁-C₆) alkyl or (C₁-C₅) alkoxy and Alk² is a bond, then Sp¹ is not a bond, —O— or —NHCO—;

Sp² is a bond, —S—, or —O—, with the proviso that when Alk² is a bond, Sp² is a bond;

Z¹ is H or (C₁-C₅) alkyl.

12. A compound according to claim 11, wherein Alk² and Sp² are each a bond.

13. A compound according to claim 12, wherein Alk¹ is a branched or unbranched (C₁—C₁₀) alkylene chain and Sp¹ is a bond, —S—, —O—, —CONH—, —NHCO—, —NR'—, —N(CH₂CH₂)₂N—.

14. A compound according to claim 13, wherein Ar is unsubstituted 1,2-, 1,3-, or 1,4-phenylene.

15. A compound according to claim 14, wherein Z¹ is (C₁-C₅) alkyl.

16. A compound according to claim 15, wherein Z³ is hydroxy.

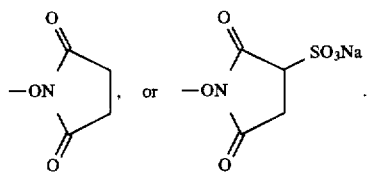

17. A compound of the formula:

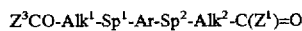

Z³CO-Alk¹-Sp¹-Ar-Sp²-Alk²-C(Z¹)=O wherein

Ar is 1,2-, 1,3-, or 1,4-phenylene optionally substituted with one, two, or three groups of (C₁-C₆) alkyl, (C₁-C₅) alkoxy, (C₁-C₄) thioalkoxy, halogen, or nitro;

Z³ is halogen, hydroxy, OM wherein M is a metal completing a salt, —N₃.

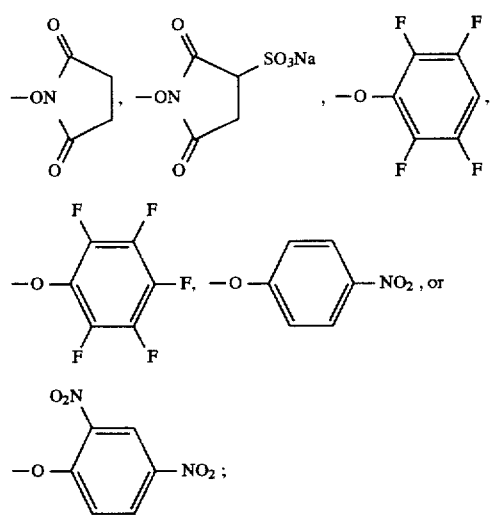

Alk¹ is a branched or unbranched (C₁-C₁₀) alkylene chain;

Alk² is a bond or branched or unbranched (C₁-C₁₀) alkylene chain;

Sp¹ is —CONH—;

Sp² is a bond, —S—, or —O—, with the proviso that when Alk² is a bond, Sp² is a bond;

Z¹ is H or (C₁-C₅) alkyl with the proviso that when Alk¹ is C₂, Alk² is a bond, and Z¹ is C₁, then Ar has at least one substituent, with the proviso that when Alk¹ is C₂, Z¹ is H, Alk² is a bond, and Ar is 1,4-phenylene then Ar has at least one substituent, and with the proviso that when Alk¹ is C₃, Z¹ is C₁, Alk² is a bond, and Ar is 1,4-phenylene, then Ar has at least one substituent.

18. A compound according to claim 17, wherein Alk² and Sp² are each a bond.

19. A compound according to claim 18, wherein Ar is unsubstituted 1,2-, 1,3-, or 1,4-phenylene.

20. A compound according to claim 19, wherein Z¹ is (C₁-C₅) alkyl.

21. A compound according to claim 20, wherein Z³ is hydroxy.

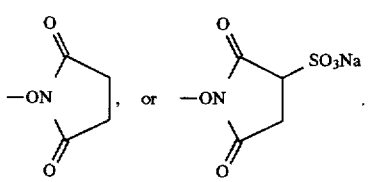

22. A compound of the formula:

$$Z^3CO\text{-}Alk^1\text{-}Sp^1\text{-}Ar\text{-}Sp^2\text{-}Alk^2\text{-}C(Z^1)=O$$

wherein

Ar is 1,2-, 1,3- or 1,4-phenylene optionally substituted with one, two, or three groups of ($C_1$–$C_6$) alkyl, ($C_1$–$C_5$) alkoxy, ($C_1$–$C_4$) thioalkoxy, halogen, or nitro;

$Z^3$ is halogen, hydroxy, OM wherein M is a metal completing a salt, —$N_3$,

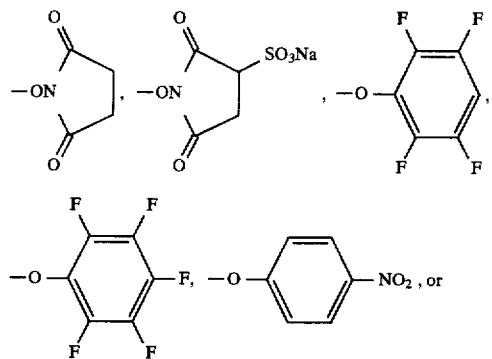

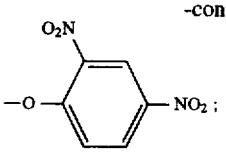

$Alk^1$ is a branched or unbranched ($C_1$–$C_{10}$) alkylene chain;

$Alk^2$ is a bond or a branched or unbranched ($C_1$–$C_{10}$) alkylene chain;

$Sp^1$ is a —S—, —N($CH_2CH_2$)$_2$N—, or —X—Ar'—Y—($CH_2$)$_n$—Z wherein X, Y, and Z are independently a bond, —NR'—, —S—, or —O—, with the proviso that when n=0, then at least one of Y and Z must be a bond, and Ar' is 1,2-, 1,3-, or 1,4-phenylene optionally substituted with one, two, or three groups of ($C_1$–$C_5$) alkyl, ($C_1$–$C_4$) alkoxy, ($C_1$–$C_4$) thioalkoxy, halogen, nitro, COOR', CONHR', O($CH_2$)$_n$COOR', S($CH_2$)$_n$COOR', O($CH_2$)$_n$CONHR', or S($CH_2$)$_n$CONHR', wherein n and R' are as hereinbefore defined;

$Sp^2$ is a bond, —S—, or —O—, with the proviso that when $Alk^2$ is a bond, $Sp^2$ is a bond;

$Z^1$ is H or ($C_1$–$C_5$) alkyl.

23. A compound according to claim 22, wherein $Alk^2$ and $Sp^2$ are each a bond.

24. A compound according to claim 23, wherein $Sp^1$ is a —S— or —N($CH_2CH_2$)$_2$N—.

25. A compound according to claim 24, wherein Ar is unsubstituted 1,2-, 1,3- or 1,4-phenylene.

26. A compound according to claim 25, wherein $Z^1$ is ($C_1$–$C_5$) alkyl.

* * * * *